(12) United States Patent
Kitamura et al.

(10) Patent No.: US 9,676,717 B2
(45) Date of Patent: Jun. 13, 2017

(54) ORGANIC ELECTROLUMINESCENCE DEVICE

(75) Inventors: Tetsu Kitamura, Kanagawa (JP); Toru Watanabe, Kanagawa (JP); Toshihiro Ise, Kanagawa (JP)

(73) Assignee: UDC Ireland Limited, Dublin (IE)

( * ) Notice: Subject to any disclaimer, the term of this patent is extended or adjusted under 35 U.S.C. 154(b) by 972 days.

(21) Appl. No.: 13/522,202

(22) PCT Filed: Dec. 28, 2010

(86) PCT No.: PCT/JP2010/073822
§ 371 (c)(1),
(2), (4) Date: Jul. 13, 2012

(87) PCT Pub. No.: WO2011/086867
PCT Pub. Date: Jul. 21, 2011

(65) Prior Publication Data
US 2013/0020559 A1 Jan. 24, 2013

(30) Foreign Application Priority Data

Jan. 15, 2010 (JP) .................................. 2010-007541
May 20, 2010 (JP) .................................. 2010-116667

(51) Int. Cl.
*H01L 51/54* (2006.01)
*H01L 27/32* (2006.01)
(Continued)

(52) U.S. Cl.
CPC ......... *C07D 209/86* (2013.01); *C07D 221/06* (2013.01); *C07D 235/18* (2013.01);
(Continued)

(58) Field of Classification Search
None
See application file for complete search history.

(56) References Cited

U.S. PATENT DOCUMENTS

2006/0051613 A1   3/2006 Tomita et al.
2006/0280965 A1   12/2006 Kwong et al.
(Continued)

FOREIGN PATENT DOCUMENTS

JP   2007-220721 A   8/2007
JP   2008-543086 A   11/2008
(Continued)

OTHER PUBLICATIONS

International Search Report (PCT/ISA/210) issued by the International Searching Authority in corresponding International Application No. PCT/JP2010/073822 on Mar. 22, 2011.
Written Opinion (PCT/ISA/237) of the International Searching Authority, issued in corresponding International Application No. PCT/JP2010/073822 on Mar. 22, 2011.

*Primary Examiner* — J. L. Yang
(74) *Attorney, Agent, or Firm* — Riverside Law LLP

(57) ABSTRACT

Provided is an organic electroluminescence device including a pair of electrodes composed of an anode and a cathode, a light emitting layer between the electrodes and an organic layer which is adjacent to the light emitting layer between the light emitting layer and the cathode, on a substrate, and the light emitting layer contains at least one compound having a carbazole structure and the organic layer adjacent to the light emitting layer contains at least one hydrocarbon compound having a specific structure.

10 Claims, 3 Drawing Sheets

(51) Int. Cl.
*C07D 209/86* (2006.01)
*C09K 11/06* (2006.01)
*H01L 51/00* (2006.01)
*H05B 33/10* (2006.01)
*C07D 403/12* (2006.01)
*C07D 221/06* (2006.01)
*C07D 235/18* (2006.01)
*C07D 487/22* (2006.01)
*H01L 51/50* (2006.01)
*H01L 51/52* (2006.01)

(52) U.S. Cl.
CPC ......... *C07D 403/12* (2013.01); *C07D 487/22* (2013.01); *C09K 11/06* (2013.01); *H01L 51/0072* (2013.01); *H05B 33/10* (2013.01); *C09K 2211/1007* (2013.01); *C09K 2211/1011* (2013.01); *C09K 2211/1014* (2013.01); *C09K 2211/1029* (2013.01); *H01L 51/0054* (2013.01); *H01L 51/0085* (2013.01); *H01L 51/0087* (2013.01); *H01L 51/0094* (2013.01); *H01L 51/5012* (2013.01); *H01L 51/5268* (2013.01)

(56) References Cited

U.S. PATENT DOCUMENTS

| | | |
|---|---|---|
| 2008/0280163 A1 | 11/2008 | Kwong et al. |
| 2010/0194270 A1 | 8/2010 | Kawamura et al. |
| 2010/0237334 A1 | 9/2010 | Ma et al. |

FOREIGN PATENT DOCUMENTS

| | | | |
|---|---|---|---|
| JP | 2009-218547 A | 9/2009 | |
| WO | 00/41443 A1 | 7/2000 | |
| WO | 03/078541 A1 | 9/2003 | |
| WO | 03/080760 A1 | 10/2003 | |
| WO | 2004/074399 A1 | 9/2004 | |
| WO | 2005/085387 A1 | 9/2005 | |
| WO | 2006/130598 A2 | 12/2006 | |
| WO | 2008/140657 A1 | 11/2008 | |
| WO | WO 2008/140657 A1 * | 11/2008 | ............. C07F 15/00 |
| WO | 2009/008359 A1 | 1/2009 | |
| WO | 2009/021107 A1 | 2/2009 | |
| WO | 2009/021126 A2 | 2/2009 | |
| WO | 2009/030981 A2 | 3/2009 | |

* cited by examiner

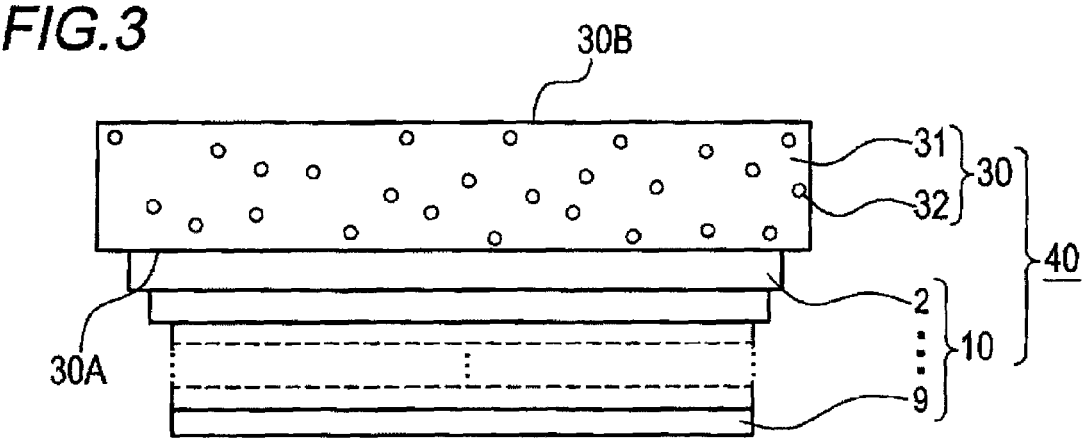

ORGANIC ELECTROLUMINESCENCE DEVICE

TECHNICAL FIELD

The present invention relates to an organic electroluminescence device.

BACKGROUND ART

Organic electroluminescence devices (which may hereinafter be called "devices" or "organic EL devices") are capable of obtaining light emission of high luminance with low voltage driving, and thus have been actively researched and developed. Organic electroluminescence devices have an organic layer interposed between a pair of electrodes and utilize, for light emission, energy of the exciton generated as a result of recombination of electrons injected from a cathode and holes injected from an anode in the organic layer.

Improvement in the efficiency of devices has been recently made by using a phosphorescent light emitting material. Further, doping-type devices, which utilize light emitting layers in which a light emitting material is doped in a host material, have been widely employed.

For example, Patent Documents 1 to 3 have proposed organic electroluminescence devices which have improved light emission efficiency and durability, by using iridium complexes, platinum complexes or the like as a phosphorescent light emitting material, and using a compound with a specific structure containing a nitrogen-containing heterocyclic group and a carbazole structure as a host material.

Likewise, organic electroluminescence devices have been proposed, in which light emission efficiency is improved by using a compound with a specific structure containing a nitrogen-containing heterocyclic group and a carbazole structure as an electron transporting material in an electron transporting layer (see Patent Document 4).

The development of host materials also has been actively conducted, and Patent Document 5 describes an organic electroluminescence device, which uses a phosphorescence emitting material and a hydrocarbon-based material in an electron transporting layer adjacent to a light emitting layer. Furthermore, Patent Document 6 describes a phenyl-substituted mCP derivative and an organic electroluminescence device using this derivative.

However, there is need for an organic electroluminescence device having light emission efficiency and durability at a much higher level than the devices described in these Patent Documents.

RELATED ART

Patent Document

Patent Document 1: International Publication No. WO 05/085387

Patent Document 2: International Publication No. WO 03/080760

Patent Document 3: International Publication No. WO 03/078541

Patent Document 4: Japanese Patent Application Laid-Open No. 2007-220721

Patent Document 5: International Publication No. WO 00/041443

Patent Document 6: International Publication No. WO 04/074399

DISCLOSURE OF INVENTION

Problems to be Solved by the Invention

For illumination purpose, driving at a high luminance of more than 10,000 cd/m$^2$ is also required. According to the study of the present inventors, it has been found out that there are problems in that chromaticity is changed because the light emission position (film thickness direction) in the light emitting layer is changed when driving at a high luminance, compared to the light emission position in driving at a low luminance, and due to heat generation, densification of producing excitons and the like other than a change in the light emission position when driving at a high luminance, the degradation mechanism is different from the mechanism when driving at a low luminance, and a change in chromaticity over time or voltage rise over time is large.

An object of the present invention is to provide an organic electroluminescence device having excellent light emission efficiency and durability. Further, an object thereof is to obtain an organic electroluminescence device having a low driving voltage, a small change in chromaticity when driving at a high luminance, a small change in chromaticity by aging and a small voltage rise by aging.

In addition, another object of the present invention is to provide a light emission apparatus and an illumination apparatus, including the organic electroluminescent device.

Means for Solving the Problems

According to the study of the present inventors, it has been known that the present invention may provide an organic electroluminescence device which has excellent light emission efficiency and durability, a low driving voltage, a small change in chromaticity when driving at a high luminance, a small change in chromaticity by aging and a small voltage rise by aging by containing a specific compound having a carbazole structure in a light emitting layer and including a hydrocarbon compound having a specific condensed polycyclic structure in an organic layer, which is a layer on the cathode side of the light emitting layer, and is adjacent to the light emitting layer.

That is, the present invention may be accomplished by the following means.

[1] An organic electroluminescence device, comprising:

a pair of electrodes composed of an anode and a cathode;

a light emitting layer between the electrodes; and an organic layer which is adjacent to the light emitting layer between the light emitting layer and the cathode, on a substrate, wherein the light emitting layer comprises at least one compound represented by the following Formula (1), and the organic layer adjacent to the light emitting layer, which is on the cathode side of the light emitting layer, comprises at least one hydrocarbon compound represented by Formula (Tp-1):

[Chem. 1]

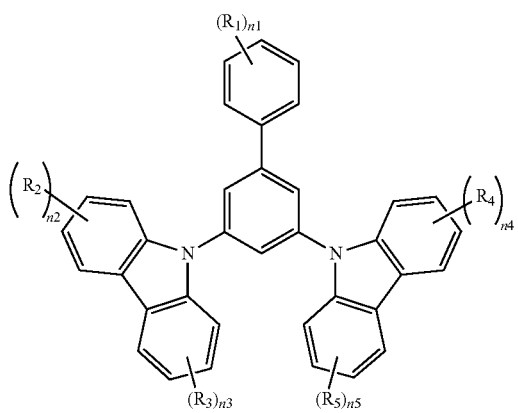

(1)

in Formula (1),

R₁ represents an alkyl group, an aryl group or a silyl group, and may further have a substituent Z, provided that R₁ does not represent a carbazolyl group and a perfluoroalkyl group, in the case where R₁ is present in plurality, each of a plurality of R₁ may be the same or different, a plurality of R₁ may be bonded to each other to form an aryl ring which may have a substituent Z, each of R₂ to R₅ independently represents an alkyl group, an aryl group, a silyl group, a cyano group or a fluorine atom, and may further have a substituent Z, in the case where each of R₂ to R₅ is present in plurality, each of a plurality of R₂ to R₅ may be the same or different, the substituent Z represents an alkyl group, an alkenyl group, a phenyl group, an aromatic heterocyclic group, an alkoxy group, a phenoxy group, a fluorine atom, a silyl group, an amino group, a cyano group or a group formed by combining these groups, and a plurality of the substituents Z may be bonded to each other to form an aryl ring, n1 represents an integer of 0 to 5, each of n2 to n5 independently represents an integer of 0 to 4:

[Chem. 2]

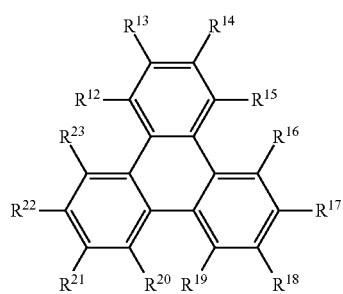

(Tp-1)

in Formula (Tp-1), each of $R^{12}$ to $R^{23}$ independently represents a hydrogen atom, an alkyl group, or a phenyl group, a fluorenyl group, a naphthyl group or a triphenylenyl group, which may be substituted with an alkyl group, a phenyl group, a fluorenyl group, a naphthyl group or a triphenylenyl group, provided that there is no case where all of $R^{12}$ to $R^{23}$ are carbon atoms.

[2] The organic electroluminescence device as described in [1], wherein the compound represented by Formula (1) is a compound represented by the following Formula (2):

[Chem 3]

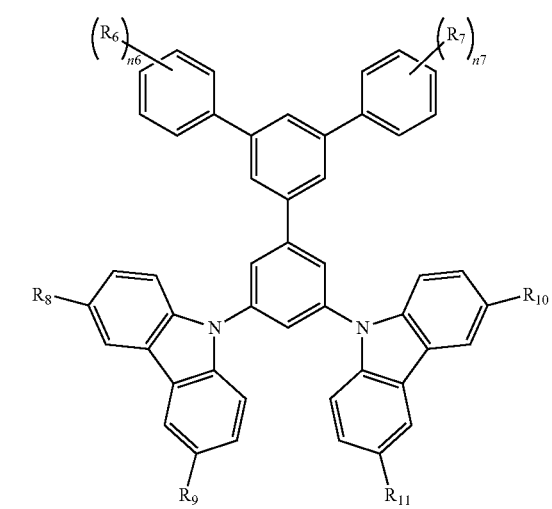

(2)

in Formula (2)

each of R₆ and R₇ independently represents an alkyl group which may have a substituent Z, an aryl group which may have substituent Z, or a cyano group or a fluorine atom, in the case where each of R₆ and R₇ is present in plurality, each of a plurality of R₆ and each of a plurality of R₇ may be the same or different, a plurality of each of R₆ and R₇ may be bonded to each other to form an aryl ring which may have a substituent Z, each of n6 and n7 independently represents an integer of 0 to 5, each of R₈ to R₁₁ independently represents a hydrogen atom, an alkyl group which may have a substituent Z, an aryl group which may have a substituent Z, a silyl group which may have a substituent Z, a cyano group or a fluorine atom, the substituent Z represents an alkyl group, an alkenyl group, a phenyl group, an aromatic heterocyclic group, an alkoxy group, a phenoxy group, a fluorine atom, a silyl group, an amino group, a cyano group or a group formed by combining these groups, and a plurality of substituents Z may be bonded to each other to form an aryl ring.

[3] The organic electroluminescence device as described in [1] or [2], wherein the hydrocarbon compound represented by Formula (Tp-1) is a hydrocarbon compound represented by the following Formula (Tp-2):

[Chem. 4]

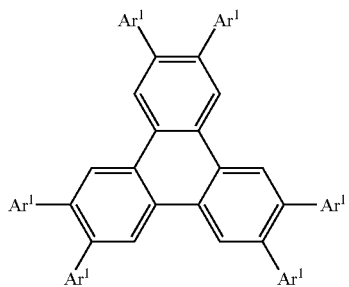

Formula (Tp-2)

in Formula (Tp-2), each of a plurality of $Ar^1$ is the same, and represents a phenyl group, a fluorenyl group, a naphthyl group or a triphenylenyl group, which may be substituted with an alkyl group, a phenyl group, a fluorenyl group, a naphthyl group or a triphenylenyl group.

[4] The organic electroluminescence device as described in [1] or [2], wherein the hydrocarbon compound represented by Formula (Tp-1) is a hydrocarbon compound represented by the following Formula (Tp-3):

[Chem. 5]

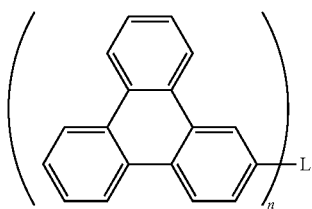

Formula (Tp-3)

in Formula (Tp-3),

L represents a phenyl group, a fluorenyl group, a naphthyl group or a triphenylenyl group, which may be substituted with an alkyl group, a phenyl group, a fluorenyl group, a naphthyl group or a triphenylenyl group, or an n-valent linking group formed by combining these groups, n represents an integer of 1 to 6.

[5] The organic electroluminescence device as described in [1] or [2], wherein the hydrocarbon compound represented by Formula (Tp-1) is a hydrocarbon compound represented by the following Formula (Tp-4):

[Chem. 6]

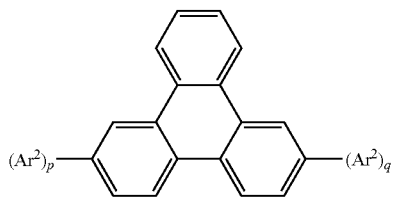

(Tp-4)

in Formula (Tp-4), each of a plurality of $Ar^2$ is the same, and represents an alkyl group, a phenyl group, a naphthyl group, a triphenylenyl group, or a group formed by combining these groups, each of p and q independently represents 0 or 1, provided that p and q are not 0 at the same time, in the case where p and q represent 0, $Ar^2$ represents a hydrogen atom.

[6] The organic electroluminescence device as described in [5], wherein in Formula (Tp-4), $Ar^2$ represents a benzene ring, and the meta position of the benzene ring is substituted with an alkyl group, a phenyl group, a fluorenyl group, a naphthyl group, a triphenylenyl group, or a group formed by combining these groups.

[7] The organic electroluminescence device as described in any one of [1] to [5], wherein the compound represented by Formula (1) is a compound represented by Formula (2), and the hydrocarbon compound represented by Formula (Tp-1) is a hydrocarbon compound represented by Formula (Tp-2), Formula (Tp-3), or Formula (Tp-4).

[8] The organic electroluminescence device as described in any one of [1] to [7], wherein the light emitting layer comprises at least one phosphorescent light emitting material.

[9] The organic electroluminescence device as described in any one of [1] to [8], wherein at least one layer of the light emitting layer, the organic layer adjacent to the light emitting layer and other organic layers present between the anode and the cathode are formed by a solution application process.

[10] The organic electroluminescence device as described in any one of [1] to [9], wherein the device contains a hole injection layer between the electrodes and contains an electron accepting dopant in the hole injection layer.

[11] The organic electroluminescence device as described in any one of [1] to [10], wherein the device contains an electron injection layer between the electrodes and contains an electron donating dopant in the electron injection layer.

[12] A light emission apparatus using the organic electroluminescence device as described in any one of [1] to [11].

[13] A display apparatus using the organic electroluminescence device as described in any one of [1] to [11].

[14] An illumination apparatus using the organic electroluminescence device as described in any one of [1] to [11].

Effects of the Invention

An object of the present invention is to provide an organic electroluminescence device which has excellent light emission efficiency and durability. Moreover, an object of the present invention is to obtain an organic electroluminescence device where a driving voltage is low, a change in chromaticity when driving at a high luminance is small, a change in chromaticity by aging is small and a voltage rise by aging is small.

BRIEF DESCRIPTION OF DRAWINGS

FIG. 3 is a schematic view illustrating an example of an illumination apparatus according to the present invention.

EMBODIMENTS FOR CARRYING OUT THE INVENTION

Figure 1:
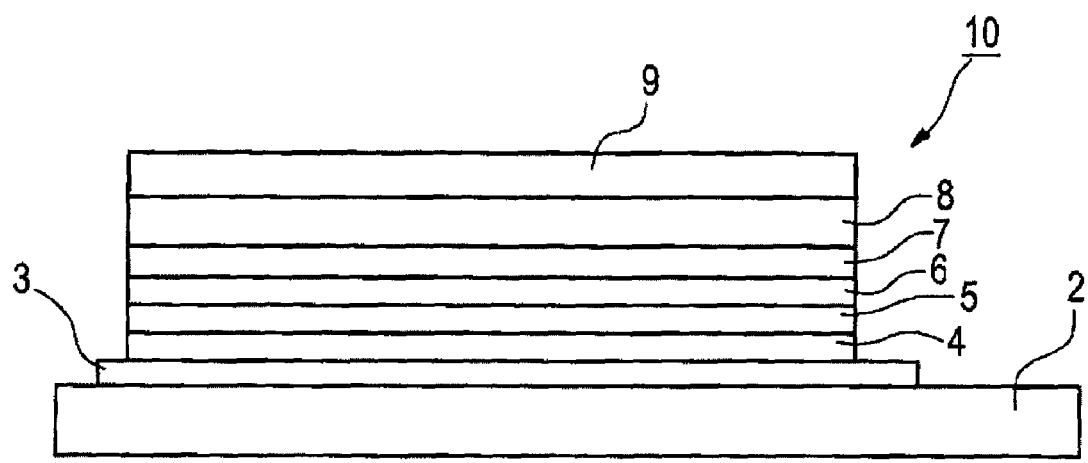
FIG. 1 is a schematic view illustrating an example of a configuration of an organic electroluminescent device according to the present invention.

In the present invention, a substituent Z is defined as follows.

(Substituent Z)

A substituent Z represents an alkyl group, an alkenyl group, a phenyl group, an aromatic heterocyclic group, an alkoxy group, a phenoxy group, a fluorine atom, a silyl group, an amino group, a cyano group or a group formed by combining these groups, and a plurality of substituents Z may be bonded to each other to form an aryl ring.

The substituent Z preferably represents an alkyl group having 1 to 6 carbon atoms, an alkenyl group having 2 to 6 carbon atoms, a phenyl group, an aromatic heterocyclic group having 5 to 10 carbon atoms, an alkoxy group having 1 to 4 carbon atoms, a phenoxy group, a fluorine atom, a silyl group, an amino group, a cyano group or a group formed by combining these groups. A plurality of substituents Z may be linked to each other to form an aromatic hydrocarbon ring.

Furthermore, in the present invention, the groups A and B of substituents will be defined as follows.

(Group A of Substituents)

An alkyl group (having preferably 1 to 30 carbon atoms, more preferably 1 to 20 carbon atoms, and particularly preferably 1 to 10 carbon atoms, and examples thereof include methyl, ethyl, isopropyl, t-butyl, n-octyl, n-decyl, n-hexadecyl, cyclopropyl, cyclopentyl, cyclohexyl and the like), an alkenyl group (having preferably 2 to 30 carbon atoms, more preferably 2 to 20 carbon atoms, and particularly preferably 2 to 10 carbon atoms, and examples thereof include vinyl, allyl, 2-butenyl, 3-pentenyl and the like), an alkynyl group (having preferably 2 to 30 carbon atoms, more preferably 2 to 20 carbon atoms, and particularly preferably 2 to 10 carbon atoms, and examples thereof include propargyl, 3-pentynyl and the like), an aryl group (having preferably 6 to 30 carbon atoms, more preferably 6 to 20 carbon atoms, and particularly preferably 6 to 12 carbon atoms, and examples thereof include phenyl, p-methylphenyl, naphthyl, anthranyl and the like), an amino group (having preferably 0 to 30 carbon atoms, more preferably 0 to 20 carbon atoms, and particularly preferably 0 to 10 carbon atoms, and examples thereof include amino, methylamino, dimethylamino, diethylamino, dibenzylamino, diphenylamino, ditolylamino and the like), an alkoxy group (having preferably 1 to 30 carbon atoms, more preferably 1 to 20 carbon atoms, and particularly preferably 1 to 10 carbon atoms, and examples thereof include methoxy, ethoxy, butoxy, 2-ethylhexyloxy and the like), an aryloxy group (having preferably 6 to 30 carbon atoms, more preferably 6 to 20 carbon atoms, and particularly preferably 6 to 12 carbon atoms, and examples thereof include phenyloxy, 1-naphthyloxy, 2-naphthyloxy and the like), a heterocyclic oxy group (having preferably 1 to 30 carbon atoms, more preferably 1 to 20 carbon atoms, and particularly preferably 1 to 12 carbon atoms, and examples thereof include pyridyloxy, pyrazyloxy, pyrimidyloxy, quinolyloxy and the like), an acyl group (having preferably 2 to 30 carbon atoms, more preferably 2 to 20 carbon atoms, and particularly preferably 2 to 12 carbon atoms, and examples thereof include acetyl, benzoyl, formyl, pivaloyl and the like), an alkoxycarbonyl group (having preferably 2 to 30 carbon atoms, more preferably 2 to 20 carbon atoms, and particularly preferably 2 to 12 carbon atoms, and examples thereof include methoxycarbonyl, ethoxycarbonyl and the like), an aryloxycarbonyl group (having preferably 7 to 30 carbon atoms, more preferably 7 to 20 carbon atoms, and particularly preferably having 7 to 12 carbon atoms, and examples thereof include phenyloxycarbonyl and the like), an acyloxy group (having preferably 2 to 30 carbon atoms, more preferably 2 to 20 carbon atoms, and particularly preferably 2 to 10 carbon atoms, and examples thereof include acetoxy, benzoyloxy and the like), an acylamino group (having preferably 2 to 30 carbon atoms, more preferably 2 to 20 carbon atoms, and particularly preferably 2 to 10 carbon atoms, and examples thereof include acetylamino, benzoylamino and the like), an alkoxycarbonylamino group (having preferably 2 to 30 carbon atoms, more preferably 2 to 20 carbon atoms, and particularly preferably 2 to 12 carbon atoms, and examples thereof include methoxycarbonylamino and the like), an aryloxycarbonylamino group (having preferably 7 to 30 carbon atoms, more preferably 7 to 20 carbon atoms, and particularly preferably 7 to 12 carbon atoms, and examples thereof include phenyloxycarbonylamino and the like), a sulfonylamino group (having preferably 1 to 30 carbon atoms, more preferably 1 to 20 carbon atoms, and particularly preferably 1 to 12 carbon atoms, and examples thereof include methanesulfonylamino, benzenesulfonylamino and the like), a sulfamoyl group (having preferably 0 to 30 carbon atoms, more preferably 0 to 20 carbon atoms, and particularly preferably 0 to 12 carbon atoms, and examples thereof include sulfamoyl, methylsulfamoyl, dimethylsulfamoyl, phenylsulfamoyl and the like), a carbamoyl group (having preferably 1 to 30 carbon atoms, more preferably 1 to 20 carbon atoms, and particularly preferably 1 to 12 carbon atoms, and examples thereof include carbamoyl, methylcarbamoyl, diethylcarbamoyl, phenylcarbamoyl and the like), an alkylthio group (having preferably 1 to 30 carbon atoms, more preferably 1 to 20 carbon atoms, and particularly preferably 1 to 12 carbon atoms, and examples thereof include methylthio, ethylthio and the like), an arylthio group (having preferably 6 to 30 carbon atoms, more preferably 6 to 20 carbon atoms, and particularly preferably 6 to 12 carbon atoms, and examples thereof include phenylthio and the like), a heterocyclic thio group (having preferably 1 to 30 carbon atoms, more preferably 1 to 20 carbon atoms, and particularly preferably 1 to 12 carbon atoms, and examples thereof include pyridylthio, 2-benzimidazolylthio, 2-benzoxazolylthio, 2-benzthiazolylthio and the like), a sulfonyl group (having preferably 1 to 30 carbon atoms, more preferably 1 to 20 carbon atoms, and particularly preferably 1 to 12 carbon atoms, and examples thereof include mesyl, tosyl and the like), a sulfinyl group (having preferably 1 to 30 carbon atoms, more preferably 1 to 20 carbon atoms, and particularly preferably 1 to 12 carbon atoms, and examples thereof include methanesulfinyl, benzenesulfinyl and the like), a ureido group (having preferably 1 to 30 carbon atoms, more preferably 1 to 20 carbon atoms, and particularly preferably 1 to 12 carbon atoms, and examples thereof include ureido, methylureido, phenylureido and the like), a phosphoric acid amide group (having preferably 1 to 30 carbon atoms, more preferably 1 to 20 carbon atoms, and particularly preferably 1 to 12 carbon atoms, and examples thereof include diethylphosphoric acid amide, phenylphosphoric acid amide and the like), a hydroxyl group, a mercapto group, a halogen atom (for example, a fluorine atom, a chlorine atom, a bromine atom and an iodine atom), a cyano group, a sulfo group, a carboxyl group, a nitro group, a hydroxamic acid group, a sulfino group, a hydrazino group, an imino group, a heterocyclic group (also includes an aromatic heterocyclic group, having preferably 1 to 30 carbon atoms, and more preferably 1 to 12 carbon atoms, and examples of the hetero atom include a nitrogen atom, an oxygen atom, a sulfur atom, a phosphorus atom, a silicon atom, a selenium atom and a tellurium atom, and specifically pyridyl, pyrazinyl, pyrimidyl, pyridazinyl, pyrrolyl, pyrazolyl, triazolyl, imidazolyl, oxazolyl, thiazolyl, isoxazolyl, isothiazolyl, quinolyl, furyl, thienyl, selenophenyl, tellurophenyl, piperidyl, piperidino, morpholino, pyrrolidyl, pyrrolidino, benzoxazolyl, benzoimidazolyl, benzothiazolyl, a carbazolyl group, an azepinyl group, a silolyl group and the like), a silyl group (having preferably 3 to 40 carbon atoms, more preferably 3 to 30 carbon atoms, and particularly preferably 3 to 24 carbon atoms, and examples thereof include trimethylsilyl, triphenylsilyl and the like), a silyloxy group (having preferably 3 to 40 carbon atoms, more preferably 3 to 30 carbon atoms, and particularly preferably 3 to 24 carbon atoms, and examples thereof include trimethylsilyloxy, triphenylsilyloxy and the like) and a phosphoryl group (examples thereof include diphenylphosphoryl, dimethylphosphoryl and the like). These substituents may be further substituted, and examples of a further substituent include a group selected from the group A of substituents described above. Further, a substituent substituted with a substituent may be further substituted, and examples of a further substituent include a group selected from the group A of substituents described above. In addition, a substituent substituted with a substituent substituted with a substituent may be further substituted, and examples of a further substituent include groups selected from the group A of substituents described above.

(Group B of Substituents)

An alkyl group (having preferably 1 to 30 carbon atoms, more preferably 1 to 20 carbon atoms, and particularly preferably 1 to 10 carbon atoms, and examples thereof include methyl, ethyl, isopropyl, t-butyl, n-octyl, n-decyl, n-hexadecyl, cyclopropyl, cyclopentyl, cyclohexyl and the like), an alkenyl group (having preferably 2 to 30 carbon atoms, more preferably 2 to 20 carbon atoms, and particularly preferably 2 to 10 carbon atoms, and examples thereof include vinyl, allyl, 2-butenyl, 3-pentenyl and the like), an alkynyl group (having preferably 2 to 30 carbon atoms, more preferably 2 to 20 carbon atoms, and particularly preferably 2 to 10 carbon atoms, and examples thereof include propargyl, 3-pentynyl and the like), an aryl group (having preferably 6 to 30 carbon atoms, more preferably 6 to 20 carbon atoms, and particularly preferably 6 to 12 carbon atoms, and examples thereof include phenyl, p-methylphenyl, naphthyl, anthranyl and the like), a cyano group, a heterocyclic group (also includes an aromatic heterocyclic group, having preferably 1 to 30 carbon atoms, and more preferably 1 to 12 carbon atoms, and examples of the hetero atom include a nitrogen atom, an oxygen atom, a sulfur atom, a phosphorus atom, a silicon atom, a selenium atom and a tellurium atom, and specifically pyridyl, pyrazinyl, pyrimidyl, pyridazinyl, pyrrolyl, pyrazolyl, triazolyl, imidazolyl, oxazolyl, thiazolyl, isoxazolyl, isothiazolyl, quinolyl, furyl, thienyl, selenophenyl, tellurophenyl, piperidyl, piperidino, morpholino, pyrrolidyl, pyrrolidino, benzoxazolyl, benzoimidazolyl, benzothiazolyl, a carbazolyl group, an azepinyl group, a silolyl group and the like). These substituents may be further substituted, and examples of a further substituent include a group selected from the group B of substituents described above. Furthermore, a substituent substituted with a substituent may be further substituted, and examples of a further substituent include a group selected from the group B of substituents described above. Further, a substituent substituted with a substituent substituted with a substituent may be further substituted, and examples of a further substituent include a group selected from the group B of substituents described above.

The organic electroluminescence device of the present invention is an organic electroluminescence device, including: a pair of electrodes composed of an anode and a cathode; a light emitting layer between the electrodes; and an organic layer which is adjacent to the light emitting layer between the light emitting layer and the cathode, on a substrate, and the light emitting layer includes at least one compound represented by the following Formula (1) and the organic layer adjacent to the light emitting layer includes at least one hydrocarbon compound represented by Formula (Tp-1).

According to the present inventors' review, when devices in the related art are driven at a high luminance of more than 10,000 $cd/m^2$, there was a problem in that the a change in chromaticity is larger than the change in chromaticity when driving at a low luminance and a change in chromaticity by aging is large and a voltage rise by aging is large.

The difference in chromaticity between high luminance and low luminance is mainly due to difference in a light emission position (film thickness direction) in the light emitting layer, and this is thought to be due to a charge injection barrier at each layer interface from the electrode to the light emitting layer or the electric field intensity dependence of electric charge mobility of each layer. In the device of the present invention, the electron injection barrier from the cathode to the light emitting layer becomes small and the electric field intensity dependence of electric charge mobility becomes small, and thus, it is presumed that a change in chromaticity by light emitting luminance is small.

Further, the reason why a change in chromaticity by aging or a voltage rise by aging occurs when driving at a high luminance may be thought to be a large heat generation amount, the production of species of reaction activity, such as excitons, radical cations, radical anions and the like at high density, the resultant occurrence of chemical reactions by any combination of a light emitting material, a host material, a material in a layer adjacent to the light emitting layer and the like in addition to the above-described change in the light emitting position.

In the device of the present invention, as described above, a combination of the compound represented by Formula (1) and the hydrocarbon compound represented by Formula (Tp-1) is thought to be a device which is suitable for driving at a high luminance for the reasons that a change in light emitting position hardly occurs, the film is stable for heat, that it is a combination of materials in which chemical reactions hardly occur even though reactive species are generated, and the like.

[Compound Represented by Formula (1)]

Hereinafter, a compound represented by Formula (1) will be described.

[Chem. 7]

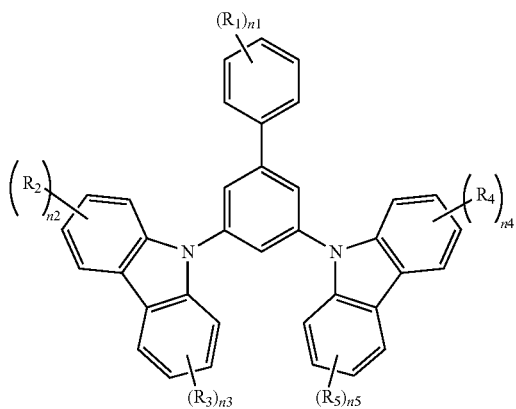

(1)

In Formula (1), $R_1$ represents an alkyl group, an aryl group or a silyl group, and may have a substituent Z, provided that $R_1$ does not represent a carbazolyl group and a perfluoroalkyl group. In the case where $R_1$ is present in plurality, each of a plurality of $R_1$ may be the same or different. In addition, a plurality of $R_1$ may be bonded to each other to form an aryl ring which may have a substituent Z.

Each of $R_2$ to $R_5$ independently represents an alkyl group, an aryl group, a silyl group, a cyano group or a fluorine atom, and may further have a substituent Z. In the case where each of $R_2$ to $R_5$ is present in plurality, each of a plurality of $R_2$ to a plurality of $R_5$ may be the same or different.

A substituent Z represents an alkyl group, an alkenyl group, a phenyl group, an aromatic heterocyclic group, an alkoxy group, a phenoxy group, a fluorine atom, a silyl group, an amino group, a cyano group or a group formed by combining these groups, and a plurality of the substituents Z may be bonded to each other to form an aryl ring.

n1 represents an integer of 0 to 5.

Each of n2 to n5 independently represents an integer of 0 to 4.

The alkyl group represented by $R_1$ may have a substituent, and may be saturated or unsaturated. When the alkyl group has a substituent, examples of the substituent include the above-described Z, and substituent Z is preferably an aryl group and a fluorine atom, and more preferably a fluorine atom. However, $R_1$ does not represent a perfluoroalkyl group. The alkyl group represented by $R_1$ is preferably an alkyl group having 1 to 8 carbon atoms, more preferably an alkyl group having 1 to 6 carbon atoms, and even more preferably an alkyl group having 1 to 4 carbon atoms. Examples thereof include a methyl group, an ethyl group, an n-propyl group, an isopropyl group, an n-butyl group, an isobutyl group, a sec-butyl group, a t-butyl group, an n-pentyl group, an isopentyl group, a 2-methylpentyl group, a neopentyl group, an n-hexyl group, a 4-methylpentyl group, a 3-methylpentyl group, a 2-methylpentyl group, a 3,3-dimethylbutyl group, a 2,2-dimethylbutyl group, a 1,1-dimethylbutyl group, a 1,2-dimethylbutyl group, a 1,3-dimethylbutyl group, a 2,3-dimethylbutyl group and the like, and among them, preferably a methyl group, an isopropyl group, a t-butyl group and a neopentyl group, more preferably a methyl group and a t-butyl group, and even more preferably a t-butyl group.

The aryl group represented by $R_1$ may be in a condensed ring and may have a substituent. When the aryl group has a substituent, examples of the substituent include the above-described substituent Z, and substituent Z is preferably an alkyl group, a cyano group and a fluorine atom, and more preferably an alkyl group. The aryl group represented by $R_1$ is preferably an aryl group having 6 to 30 carbon atoms, and more preferably an aryl group having 6 to 18 carbon atoms. The aryl group having 6 to 18 carbon atoms is preferably an aryl group having 6 to 18 carbon atoms, which may have an alkyl group having 1 to 6 carbon atoms, and more preferably an aryl group having 6 to 18 carbon atoms, which may have an alkyl group having 1 to 4 carbon atoms. Examples thereof include a phenyl group, a dimethylphenyl group, a biphenyl group, a terphenyl group, a naphthyl group, a methylnaphthyl group, a t-butylnaphthyl group, an anthranyl group, a phenanthryl group, a chrysenyl group and the like, and among them, preferably a phenyl group, a dimethylphenyl group, a biphenyl group, a terphenyl group, a naphthyl group, a methylnaphthyl group and a t-butylnaphthyl group, and more preferably a phenyl group, a biphenyl group and a terphenyl group.

The silyl group represented by $R_1$ may have a substituent. When the silyl group has a substituent, examples of the substituent include the above-described substituent Z, and substituent Z is preferably an alkyl group and an aryl group, more preferably a methyl group and a phenyl group, and most preferably a phenyl group. The silyl group represented by $R_1$ is preferably a silyl group having 0 to 18 carbon atoms, and more preferably a silyl group having 3 to 18 carbon atoms. The silyl group having 3 to 18 carbon atoms is preferably a silyl group having 3 to 18 carbon atoms, substituted with an alkyl group having 1 to 6 carbon atoms or an aryl group, more preferably all of the three hydrogen atoms of the silyl group, substituted with any of an alkyl group having 1 to 6 carbon atoms and an aryl group, and even more preferably all substituted with a phenyl group. Examples thereof include a trimethylsilyl group, a triethylsilyl group, a t-butyldimethylsilyl group, a diethylisopropylsilyl group, a dimethylphenylsilyl group, a diphenylmethylsilyl group, a triphenylsilyl group and the like, and among them, preferably a trimethylsilyl group, a dimethylphenylsilyl group and a triphenylsilyl group, and more preferably a triphenylsilyl group.

When $R_1$ is present in plurality, each of a plurality of $R_1$ may be the same or different. Furthermore, a plurality of $R_1$ may be bonded to each other to form an aryl ring which may have a substituent Z. The substituent Z is preferably an alkyl group, an aryl group, a silyl group, a cyano group and a fluorine atom, and more preferably an alkyl group. However, $R_1$ does not represent a carbazolyl group and a perfluoroalkyl group.

The aryl ring which is formed by bonding a plurality of $R_1$ to each other is preferably an aryl ring having 6 to 30 carbon atoms, including a carbon atom which the plurality of $R_1$ substitute, and more preferably an aryl ring having 6 to 14 carbon atoms. A ring to be formed is preferably any of a benzene ring, a naphthalene ring and a phenanthrene ring, more preferably a benzene ring and a phenanthrene ring, and even more preferably a benzene ring. Meanwhile, the ring formed by the plurality of $R_1$ may be present in plural numbers, and for example, a plurality of $R_1$ may represent an alkyl group, a plurality of the alkyl groups may be bonded to each other to form two benzene rings, and a phenanthrene ring may be formed with the benzene rings where a plurality of the alkyl group are substituted.

From the viewpoints of electric charge transporting ability and stability for electric charge, $R_1$ is preferably any of an alkyl group, an aryl group which may have an alkyl group and a silyl group substituted with an alkyl group or a phenyl group, more preferably any of an aryl group having 6 to 18 carbon atoms, which may have an alkyl group having 1 to 6 carbon atoms and a silyl group having 3 to 18 carbon atoms, substituted with an alkyl group or a phenyl group having 1 to 6 carbon atoms, even more preferably an aryl group having 6 to 18 carbon atoms, which may have an alkyl group having 1 to 6 carbon atoms, and particularly preferably an aryl group having 6 to 18 carbon atoms, which may have an alkyl group having 1 to 4 carbon atoms.

Among them, $R_1$ is preferably a methyl group, a t-butyl group, a neopentyl group, an unsubstituted phenyl group, a phenyl group substituted with a cyano group, a fluorine atom or a trifluoromethyl group, a biphenyl group, a terphenyl group, an unsubstituted naphthyl group, a naphthyl group substituted with a methyl group or a t-butyl group, a triphenylsilyl group, a benzene ring or a phenanthrene ring formed by bonding a plurality of alkyl groups or aryl groups to each other, more preferably a phenyl group, a biphenyl group or a terphenyl group, and even more preferably a phenyl group or a biphenyl group.

n1 is preferably an integer of 0 to 4, more preferably an integer of 1 to 4, and even more preferably an integer of 1 to 2.

Specific examples and preferred examples of an aryl group and a silyl group represented by $R_2$ to $R_5$ are the same as specific examples and preferred examples of the aryl group and the silyl group represented by $R_1$. Examples of the alkyl group represented by $R_2$ to $R_5$ include a perfluoroalkyl group such as a trifluoromethyl group and the like, in addition to examples of the alkyl group represented by $R_1$. Among them, a methyl group, a trifluoromethyl group, an isopropyl group, a t-butyl group or a neopentyl group is preferred, a methyl group or a t-butyl group is more preferred and a t-butyl group is even more preferred.

From the viewpoint of electric charge transporting ability and stability for electric charge, each of $R_2$ to $R_5$ is independently preferably any of an alkyl group having 1 to 6 carbon atoms, an aryl group having 6 to 18 carbon atoms, a silyl group having 3 to 18 carbon atoms, a cyano group and a fluorine atom, and more preferably any of an alkyl group having 1 to 4 carbon atoms, an aryl group having 6 to 12 carbon atoms, a silyl group having 3 to 18 carbon atoms, a cyano group and a fluorine atom.

Among them, $R_2$ to $R_5$ are preferably any of a methyl group, an isopropyl group, a t-butyl group, a neopentyl group, a trifluoromethyl group, a phenyl group, a dimethylphenyl group, a trimethylsilyl group, a triphenylsilyl group, a fluorine atom and a cyano group, more preferably a t-butyl group, a phenyl group, a trimethylsilyl group or a triphenylsilyl group, and even more preferably a t-butyl group, a phenyl group or a triphenylsilyl group.

Each of n2 to n5 is independently preferably an integer of 0 to 2, and more preferably 0 or 1. When a substituent is introduced into a carbazole structure, the 3- and 6-positions of the carbazole structure are a reaction active position, and a substituent is preferably introduced into the position from the viewpoint of easiness of synthesis and improving chemical stability.

The compound represented by Formula (1) is more preferably represented by the following Formula (2).

[Chem 8]

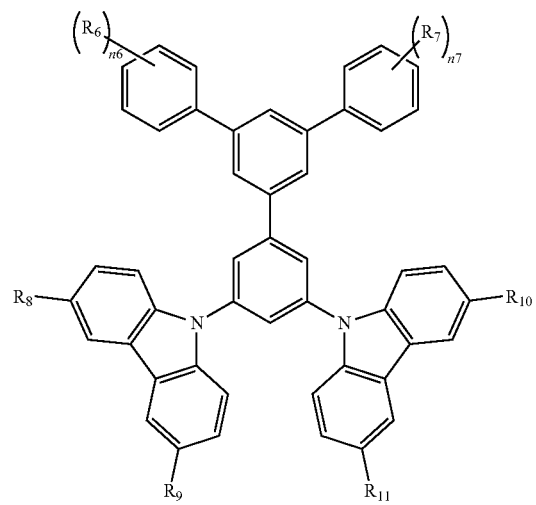

(2)

In Formula (2), each of $R_6$ and $R_7$ independently represents an alkyl group which may have a substituent Z, an aryl group which may have a substituent Z, a cyano group or a fluorine atom. In the case where each of $R_6$ and $R_7$ is present in plurality, each of a plurality of $R_6$ and each of a plurality of $R_7$ may be the same or different. Further, a plurality of $R_6$ and a plurality of $R_7$ may be bonded to each other to form an aryl ring which may have a substituent Z.

Each of n6 and n7 independently represents an integer of 0 to 5.

Each of $R_8$ to $R_{11}$ independently represents a hydrogen atom, an alkyl group which may have a substituent Z, an aryl group which may have a substituent Z, a silyl group which may have a substituent Z, a cyano group or a fluorine atom.

The substituent Z represents an alkyl group, an alkenyl group, a phenyl group, an aromatic heterocyclic group, an alkoxy group, a phenoxy group, a fluorine atom, a silyl group, an amino group, a cyano group or a group formed by combining these groups, and a plurality of the substituents Z may be bonded to each other to form an aryl ring.

The alkyl group represented by $R_6$ and $R_7$ may have a substituent, and may be saturated or unsaturated. When the alkyl group has a substituent, examples of the substituent include the above-described substituent Z, and the substituent Z is preferably an aryl group and a fluorine atom, and more preferably a fluorine atom.

The alkyl group represented by $R_6$ and $R_7$ is preferably an alkyl group having 1 to 6 carbon atoms, and more preferably an alkyl group having 1 to 4 carbon atoms. Specific examples and preferred examples of the alkyl group represented by $R_6$ and $R_7$ are the same as specific examples and preferred examples of the alkyl group represented by $R_2$ to $R_5$ in Formula (1).

The aryl group represented by $R_6$ and $R_7$ may have a substituent, examples of the substituent include the above-described substituent Z, and substituent Z is preferably an alkyl group, an aryl group and a fluorine atom, and more preferably an alkyl group. The alkyl group is preferably an alkyl group having 1 to 6 carbon atoms, and more preferably an alkyl group having 1 to 4 carbon atoms. Specific examples and preferred examples of the alkyl group are the same as specific examples and preferred examples of the alkyl group represented by $R_2$ to $R_5$ in Formula (1). The aryl group is preferably an aryl group having 6 to 30 carbon atoms, and more preferably an aryl group having 6 to 18 carbon atoms. Specific examples and preferred examples of the aryl group are the same as specific examples and preferred examples of the aryl group represented by $R_1$ in Formula (1).

An aryl group represented by $R_6$ and $R_7$ is preferably an unsubstituted aryl group.

In addition, the aryl group represented by $R_6$ and $R_7$ is preferably an aryl group having 6 to 18 carbon atoms and more preferably an aryl group having 6 to 12 carbon atoms. Examples thereof include a phenyl group, a biphenyl group, a terphenyl group, a naphthyl group, an anthranyl group, a phenanthryl group, a chrysenyl group and the like. Among them, a phenyl group, a biphenyl group, a terphenyl group, a naphthyl group are preferable, more preferably a phenyl group, a biphenyl group, a terphenyl group, and even more preferably a phenyl group.

When each of $R_6$ and $R_7$ is present in plurality, each $R_6$ and each $R_7$ may be the same as or different from every other $R_6$ and every other $R_7$, respectively. Furthermore, a plurality of $R_6$ and a plurality of $R_7$ may be bonded to each other to form an aryl ring which may have the above-described substituent Z. The substituent Z is preferably an alkyl group, an aryl group, a silyl group, a cyano group and a fluorine atom, and more preferably an alkyl group.

The aryl ring, formed by bonding a plurality of $R_6$ and a plurality of $R_7$ to each other respectively, is preferably an aryl ring having 6 to 30 carbon atoms, including a carbon atom where each of the plurality of $R_6$ and the plurality of $R_7$ is substituted, more preferably an aryl ring having 6 to 14 carbon atoms, and even more preferably an aryl ring having 6 to 14 carbon atoms, which may have an alkyl group having 1 to 4 alkyl group. A ring to be formed is preferably any of a benzene ring, a naphthalene ring and a phenanthrene ring, which may have an alkyl group having 1 to 4 carbon atoms, and more preferably a benzene ring which may have an alkyl group having 1 to 4 carbon atoms, and examples thereof include a benzene ring and a benzene ring substituted with a t-butyl group. Meanwhile, the ring formed by a plurality of $R_6$ or a plurality of $R_7$ may be present in plural numbers, and for example, a plurality of $R_6$ or a plurality of $R_7$ may be bonded to each other to form two benzene rings and a phenanthrene ring may be formed with the benzene rings where the plurality of $R_6$ or the plurality of $R_7$ are substituted.

From the viewpoint of electric charge transporting ability and stability for electric charge, $R_6$ and $R_7$ is preferably an alkyl group, an aryl group which may have an alkyl group, a cyano group or a fluorine atom, more preferably an alkyl group having 1 to 6 carbon atoms, an aryl group having 6 to 18 carbon atoms which may have an alkyl group having 1 to 6 carbon atoms, a cyano group or a fluorine atom, and more preferably an alkyl group having 1 to 4 carbon atoms, an aryl group having 6 to 12 carbon atoms, which may have an alkyl group having 1 to 4 carbon atoms, a cyano group or a fluorine atom.

Among them, each of $R_6$ and $R_7$ is independently preferably any of a methyl group, a trifluoromethyl group, a t-butyl group, an unsubstituted phenyl group, a phenyl group substituted with a t-butyl group, a biphenyl group, a cyano group, a fluorine atom, an unsubstituted benzene ring which is formed by bonding a plurality of alkyl groups to each other and a benzene ring substituted with a t-butyl group, more preferably any of a t-butyl group, an unsubstituted phenyl group, a phenyl group substituted with a t-butyl group and a biphenyl group, and particularly preferably an unsubstituted phenyl group.

Each of n6 and n7 is independently preferably an integer of 0 to 4, more preferably an integer of 0 to 2, and even more preferably 0 or 1.

An alkyl group represented by $R_8$ to $R_{11}$ may have a substituent, and may be saturated or unsaturated. When the alkyl group has a substituent, examples of the substituent include the above-described substituent Z, and substituent Z is more preferably a fluorine atom.

The alkyl group represented by $R_8$ to $R_{11}$ is preferably an alkyl group having 1 to 6 carbon atoms, and more preferably an alkyl group having 1 to 4 carbon atoms. Specific examples and preferred examples of the alkyl group represented by $R_8$ to $R_{11}$ are the same as specific examples and preferred examples of the alkyl group represented by $R_2$ to $R_5$ in Formula (1).

The aryl group represented by $R_8$ to $R_{11}$ is preferably an aryl group having 6 to 18 carbon atoms, which may have an alkyl group having 1 to 6 carbon atoms, and more preferably an aryl group having 6 to 12 carbon atoms, which may have an alkyl group having 1 to 4 carbon atoms.

Specific examples and preferred examples of the aryl group, represented by $R_8$ to $R_{11}$, are the same as specific examples and preferred examples of the above-described aryl group, represented by $R_6$ and $R_7$.

A silyl group represented by $R_8$ to $R_{11}$ may have a substituent. When the silyl group has a substituent, examples of the substituent include the above-described substituent Z, and substituent Z is preferably an alkyl group and an aryl group, and more preferably a phenyl group. The silyl group represented by $R_8$ to $R_{11}$ is preferably a silyl group having 3 to 18 carbon atoms, and specific examples and preferred examples of the silyl group having 3 to 18 carbon atoms, represented by $R_8$ to $R_{11}$, are the same as specific examples and preferred examples of the silyl group having 3 to 18 carbon atoms in the silyl group represented by $R_1$ in Formula (1).

From the viewpoint of electric charge transporting ability and stability for electric charge, each of $R_8$ to $R_{11}$ is independently preferably any of a hydrogen atom, an alkyl group having 1 to 6 carbon atoms, an aryl group having 6 to 18 carbon atoms, a silyl group having 3 to 18 carbon atoms, a cyano group and a fluorine atom, and more preferably any of a hydrogen atom, an alkyl group having 1 to 4 carbon atoms, an aryl group having 6 to 12 carbon atoms, a silyl group having 3 to 18 carbon atoms, a cyano group and a fluorine atom.

Among them, each of $R_8$ to $R_{11}$ are independently preferably any of a hydrogen atom, a methyl group, an isopropyl group, a t-butyl group, a neopentyl group, a trifluoromethyl group, a phenyl group, a dimethylphenyl group, a trimethylsilyl group, a triphenylsilyl group, a fluorine atom or a cyano group, more preferably a hydrogen atom, a t-butyl group, a phenyl group, a trimethylsilyl group and a triphenylsilyl group, and even more preferably a hydrogen atom, a t-butyl group, a phenyl group or a triphenylsilyl group.

It is most preferred that the compound represented by Formula (1) or Formula (2) is composed only of carbon atoms, hydrogen atoms and nitrogen atoms.

The compound represented by Formula (1) or Formula (2) has a molecular weight of preferably 400 to 1,000, more preferably 450 to 800, and even more preferably 500 to 700.

The lowest triplet excited state ($T_1$) energy of the compound represented by Formula (1) or Formula (2) in the state of film is preferably 2.61 eV (62 kcal/mol) to 3.51 eV (80 kcal/mol), more preferably 2.69 eV (63.5 kcal/mol) to 3.51 eV (75 kcal/mol), and even more preferably 2.76 eV (65 kcal/mol) to 3.51 eV (70 kcal/mol).

The glass transition temperature (Tg) of the compound represented by Formula (1) or Formula (2) is preferably 80° C. to 400° C., more preferably 100° C. to 400° C., and even more preferably 120° C. to 400° C.

When Formula (1) or Formula (2) has a hydrogen atom, an isotope (a deuterium atom and the like) is also included. In this case, all the hydrogen atoms in the compound may be substituted with the isotope and may also be a mixture in which a part thereof are a compound including the isotope.

Hereinafter, specific examples of the compound represented by Formula (1) or Formula (2) will be exemplified, but the present invention is not limited thereto.

[Chem. 9]

(A-1)
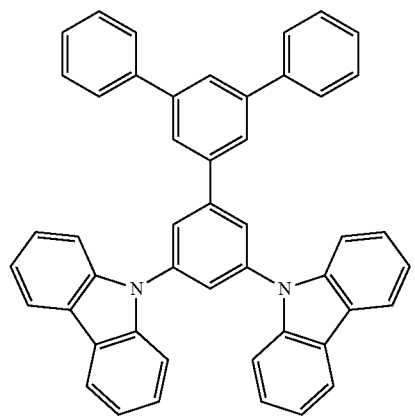

(A-2)
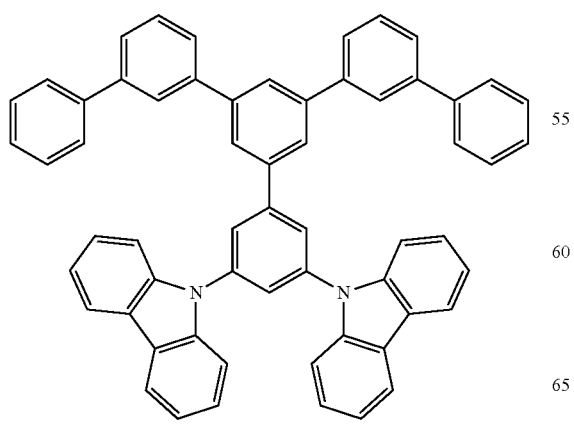

(A-3)
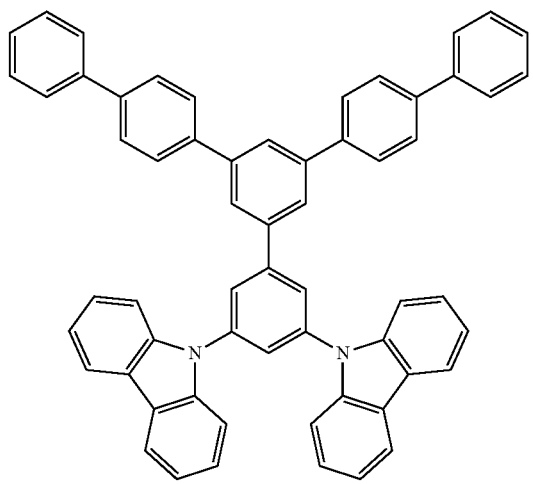

(A-4)
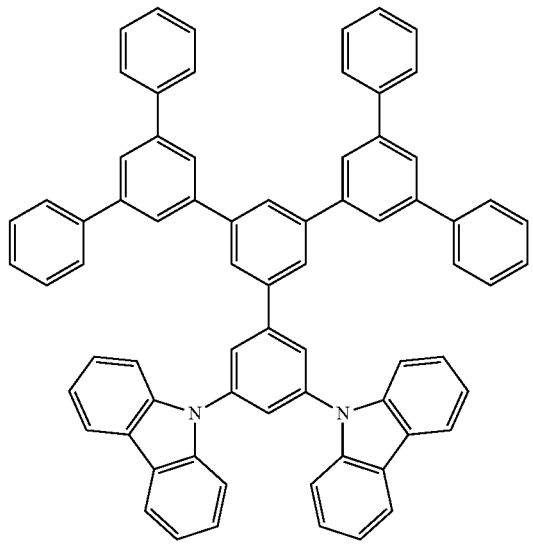

(A-5)
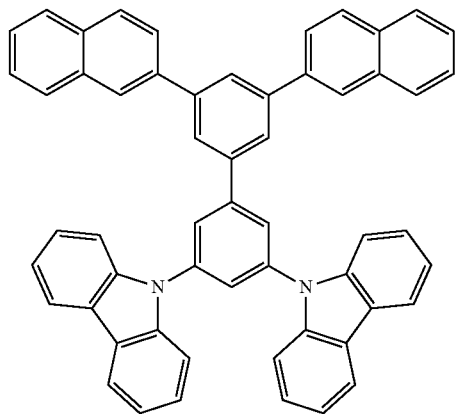

-continued
(A-6)
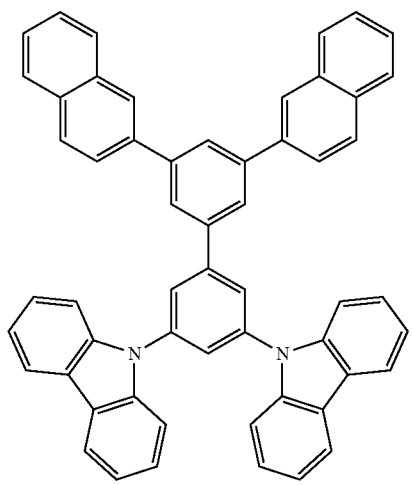
(A-7)
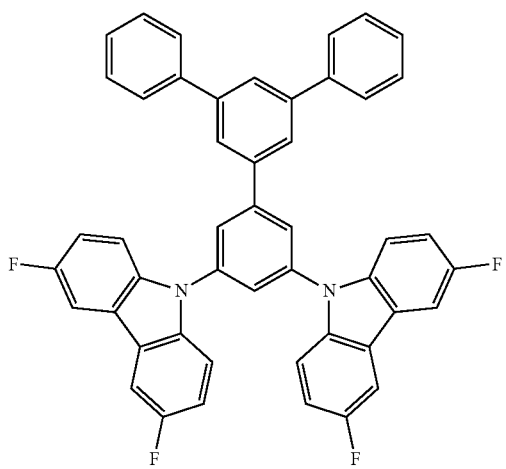
(A-8)
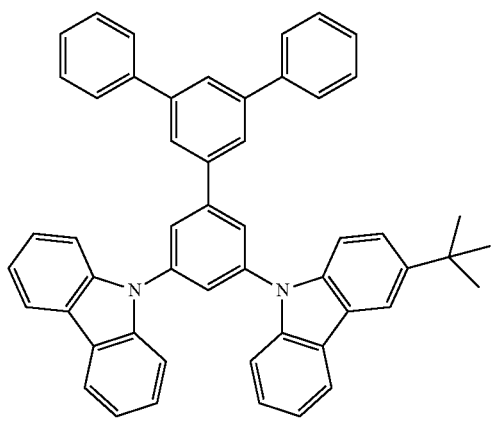
-continued
(A-9)
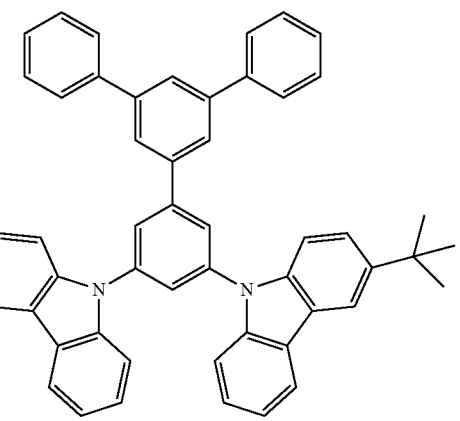
(A-10)
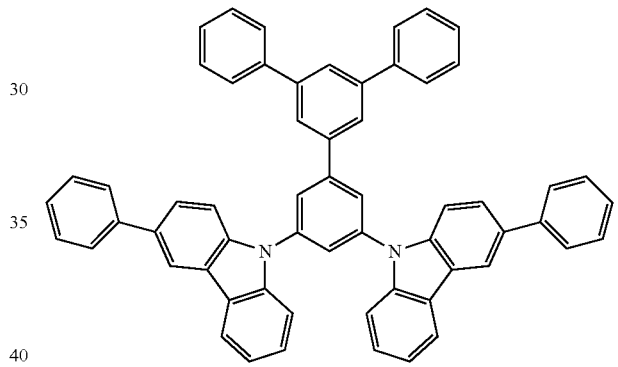
(A-11)
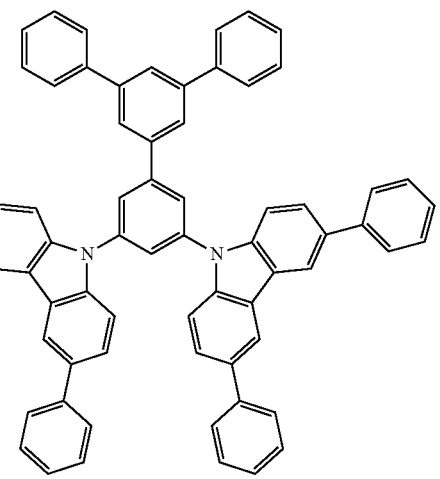

(A-12)
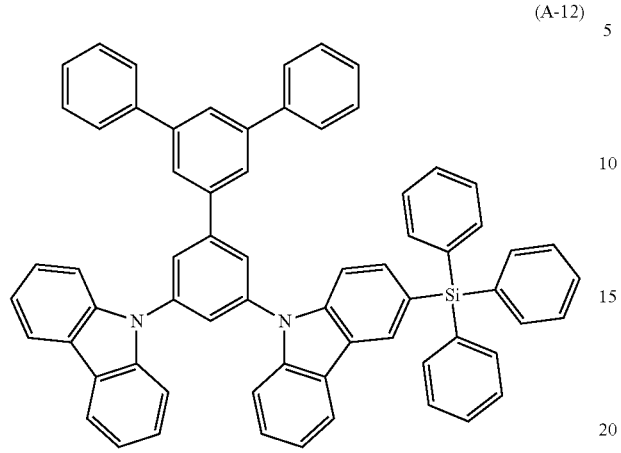
(A-13)
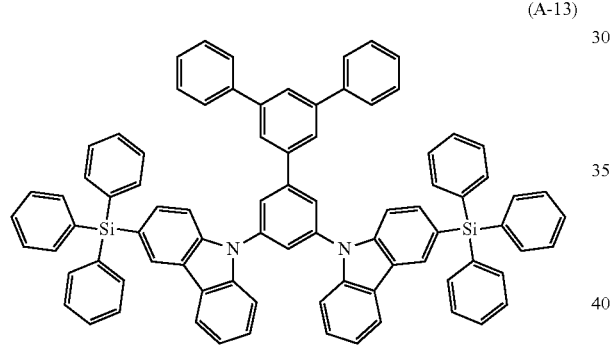
(A-14)
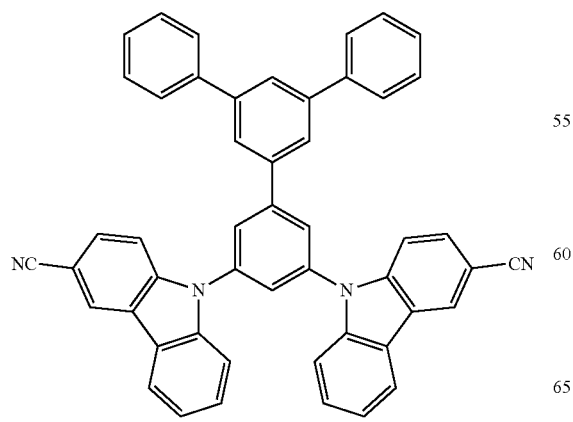
(A-15)
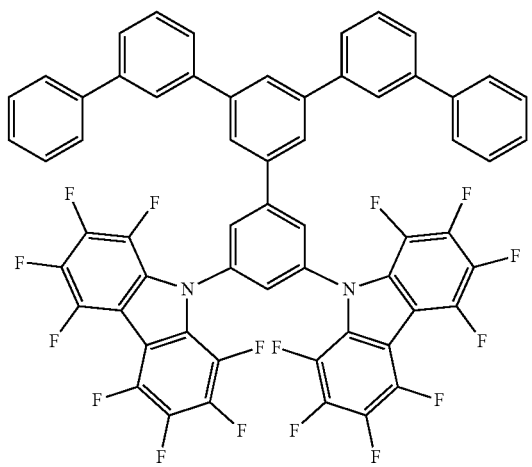
(A-16)
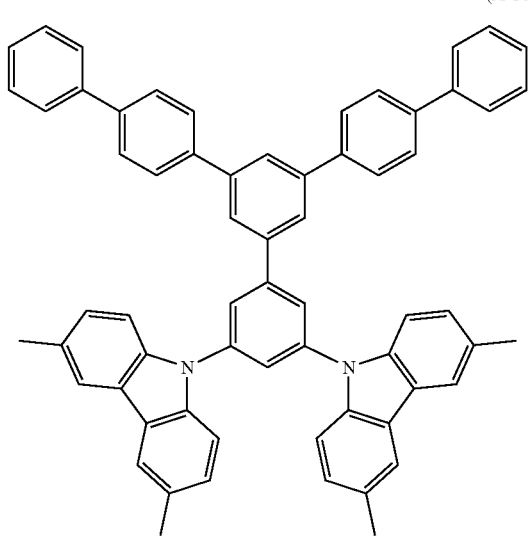
(A-17)
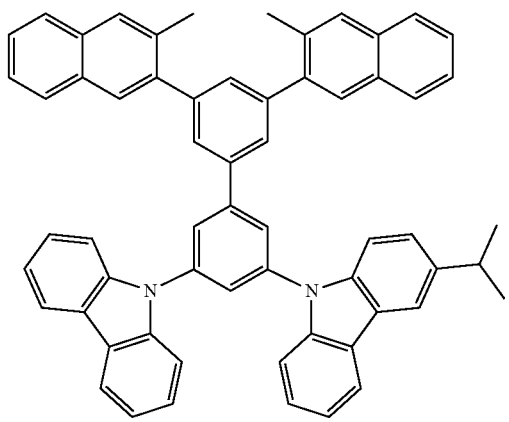

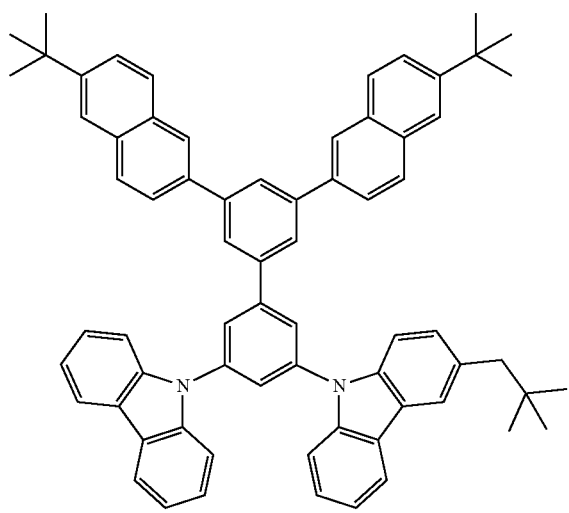
(A-18)
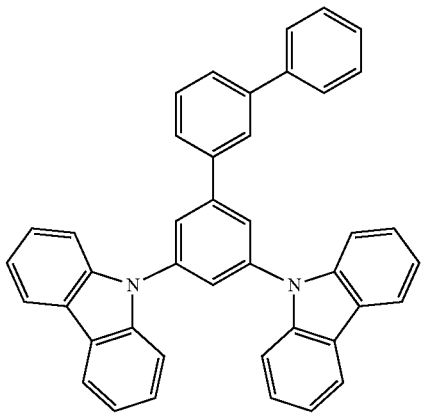
(A-21)
(A-19)
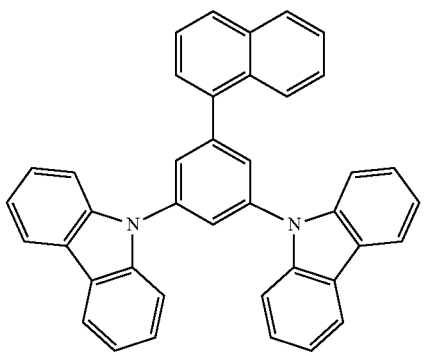
(A-22)
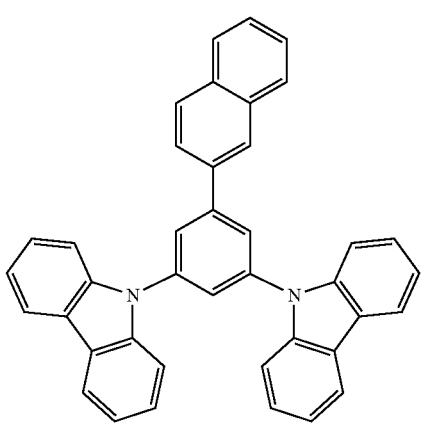
(A-20)
(A-23)
(A-24)

(A-25)
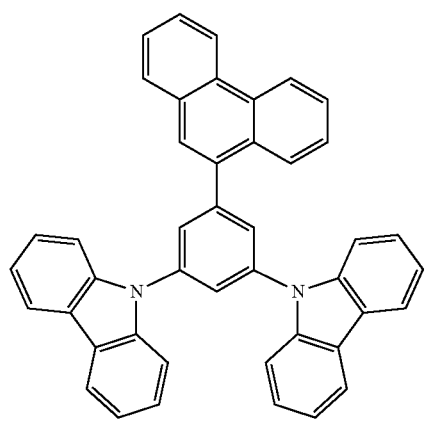
[Chem. 11]
(A-26)
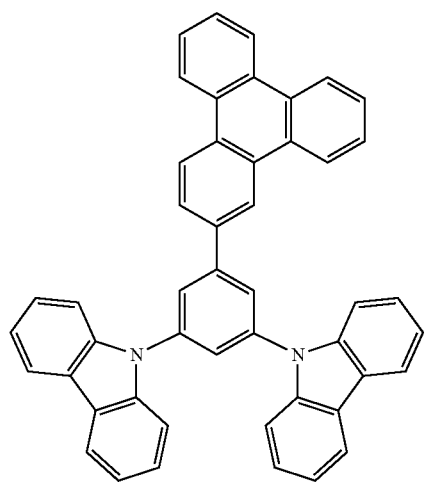
(A-27)
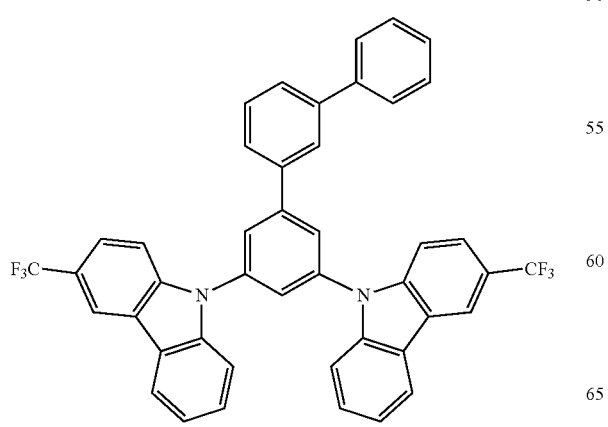
(A-28)
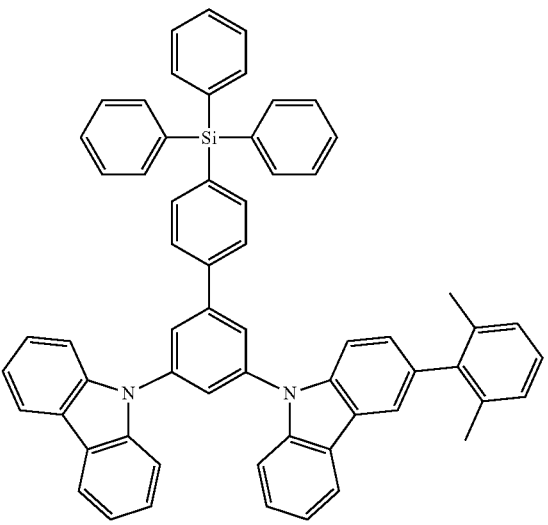
(A-29)
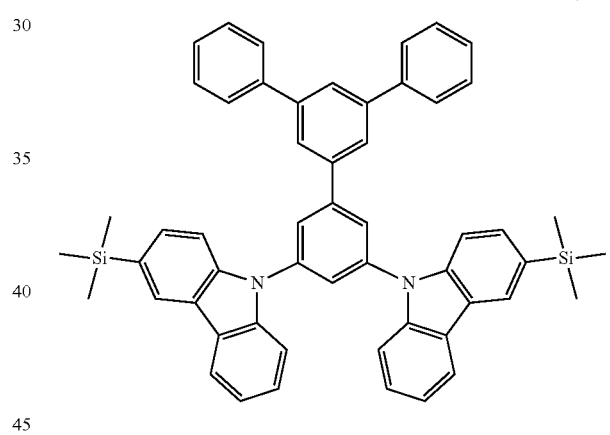
(A-30)
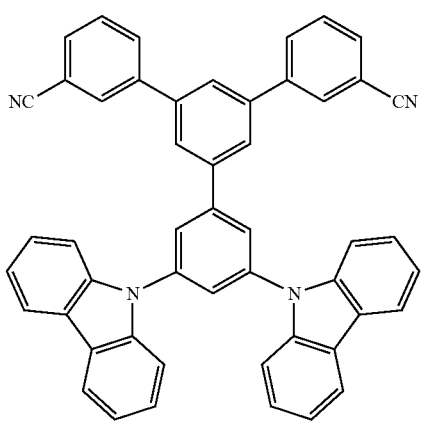

(A-31)
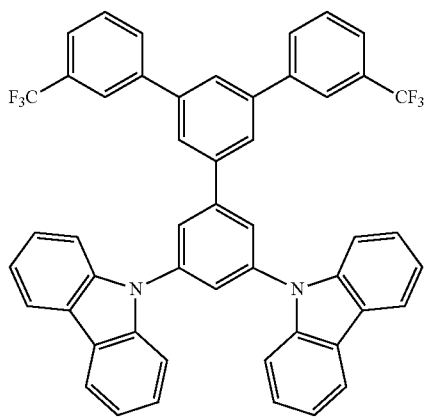

[Chem. 12]
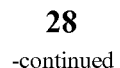
(A-34)
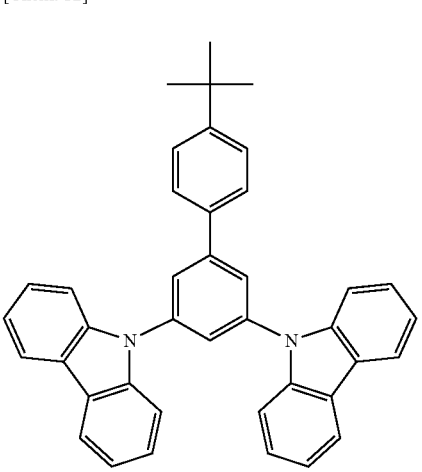

(A-32)
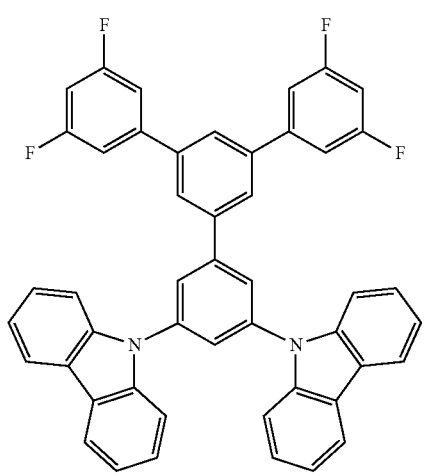

(A-35)
(A-36)
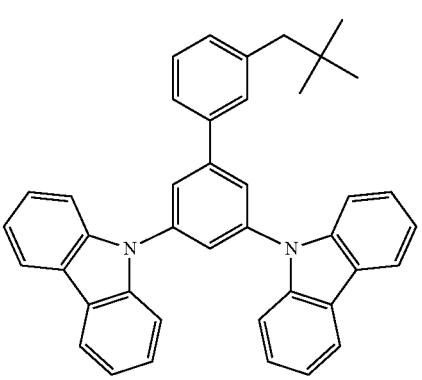

(A-33)
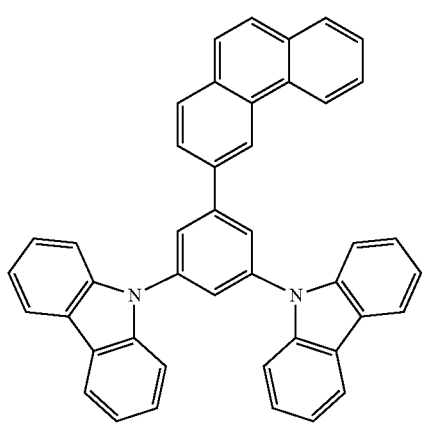

The compound exemplified as a compound represented by Formula (1) or Formula (2) may be synthesized with reference to the International Publication No. WO 2004/074399 and the like. For example, compound (A-1) may be synthesized by a method described in page 52, line 22 to page 54, line 15 of International Publication No. WO 2004/074399.

In the present invention, the compound represented by Formula (1) or Formula (2) is contained in the light emitting layer, the use thereof is not limited, and the compound may be further contained in any layer in the organic layer. Examples of an introducing layer of the compound represented by Formula (1) or Formula (2) include any one of a light emitting layer, a hole injection layer, a hole transporting layer, an electron transporting layer, an electron injection layer, an exciton blocking layer and a charge blocking layer.

The compound represented by Formula (1) or Formula (2) is contained in an amount of preferably 0.1 mass % to 99 mass %, more preferably 1 mass % to 95 mass %, and even more preferably 10 mass % to 95 mass %, based on the total mass of the light emitting layer. When the compound represented by Formula (1) or Formula (2) is further contained in a layer other than the light emitting layer, the compound is included in an amount of preferably 70 mass % to 100 mass %, and more preferably 85 mass % to 100 mass %, based on the total mass of the layer.

[Hydrocarbon Compound Represented by Formula (Tp-1)]

Hereinafter, a hydrocarbon compound represented by Formula (Tp-1) (hereinafter, simply referred to as a "hydrocarbon compound" in some cases) will be described.

The hydrocarbon compound is composed only of carbon atoms and hydrogen atoms and thus has excellent chemical stability, thereby having high driving durability and showing an effect that various changes are difficult to occur when driving at high luminance The hydrocarbon compound represented by Formula (Tp-1) has a molecular weight preferably in a range of 400 to 1,200, more preferably 400 to 1,000, and even more preferably 400 to 800. When the molecular weight is 400 or more, a good quality amorphous thin film may be formed. When the molecular weight is 1,200 or less, it is preferable from the viewpoint of the solubility in a solvent or sublimation and deposition suitability.

For the hydrocarbon compound represented by Formula (Tp-1), the use thereof is not limited, and the hydrocarbon compound may be further contained in not only an organic layer adjacent to a light emitting layer, but also any layer in the organic layer.

[Chem. 13]

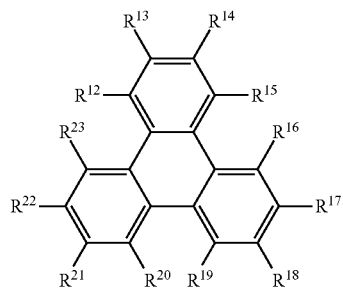

(Tp-1)

(In Formula (Tp-1), each of $R^{12}$ to $R^{23}$ independently represents a hydrogen atom, an alkyl group or, a phenyl group, a fluorenyl group, a naphthyl group or a triphenylenyl group, which may be substituted with an alkyl group, a phenyl group, a fluorenyl group, a naphthyl group or a triphenylenyl group. However, there is no case where all of $R^{12}$ to $R^{23}$ are hydrogen atoms.)

The alkyl group represented by $R^{12}$ to $R^{23}$ is a substituted or unsubstituted alkyl group, for example, a substituted or unsubstituted, a methyl group, an ethyl group, an isopropyl group, an n-butyl group, a t-butyl group, an n-octyl group, an n-decyl group, an n-hexadecyl group, a cyclopropyl group, a cyclopentyl group, a cyclohexyl group and the like, preferably a methyl group, an ethyl group, an isopropyl group, a t-butyl group and a cyclohexyl group, and more preferably a methyl group, an ethyl group, or a t-butyl group.

$R^{12}$ to $R^{23}$ are preferably an alkyl group having 1 to 4 carbon atoms, or a phenyl group, a fluorenyl group, a naphthyl group or a triphenylenyl group, which may be substituted with an alkyl group having 1 to 4 carbon atoms, a phenyl group, a fluorenyl group, a naphthyl group or a triphenylenyl group (which may be further substituted with an alkyl group, a phenyl group, a fluorenyl group, a naphthyl group or a triphenylenyl group).

A phenyl group which may be substituted with a phenyl group, a fluorenyl group, a naphthyl group or a triphenylenyl group (which may be further substituted with an alkyl group, a phenyl group, a fluorenyl group, a naphthyl group or a triphenylenyl group) is particularly preferred.

Each of $R^{12}$ to $R^{23}$ independently preferably has a total carbon number of 20 to 50, and more preferably 20 to 36. By setting the number within the range, a good quality amorphous thin film may be formed, and the solubility in a solvent or sublimation and deposition suitability is improved.

According to an aspect of the present invention, the hydrocarbon compound represented by Formula (Tp-1) is preferably a hydrocarbon compound represented by the following Formula (Tp-2).

[Chem. 14]

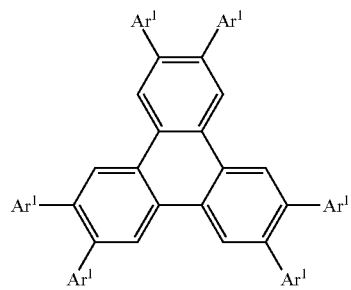

(Tp-2)

(In Formula (Tp-2), each of a plurality of $Ar^1$ is the same, and represents a phenyl group, a fluorenyl group, a naphthyl group or a triphenylenyl group, which may be substituted with an alkyl group, a phenyl group, a fluorenyl group, a naphthyl group or a triphenylenyl group.)

The alkyl group, and the phenyl group, fluorenyl group, naphthyl group or triphenylenyl group, which may be substituted with an alkyl group, a phenyl group, a fluorenyl group, a naphthyl group or a triphenylenyl group, represented by $Ar^1$, have the same meaning as those exemplified in $R^{12}$ to $R^{23}$ and the preferred example is also the same.

According to another aspect of the present invention, the hydrocarbon compound represented by Formula (Tp-1) is preferably a hydrocarbon compound represented by the following Formula (Tp-3).

[Chem. 15]

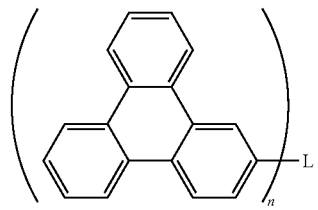

Formula (Tp-3)

(In Formula (Tp-3), L represents a phenyl group, a fluorenyl group, a naphthyl group or a triphenylenyl group, which may be substituted with an alkyl group, a phenyl group, a fluorenyl group, a naphthyl group or a triphenylenyl group, or an n-valent linking group formed by combining these groups. n represents an integer of 1 to 6.)

An alkyl group, and a phenyl group, a fluorenyl group, a naphthyl group or a triphenylenyl group, which form an n-valent linking group, represented by L, have the same meaning as those exemplified as $R^{12}$ to $R^{23}$.

L is preferably a phenyl group or a fluorenyl group, which may be substituted with an alkyl group or a phenyl group, or an n-valent linking group formed by combining these groups.

Hereinafter, preferred embodiments of L will be exemplified, but are not limited thereto. Meanwhile, in the embodiments, * represents a bonding site to a triphenylene ring.

[Chem. 16]

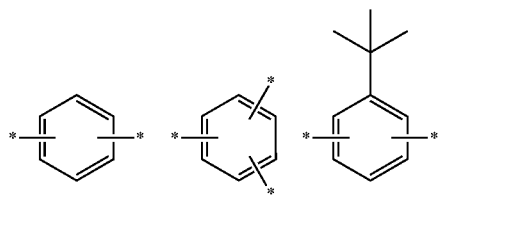

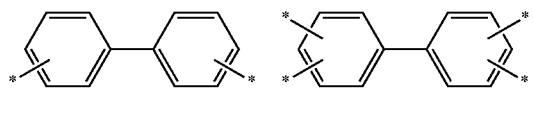

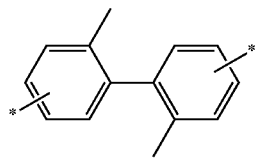

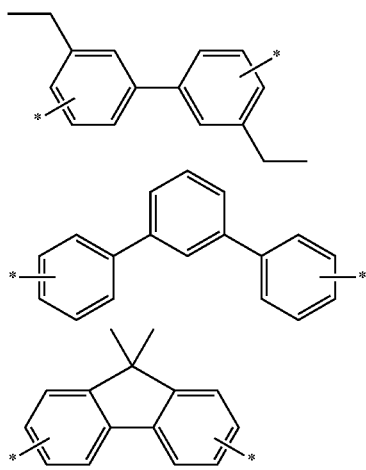

n is preferably 1 to 5, more preferably 1 to 4, and even more preferably 1 or 2.

According to another embodiment of the present invention, the hydrocarbon compound represented by Formula (Tp-1) is preferably a hydrocarbon compound represented by the following Formula (Tp-4).

[Chem. 17]

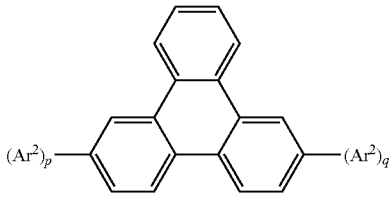

(Tp-4)

(In Formula (Tp-4), when $Ar^2$ is present in plurality, each $Ar^2$ may be the same, and represents an alkyl group, a phenyl group, a naphthyl group, a triphenylenyl group, or a group formed by combining these groups. Each of p and q independently represents 0 or 1, provided that p and q are not 0 at the same time. In the case where p and q represent 0, $Ar^2$ represents a hydrogen atom.)

$Ar^2$ preferably represents a group formed by combining an alkyl group having 1 to 4 carbon atoms, a phenyl group, a naphthyl group and a triphenylenyl group, and more preferably a group formed by combining a methyl group, a t-butyl group, a phenyl group and a triphenylenyl group.

Furthermore, $Ar^2$ preferably represents a phenyl group, and the phenyl group may preferably be substituted with an alkyl group, a phenyl group, fluorenyl group, a naphthyl group, a triphenylenyl group, or a group formed by combining these groups at meta position, and particularly preferably $Ar^1$ represents a phenyl group which may be substituted with an alkyl group having 1 to 4 carbon atoms, a phenyl group, a naphthyl group, a triphenylenyl group, or a group formed by combining the groups at meta position.

In addition, $Ar^2$ is preferably the following group (Arx).

[Chem. 18]

*—$(Ara)_{na}$—$(Arb)_{nb}$—$(Arc)_{nc}$—$(Ard)_{nd}$ (Arx)

(In group (Arx), each of Ara to Ard independently represents a ring selected from a benzene ring, a naphthalene ring, a fluorene ring and a triphenylene ring. Each of na, nb and nc independently represents 0 or 1, and nd represents 1. When na, nb and nc are 0, Ara to Arc represent a single bond. Each of Ara to Ard may be independently substituted with an alkyl group or a phenyl group. * represents a bonding site to the triphenylene ring of Formula (Tp-4).)

In group (Arx), Ara to Ard are preferably a benzene ring, a triphenylene ring, and more preferably a benzene ring.

One to three of na, nb and nc are preferably 1.

According to another embodiment of the present invention, $R^{18}$ of the hydrocarbon compound represented by Formula (Tp-1) is the group (Arx), and $R^{12}$ to $R^{17}$ and $R^{19}$ to $R^{23}$ are preferably hydrogen atoms.

When the hydrocarbon compound according to the present invention is used as a host material of a light emitting layer of an organic electroluminescence device or an electric charge transporting material of a layer adjacent to the light emitting layer, light emission is prevented from being quenched if the energy gap in the state of thin film (when the light emitting material is a phosphorescent light emitting material, the lowest triplet excited state ($T_1$) energy in the state of thin film) is larger than the light emitting material, which is advantageous in improving the efficiency. Meanwhile, from the viewpoint of chemical stability of the compound, it is preferred that the energy gap and $T_1$ energy are not extremely high. The $T_1$ energy of the compound represented by Formula (Tp-1) in the state of film is preferably 2.61 eV (62 kcal/mol) to 3.51 eV (80 kcal/mol), more preferably 2.69 eV (63.5 kcal/mol) to 3.51 eV (75 kcal/mol) and even more preferably 2.76 eV (65 kcal/mol) to 3.51 eV (70 kcal/mol). In particular, when the phosphorescent light emitting material is used as a light emitting material, it is preferred that the $T_1$ energy falls within the range.

The $T_1$ energy may be obtained by measuring a phosphorescence-light emitting spectrum of a thin film of a material and from a short wavelength end thereof. For example, a film having a thickness of about 50 nm is formed by depositing a material by vacuum deposition on a washed quartz glass substrate, and the phosphorescence-light emitting spectrum of the thin film is measured by using an F-7000 Hitachi fluorescence spectrophotometer (Hitachi High-Technologies Corporation.) at liquid nitrogen temperature. The $T_1$ energy may be obtained by converting a rising wavelength on the short wavelength side of the obtained emission spectrum into an energy unit.

From the viewpoint of stably operating the organic electroluminescence device for heat generation when driving at high temperature or during driving the device, the glass transition temperature (Tg) of the hydrocarbon compound according to the present invention is preferably 80° C. to 400° C., more preferably 100° C. to 400° C. and even more preferably 120° C. to 400° C.

Hereinafter, specific examples of the hydrocarbon compound according to the present invention will be exemplified, but the present invention is not limited thereto.

[Chem. 19]

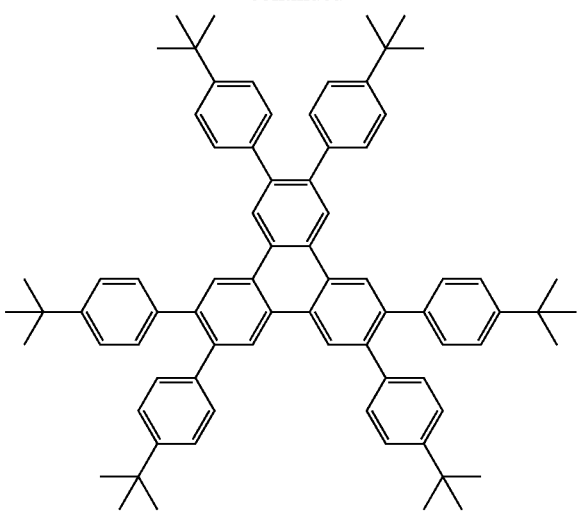

-continued

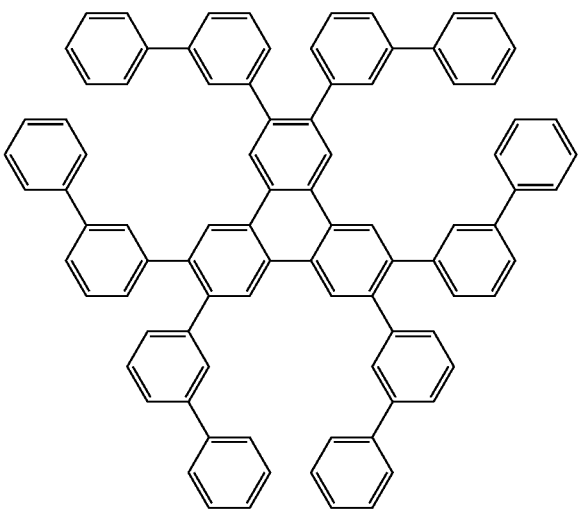

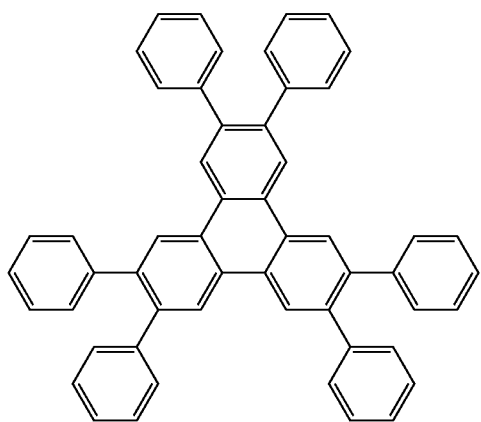

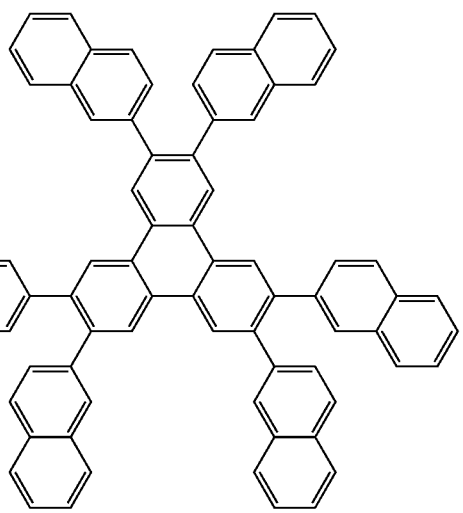

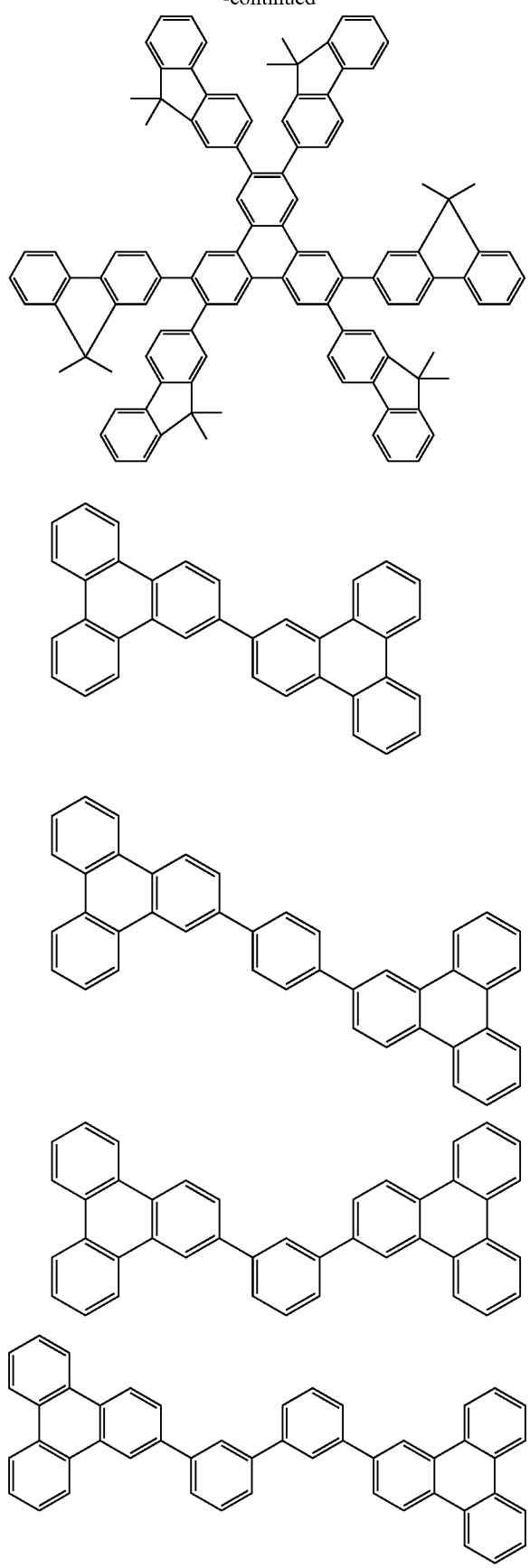
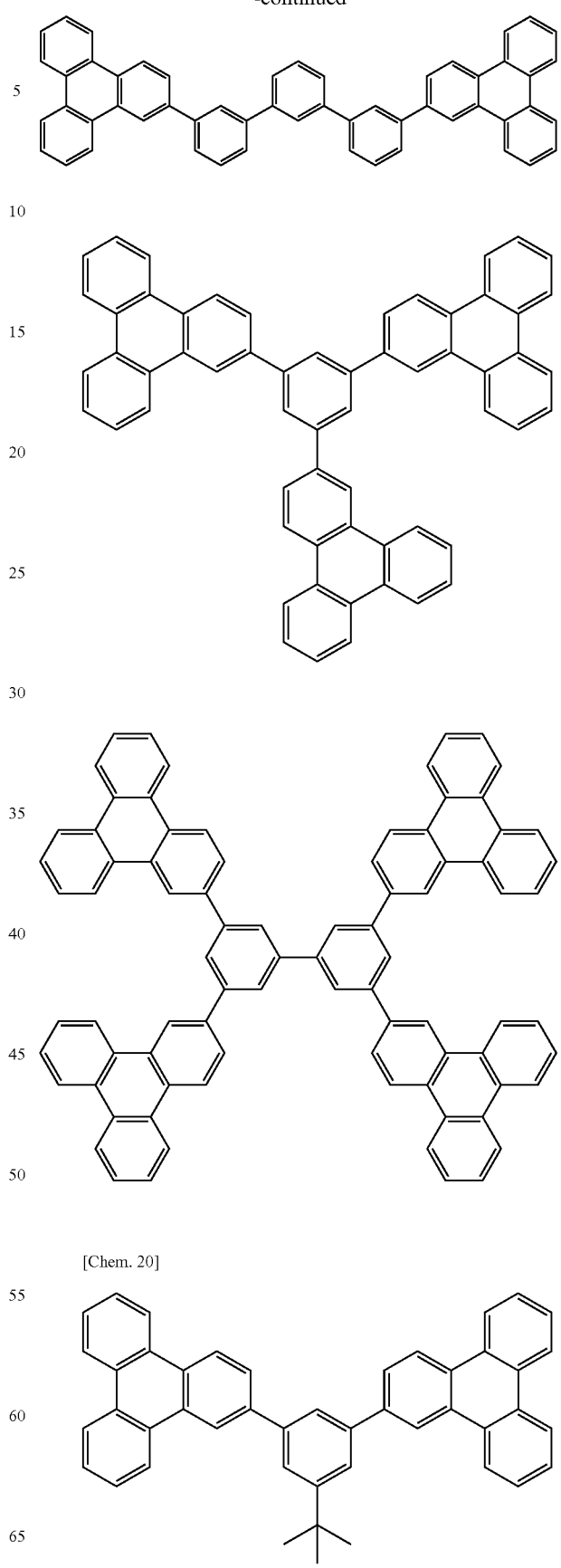
[Chem. 20]

37
-continued
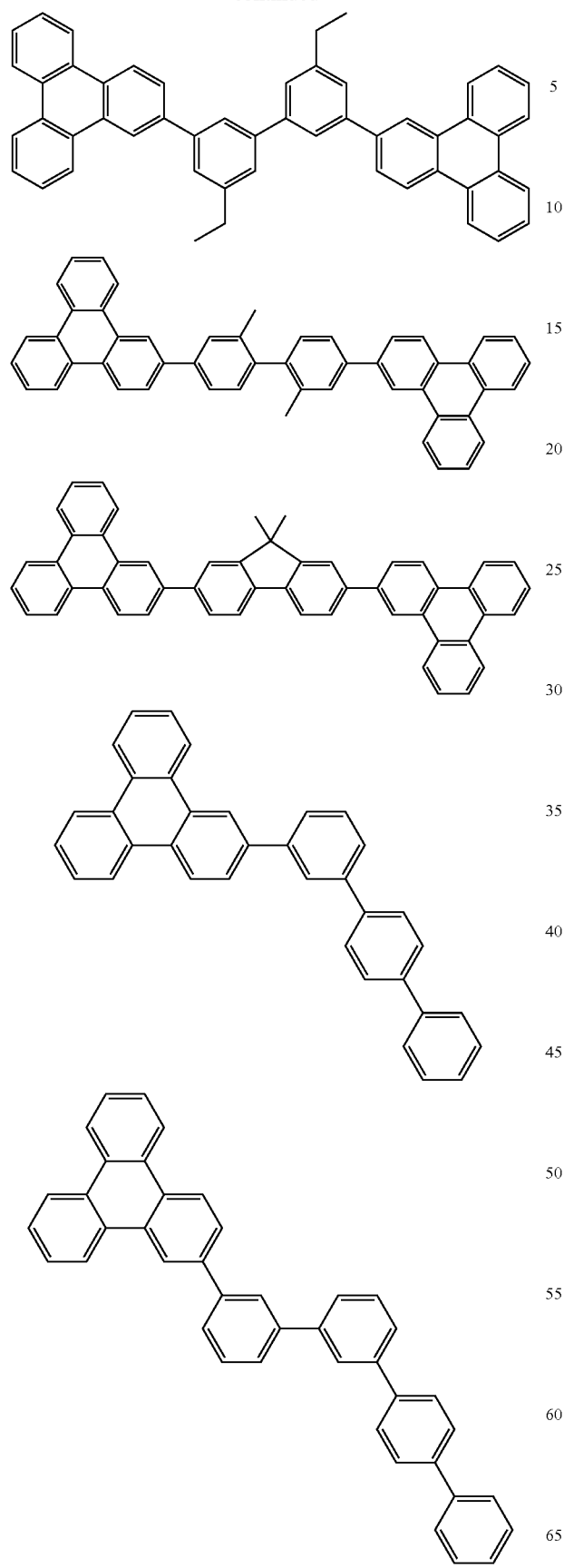
38
-continued
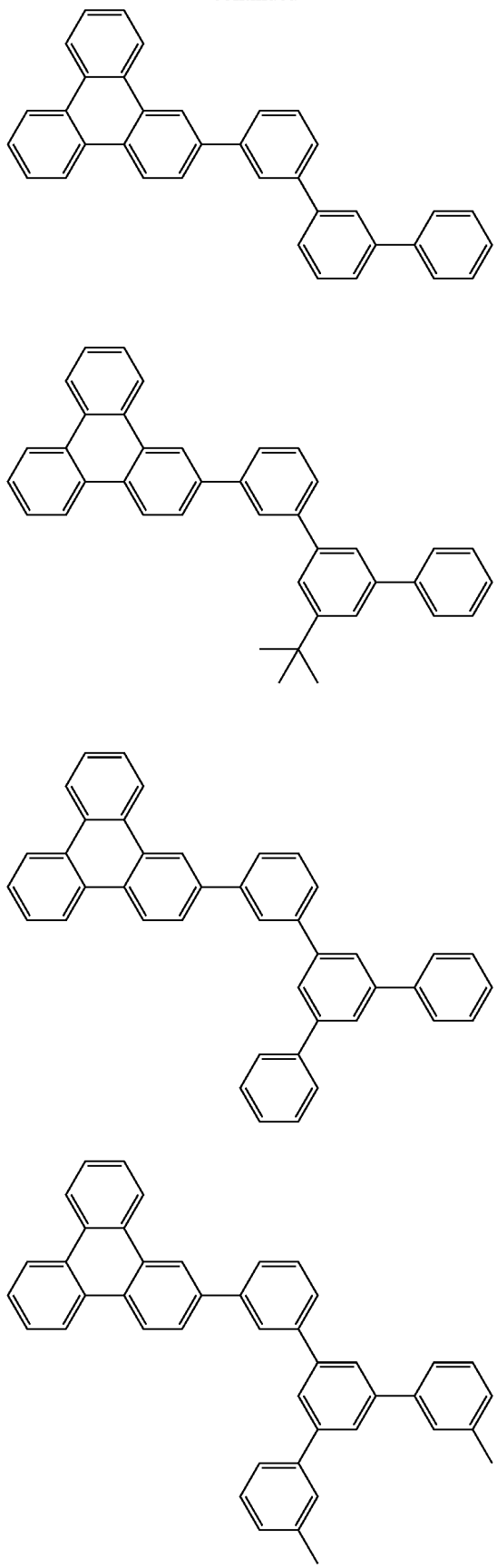

-continued

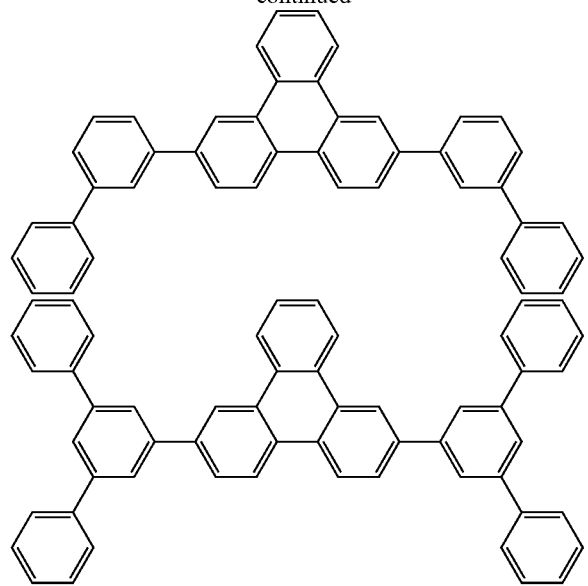

The compound exemplified as the hydrocarbon compound according to the present invention may be synthesized by a method described in International Publication No. WO 05/013388, International Publication No. WO 06/130598, and International Publication No. WO 09/021107.

After the synthesis, it is preferred that purification by column chromatography, recrystallization and the like is performed, and then, purification is performed by sublimation purification. By sublimation purification, organic impurities may be separated, and inorganic salts, residual solvents and the like may be effectively removed.

In the luminescence device of the present invention, the hydrocarbon compound is contained in an organic layer adjacent to a light emitting layer between the light emitting layer and a cathode, the use thereof is not limited, and the compound may be further contained in any layer in the organic layer. As a layer which introduces the hydrocarbon compound according to the present invention, it may be contained in one of a light emitting layer, a hole injection layer, a hole transporting layer, an electron transporting layer, an electron injection layer, an exciton blocking layer, and a charge blocking layer, or a plurality thereof.

The organic layer adjacent to the light emitting layer between the light emitting layer and the cathode, in which the hydrocarbon compound is contained, is preferably a charge blocking layer or an electron transporting layer and, more preferably an electron transporting layer.

[Organic Electroluminescence Device]

The device of the present invention will be described in detail.

The organic electroluminescence device of the present invention is an organic electroluminescence device, including: a pair of electrodes composed of an anode and a cathode; a light emitting layer between the electrodes; and an organic layer which is adjacent to the light emitting layer between the light emitting layer and the cathode, on a substrate, and the light emitting layer contains at least one compound represented by the following Formula (1) and the organic layer adjacent to the light emitting layer contains at least one hydrocarbon compound represented by Formula (Tp-1).

As an embodiment of the luminescence device of the present invention, the organic electroluminescence device is preferred, in which the compound represented by Formula (1) is the compound represented by Formula (2) and the hydrocarbon compound represented by Formula (Tp-1) is the hydrocarbon compound represented by Formula (Tp-2), Formula (Tp-3), or Formula (Tp-4).

In the organic electroluminescence device of the present invention, the light emitting layer is an organic layer, and the device includes at least one layer of an organic layer between the light emitting layer and a cathode, and may further have a plurality of organic layers in addition to having an organic layer which is adjacent to the light emitting layer between the light emitting layer and the cathode.

Due to properties of the luminescence device, at least one electrode of the anode and cathode is preferably transparent or semi-transparent.

FIG. 1 illustrates an example of the configuration of an organic electroluminescence device according to the present invention. In an organic electroluminescence device 10 according to the present invention, which is illustrated in FIG. 1, a light emitting layer 6 is interposed between an anode 3 and a cathode 9 on a supporting substrate 2. Specifically, a hole injection layer 4, a hole transporting layer 5, the light emitting layer 6, a hole blocking layer 7 and an electron transporting layer 8 are stacked in this order between the anode 3 and the cathode 9.

<Configuration of Organic Layer>

The layer configuration of the organic layer is not particularly limited and may be appropriately selected according to the use and purpose of the organic electroluminescence device, but is preferably formed on the transparent electrode or on the rear electrode. In this case, the organic layer is formed on the front surface or one surface on the transparent electrode or the rear electrode.

The shape, size, thickness and the like of the organic layer are not particularly limited and may be appropriately selected according to the purpose.

The specific layer configuration may include the followings, but the present invention is not limited to the configurations.

Anode/hole transporting layer/light emitting layer/electron transporting layer/cathode, Anode/hole transporting layer/light emitting layer/blocking layer/electron transporting layer/cathode, Anode/hole transporting layer/light emitting layer/blocking layer/electron transporting layer/electron injection layer/cathode, Anode/hole injection layer/hole transporting layer/light emitting layer/electron transporting layer/electron injection layer/cathode, Anode/hole injection layer/hole transporting layer/light emitting layer/blocking layer/electron transporting layer/cathode, Anode/hole injection layer/hole transporting layer/light emitting layer/blocking layer/electron transporting layer/electron injection layer/cathode.

The device configuration, substrate, cathode and anode of the organic electroluminescence device are described in detail in, for example, Japanese Patent Application Laid-Open No. 2008-270736, and the subject matters described in the publication may be applied to the present invention.

<Substrate>

It is preferred that the substrate which is used in the present invention is a substrate which does not scatter or decay light generated from the organic layer. It is preferred that an organic material is superior in heat resistance, dimensional stability, solvent resistance, electrical insulation properties and processibility.

<Anode>

Typically, the anode may have a function as an electrode for supplying holes into the organic layer, is not particularly limited with respect to shape, structure, size and the like and may be appropriately selected among the known electrode materials depending upon a use or purpose of the luminescence device. As described above, the anode is usually provided as a transparent anode.

<Cathode>

Typically, the cathode may have a function as an electrode for injecting electrons into the organic layer, is not particularly limited with respect to shape, structure, size and the like and may be appropriately selected among the known electrode materials depending upon a use or purpose of the luminescence device.

With respect to the substrate, the anode and the cathode, subject matters described in paragraph Nos. [0070] to [0089] of Japanese Patent Application Laid-Open No. 2008-270736 may be applied to the present invention.

<Organic Layer>

An organic layer in the present invention will be described.

[Formation of Organic Layer]

In the organic electroluminescence device of the present invention, each organic layer may be appropriately formed by any one of dry film-forming methods such as a vapor deposition method, a sputtering method and the like, and solution application processes such as a transfer method, a printing method, a spin-coat method, a bar-coat method and the like. In the device of the present invention, it is preferred that at least one layer of a light emitting layer, an organic layer adjacent to the light emitting layer and other organic layers present between the anode and the cathode are formed by the solution application process.

[Light Emitting Layer]

The light emitting layer is a layer having functions, at the time of applying an electric field, of accepting a hole from the anode, the hole injection layer or the hole transporting layer and accepting an electron from the cathode, the electron injection layer or the electron transporting layer to provide a site of recombination of the hole and the electron, thereby achieving light emission.

The substrate, the anode, the cathode, the organic layer and the light emitting layer are described in detail, in, for example, Japanese Patent Application Laid-Open No. 2008-270736 and Japanese Patent Application Laid-Open No. 2007-266458, and subject matters described in these publications may be applied to the present invention. Further, a material which does not have a charge transporting property and does not emit light may be included in the light emitting layer.

(Light Emitting Material)

As the light emitting material in the present invention, any of a phosphorescent light emitting material, a fluorescent light emitting material and the like may be used.

The light emitting layer in the present invention may contain two or more of light emitting materials in order to improve color purity or to expand a light emitting wavelength region. At least one of the light emitting materials is preferably a fluorescent light emitting material.

From the viewpoint of driving durability, it is preferred that the light emitting material in the present invention satisfies a relationship of 1.2 eV>$\Delta$Ip>0.2 eV and/or 1.2 eV>$\Delta$Ea>0.2 eV between the host material. Here, $\Delta$Ip means a difference in Ip values of the host material and the light emitting material, $\Delta$Ea means a difference in Ea values of the host material and the light emitting material.

At least one of the light emitting materials is preferably a platinum complex material or an iridium complex material, and more preferably an iridium complex material.

The fluorescent light emitting material and the phosphorescent light emitting material are described in detail, in, for example, paragraph Nos. [0100] to [0164] of Japanese Patent Application Laid-Open No. 2008-270736 and paragraph Nos. [0088] to [0090] of Japanese Patent Application Laid-Open No. 2007-266458, and subject matters described in these publications may be applied to the present invention.

From the viewpoint of light emission efficiency, phosphorescent light emitting materials are preferred. Examples of the phosphorescent light emitting material which may be used in the present invention include phosphorescent light emitting compounds and the like described in patent documents such as U.S. Pat. No. 6,303,238B1, U.S. Pat. No. 6,097,147, WO 00/57676, WO 00/70655, WO 01/08230, WO 01/39234 A2, WO 01/41512 A1, WO 02/02714 A2, WO 02/15645 A1, WO 02/44189 A1, WO 05/19373 A2, Japanese Patent Application Laid-Open No. 2001-247859, Japanese Patent Application Laid-Open No. 2002-302671, Japanese Patent Application Laid-Open No. 2002-117978, Japanese Patent Application Laid-Open No. 2003-133074, Japanese Patent Application Laid-Open No. 2002-235076, Japanese Patent Application Laid-Open No. 2003-123982, Japanese Patent Application Laid-Open No. 2002-170684, EP 1211257, Japanese Patent Application Laid-Open No. 2002-226495, Japanese Patent Application Laid-Open No. 2002-234894, Japanese Patent Application Laid-Open No. 2001-247859, Japanese Patent Application Laid-Open No. 2001-298470, Japanese Patent Application Laid-Open No. 2002-173674, Japanese Patent Application Laid-Open No. 2002-203678, Japanese Patent Application Laid-Open No. 2002-203679, Japanese Patent Application Laid-Open No. 2004-357791, Japanese Patent Application Laid-Open No. 2006-256999, Japanese Patent Application Laid-Open No. 2007-19462, Japanese Patent Application Laid-Open No. 2007-84635, Japanese Patent Application Laid-Open No. 2007-96259 and the like, and among them, further preferred light emitting dopants include an Ir complex, a Pt complex, a Cu complex, a Re complex, a W complex, a Rh complex, a Ru complex, a Pd complex, an Os complex, an Eu complex, a Tb complex, a Gd complex, a Dy complex and a Ce complex. An Ir complex, a Pt complex or a Re complex is particularly preferred, and among them, an Ir complex, a Pt complex, or a Re complex, including at least one coordination mode of a metal-carbon bond, a metal-nitrogen bond, a metal-oxygen bond and a metal-sulfur bond are preferred. Further, from the viewpoint of light emission efficiency, driving durability, chromaticity and the like, an Ir complex and a Pt complex is particularly preferred, and an Ir complex is most preferred.

A platinum complex is preferably a platinum complex represented by the following Formula (C-1).

[Chem. 21]

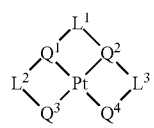

(C-1)

(In the formula, each of $Q^1$, $Q^2$, $Q^3$ and $Q^4$ independently represents a ligand which is coordinated with Pt. Each of $L^1$, $L^2$ and $L^3$ independently represents a single bond or a divalent linking group.)

An explanation as for Formula (C-1) is described. Each of $Q^1$, $Q^2$, $Q^3$ and $Q^4$ independently represents a ligand which is coordinated with Pt. At that time, the bond of each of $Q^1$, $Q^2$, $Q^3$ and $Q^4$ to Pt may be any of a covalent bond, an ionic bond, a coordination bond and the like. As an atom bound to Pt in each of $Q^1$, $Q^2$, $Q^3$ and $Q^4$, a carbon atom, a nitrogen atom, an oxygen atom, a sulfur atom and a phosphorus atom are preferred. Among the atoms bound to Pt in $Q^1$, $Q^2$, $Q^3$ and $Q^4$, it is preferred that at least one of the atoms is a carbon atom; it is more preferred that two of the atoms are a carbon atom; and it is particularly preferred that two of the atoms are a carbon atom and the other two are a nitrogen atom.

As $Q^1$, $Q^2$, $Q^3$ and $Q^4$ bound to Pt with a carbon atom, any of an anionic ligand and a neutral ligand may be used, and examples of the anionic ligand include a vinyl ligand, an aromatic hydrocarbon ring ligand (for example, a benzene ligand, a naphthalene ligand, an anthracene ligand, a phenanthrene ligand, and the like), a heterocyclic ligand (for example, a furan ligand, a thiophene ligand, a pyridine ligand, a pyrazine ligand, a pyrimidine ligand, a pyridazine ligand, a triazine ligand, a thiazole ligand, an oxazole ligand, a pyrrole ligand, an imidazole ligand, a pyrazole ligand, a triazole ligand and condensed ring bodies including the same (for example, a quinoline ligand, a benzothiazole ligand, and the like)). Examples of the neutral ligand include a carbene ligand.

As $Q^1$, $Q^2$, $Q^3$ and $Q^4$ bound to Pt with a nitrogen atom, any of a neutral ligand and an anionic ligand may be used, and examples of the neutral ligand include a nitrogen-containing aromatic heterocyclic ligand (a pyridine ligand, a pyrazine ligand, a pyrimidine ligand, a pyridazine ligand, a triazine ligand, an imidazole ligand, a pyrazole ligand, a triazole ligand, an oxazole ligand, a thiazole ligand, and condensed ring bodies including the same (for example, a quinoline ligand, a benzoimidazole ligand, and the like)), an amine ligand, a nitrile ligand and an imine ligand. Examples of the anionic ligand include an amino ligand, an imino ligand and a nitrogen-containing aromatic heterocyclic ligand (a pyrrole ligand, an imidazole ligand, a triazole ligand, and condensed ring bodies including the same (for example, an indole ligand, a benzoimidazole ligand and the like)).

As $Q^1$, $Q^2$, $Q^3$ and $Q^4$ bound to Pt with an oxygen atom, any of a neutral ligand and an anionic ligand may be used, and examples of the neutral ligand include an ether ligand, a ketone ligand, an ester ligand, an amide ligand and an oxygen-containing heterocyclic ligand (a furan ligand, an oxazole ligand and condensed ring bodies including the same (a benzoxazole ligand and the like)). Examples of the anionic ligand include an alkoxy ligand, an aryloxy ligand, a heteroaryloxy ligand, an acyloxy ligand, a silyloxy ligand and the like.

As $Q^1$, $Q^2$, $Q^3$ and $Q^4$ bound to Pt with a sulfur atom, any of a neutral ligand and an anionic ligand may be used, and examples of the neutral ligand include a thioether ligand, a thioketone ligand, a thioester ligand, a thioamide ligand and a sulfur-containing heterocyclic ligand (a thiophene ligand, a thiazole ligand and condensed ring bodies (a benzothiazole ligand and the like)). Examples of the anionic ligand include an alkyl mercapto ligand, an aryl mercapto ligand, a heteroaryl mercapto ligand and the like.

As $Q^1$, $Q^2$, $Q^3$ and $Q^4$ bound to Pt with a phosphorus atom, any of a neutral ligand and an anionic ligand may be used, and examples of the neutral ligand include a phosphine ligand, a phosphoric acid ester ligand, a phosphorous acid ester ligand and a phosphorus-containing heterocyclic ligand (a phosphinine ligand and the like), and examples of the anionic ligand include a phosphino ligand, a phosphinyl ligand, a phosphoryl ligand and the like.

The group represented by $Q^1$, $Q^2$, $Q^3$ and $Q^4$ may have a substituent, and as the substituent, those exemplified above for the group A of substituents may be appropriately applied. In addition, the substituents may be linked to each other (when $Q^3$ and $Q^4$ are linked to each other, a Pt complex of a cyclic tetradentate ligand is formed).

The group represented by $Q^1$, $Q^2$, $Q^3$ and $Q^4$ is preferably an aromatic hydrocarbon ring ligand bound to Pt with a carbon atom, an aromatic heterocyclic ligand bound to Pt with a carbon atom, a nitrogen-containing aromatic heterocyclic ligand bound to Pt with a nitrogen atom, an acyloxy ligand, an alkyloxy ligand, an aryloxy ligand, a heteroaryloxy ligand and a silyloxy ligand, more preferably an aromatic hydrocarbon ring ligand bound to Pt with a carbon atom, an aromatic heterocyclic ligand bound to Pt with a carbon atom, a nitrogen-containing aromatic heterocyclic ligand bound to Pt with a nitrogen atom, an acyloxy ligand and an aryloxy ligand, and even more preferably an aromatic hydrocarbon ring ligand bound to Pt with a carbon atom, an aromatic heterocyclic ligand bound to Pt with a carbon atom, a nitrogen-containing aromatic heterocyclic ligand bound to Pt with a nitrogen atom and an acyloxy ligand.

$L^1$, $L^2$ and $L^3$ represent a single bond or a divalent linking group. Examples of the divalent linking group represented by $L^1$, $L^2$ and $L^3$ include an alkylene group (methylene, ethylene, propylene and the like), an arylene group (phenylene and naphthalenediyl), a heteroarylene group (pyridinediyl, thiophenediyl and the like), an imino group (—NR—) (a phenylimino group and the like), an oxy group (—O—), a thio group (—S—), a phosphinidene group (—PR—) (a phenylphosphinidene group and the like), a silylene group (—SiRR'—) (a dimethylsilylene group, a diphenylsilylene group and the like) or a combination thereof. Here, each of R and R' independently represents an alkyl group, an aryl group and the like. These linking groups may further have a substituent.

From the viewpoint of stability and light emission quantum yield of the complex, $L^1$, $L^2$ and $L^3$ are preferably a single bond, an alkylene group, an arylene group, a heteroarylene group, an imino group, an oxy group, a thio group and a silylene group, more preferably a single bond, an alkylene group, an arylene group and an imino group, further preferably a single bond, an alkylene group and an arylene group, even further preferably a single bond, a methylene group and a phenylene group, even more preferably a single bond and a di-substituted methylene group, even still further preferably a single bond, a dimethylmethylene group, a diethylmethylene group, a diisobutylmethylene group, a dibenzylmethylene group, an ethylmethylmethylene group, a methylpropylmethylene group, an isobutylmethylmethylene group, a diphenylmethylene group, a methylphenylmethylene group, a cyclohexanediyl group, a cyclopentanediyl group, a fluorenediyl group and a fluoromethylmethylene group.

$L^1$ is particularly preferably a dimethylmethylene group, a diphenylmethylene group and a cyclohexanediyl group, and most preferably a dimethylmethylene group.

$L^2$ and $L^3$ are most preferably a single bond.

A platinum complex represented by Formula (C-1) is more preferably a platinum complex represented by the following Formula (C-2).

[Chem. 22]

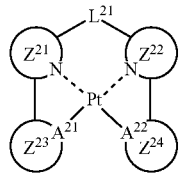

Formula (C-2)

(In the formula, $L^{21}$ represents a single bond or a divalent linking group. Each of $A^{21}$ and $A^{22}$ independently represents a carbon atom or a nitrogen atom. Each of $Z^{21}$ and $Z^{22}$ independently represents a nitrogen-containing aromatic heterocyclic ring. Each of $Z^{23}$ and $Z^{24}$ independently represents a benzene ring or an aromatic heterocyclic ring.)

An explanation as for Formula (C-2) is described. $L^{21}$ has the same meaning as $L^1$ in Formula (C-1), and preferred ranges thereof are also the same.

Each of $A^{21}$ and $A^{22}$ independently represents a carbon atom or a nitrogen atom. It is preferred that at least one of $A^{21}$ and $A^{22}$ is a carbon atom, and from the viewpoint of stability of the complex and the viewpoint of light emission quantum yield of the complex, it is preferred that both $A^{21}$ and $A^{22}$ are a carbon atom.

Each of $Z^{21}$ and $Z^{22}$ independently represents a nitrogen-containing aromatic heterocyclic ring. Examples of the nitrogen-containing aromatic heterocyclic ring represented by $Z^{21}$ and $Z^{22}$ include a pyridine ring, a pyrimidine ring, a pyrazine ring, a triazine ring, an imidazole ring, a pyrazole ring, an oxazole ring, a thiazole ring, a triazole ring, an oxadiazole ring, a thiadiazole ring and the like. From the viewpoint of stability of the complex, control of light emission wavelength, and light emission quantum yield, the ring represented by $Z^{21}$ and $Z^{22}$ is preferably a pyridine ring, a pyrazine ring, an imidazole ring and a pyrazole ring, more preferably a pyridine ring, an imidazole ring and a pyrazole ring, even more preferably a pyridine ring and a pyrazole ring, and particularly preferably a pyridine ring.

The nitrogen-containing aromatic heterocyclic ring represented by $Z^{21}$ and $Z^{22}$ may have a substituent, and as the substituent on the carbon atom, the group A of substituents may be applied, and as the substituent on the nitrogen atom, the group B of substituents may be applied. The substituent on the carbon atom is preferably an alkyl group, a perfluoroalkyl group, an aryl group, an aromatic heterocyclic group, a dialkylamino group, a diarylamino group, an alkoxy group, a cyano group and a fluorine atom. Although the substituent is appropriately selected for the purpose of controlling the light emission wavelength or potential, in the case of making the wavelength short, the substituent is preferably an electron-donating group, a fluorine atom and an aromatic ring group, and for example, an alkyl group, a dialkylamino group, an alkoxy group, a fluorine atom, an aryl group, an aromatic heterocyclic group and the like are selected. Furthermore, in the case of making the wavelength long, the substituent is preferably an electron-withdrawing group, and for example, a cyano group, a perfluoroalkyl group and the like are selected. The substituent on the nitrogen atom is preferably an alkyl group, an aryl group and an aromatic heterocyclic group, and from the viewpoint of stability of the complex, an alkyl group and an aryl group are preferred. The substituents may be linked to each other to form a condensed ring, and examples of the ring to be formed include a benzene ring, a pyridine ring, a pyrazine ring, a pyridazine ring, a pyrimidine ring, an imidazole ring, an oxazole ring, a thiazole ring, a pyrazole ring, a thiophene ring, a furan ring and the like.

Each of $Z^{23}$ and $Z^{24}$ independently represents a benzene ring or an aromatic heterocyclic ring. Examples of the nitrogen-containing aromatic heterocyclic ring represented by $Z^{23}$ and $Z^{24}$ include a pyridine ring, a pyrimidine ring, a pyrazine ring, a pyridazine ring, a triazine ring, an imidazole ring, a pyrazole ring, an oxazole ring, a thiazole ring, a triazole ring, an oxadiazole ring, a thiadiazole ring, a thiophene ring, a furan ring and the like. From the viewpoint of stability of the complex, control of light emission wavelength, and light emission quantum yield, the ring represented by $Z^{23}$ and $Z^{24}$ is preferably a benzene ring, a pyridine ring, a pyrazine ring, an imidazole ring, a pyrazole ring and a thiophene ring, more preferably a benzene ring, a pyridine ring and a pyrazole ring, and even more preferably a benzene ring and a pyridine ring.

The benzene ring and nitrogen-containing aromatic heterocyclic ring represented by $Z^{23}$ and $Z^{24}$ may have a substituent, and as the substituent on the carbon atom, the group A of substituents may be applied, and as the substituent on the nitrogen atom, the group B of substituents may be applied. The substituent on the carbon is preferably an alkyl group, a perfluoroalkyl group, an aryl group, an aromatic heterocyclic group, a dialkylamino group, a diarylamino group, an alkoxy group, a cyano group and a fluorine atom. Although the substituent is appropriately selected for the purpose of controlling the light emission wavelength or potential, in the case of making the wavelength long, the substituent is preferably an electron-donating group and an aromatic ring group, and for example, an alkyl group, a dialkylamino group, an alkoxy group, an aryl group, an aromatic heterocyclic group and the like are selected. Further, in the case of making the wavelength short, the substituent is preferably an electron-withdrawing group, and for example, a fluorine atom, a cyano group, a perfluoroalkyl group and the like are selected. The substituent on the nitrogen atom is preferably an alkyl group, an aryl group and an aromatic heterocyclic group, and from the viewpoint of stability of the complex, an alkyl group and an aryl group are preferred. The substituents may be linked to each other to form a condensed ring, and examples of the ring to be formed include a benzene ring, a pyridine ring, a pyrazine ring, a pyridazine ring, a pyrimidine ring, an imidazole ring, an oxazole ring, a thiazole ring, a pyrazole ring, a thiophene ring, a furan ring and the like.

Among platinum complexes represented by Formula (C-2), one of more preferred embodiments is a platinum complex represented by the following Formula (C-4).

[Chem. 23]

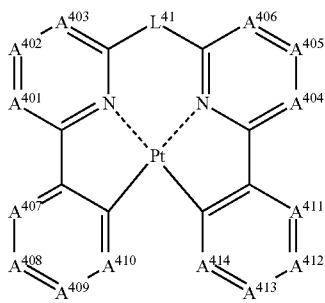

Formula (C-4)

(In Formula (C-4), each of $A^{401}$ to $A^{414}$ independently represents C—R or a nitrogen atom. R represents a hydrogen atom or a substituent. $L^{41}$ represents a single bond or a divalent linking group.)

An explanation as for Formula (C-4) is described.

Each of $A^{401}$ to $A^{414}$ independently represents C—R or a nitrogen atom. R represents a hydrogen atom or a substituent.

As the substituent represented by R, those exemplified above for the group A of substituents may be applied.

$A^{401}$ to $A^{406}$ are preferably C—R, and Rs may be linked to each other to form a ring. When $A^{401}$ to $A^{406}$ are C—R, the R's of $A^{402}$ and $A^{405}$ are preferably a hydrogen atom, an alkyl group, an aryl group, an amino group, an alkoxy group, an aryloxy group, a fluorine atom and a cyano group, more preferably a hydrogen atom, an amino group, an alkoxy group, an aryloxy group and a fluorine atom, and particularly preferably a hydrogen atom and a fluorine atom. The R's of $A^{401}$, $A^{403}$, $A^{404}$ and $A^{406}$ are preferably a hydrogen atom, an alkyl group, an aryl group, an amino group, an alkoxy group, an aryloxy group, a fluorine atom and a cyano group, more preferably a hydrogen atom, an amino group, an alkoxy group, an aryloxy group and a fluorine atom, and particularly preferably a hydrogen atom.

$L^{41}$ has the same meaning as $L^1$ in Formula (C-1), and preferred ranges thereof are also the same.

For $A^{407}$ to $A^{414}$, the number of N (nitrogen atom) in each of $A^{407}$ to $A^{410}$ and $A^{411}$ to $A^{414}$ is preferably 0 to 2, and more preferably 0 or 1. When the light emission wavelength is shifted to the short wavelength side, any of $A^{408}$ and $A^{412}$ is preferably a nitrogen atom, and both $A^{408}$ and $A^{412}$ are more preferably a nitrogen atom.

When $A^{407}$ to $A^{414}$ represent C—R, the R's of $A^{408}$ and $A^{412}$ are preferably a hydrogen atom, an alkyl group, a perfluoroalkyl group, an aryl group, an amino group, an alkoxy group, an aryloxy group, a fluorine atom and a cyano group, more preferably a hydrogen atom, a perfluoroalkyl group, an alkyl group, an aryl group, a fluorine atom and a cyano group, and particularly preferably a hydrogen atom, a phenyl group, a perfluoroalkyl group and a cyano group. The R's of $A^{407}$, $A^{409}$, $A^{411}$, and $A^{413}$ are preferably a hydrogen atom, an alkyl group, a perfluoroalkyl group, an aryl group, an amino group, an alkoxy group, an aryloxy group, a fluorine atom and a cyano group, more preferably a hydrogen atom, a perfluoroalkyl group, a fluorine atom and a cyano group, and particularly preferably a hydrogen atom, a phenyl group and a fluorine atom. The R's of $A^{410}$ and $A^{414}$ are preferably a hydrogen atom and a fluorine atom, and more preferably a hydrogen atom. When any one of $A^{407}$ to $A^{409}$ and $A^{411}$ to $A^{413}$ represents C—R, R's may be linked to each other to form a ring.

Among platinum complexes represented by Formula (C-2), one of more preferred embodiments is a platinum complex represented by the following Formula (C-5).

[Chem. 24]

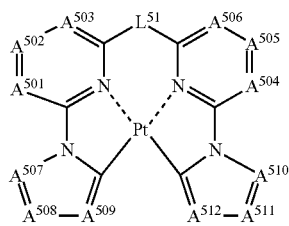

(C-5)

(In Formula (C-5), each of $A^{501}$ to $A^{512}$ independently represents C—R or a nitrogen atom. R represents a hydrogen atom or a substituent. $L^{51}$ represents a single bond or a divalent linking group.)

An explanation as for Formula (C-5) is described. $A^{501}$ to $A^{506}$ and $L^{51}$ have the same meaning as $A^{401}$ to $A^{406}$ and $L^{41}$ in Formula (C-4), and preferred ranges thereof are also the same.

Each of $A^{507}$, $A^{508}$ and $A^{509}$ and $A^{510}$, $A^{511}$ and $A^{512}$ independently represents C—R or a nitrogen atom. R represents a hydrogen atom or a substituent. As the substituent represented by R, those exemplified above for the group A of substituents may be applied. When $A^{507}$, $A^{508}$ and $A^{509}$ and $A^{510}$, $A^{511}$ and $A^{512}$ are C—R, R is preferably a hydrogen atom, an alkyl group, a perfluoroalkyl group, an aryl group, an aromatic heterocyclic group, a dialkylamino group, a diarylamino group, an alkyloxy group, a cyano group and a fluorine atom, more preferably a hydrogen atom, an alkyl group, a perfluoroalkyl group, an aryl group, a dialkylamino group, a cyano group and a fluorine atom, and even more preferably a hydrogen atom, an alkyl group, a trifluoromethyl group and a fluorine atom. In addition, the possible case is that substituents may be linked to each other to form a condensed ring structure. At least one of $A^{507}$, $A^{508}$ and $A^{509}$ and $A^{510}$, $A^{511}$ and $A^{512}$ is preferably a nitrogen atom and $A^{510}$ or $A^{507}$ is particularly preferably a nitrogen atom.

Among platinum complexes represented by Formula (C-1), another more preferred embodiment is a platinum complex represented by the following Formula (C-6).

[Chem. 25]

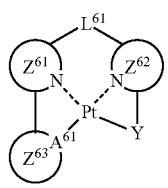

Formula (C-6)

(In the formula, $L^{61}$ represents a single bond or a divalent linking group. Each of $A^{61}$ independently represents a carbon atom or a nitrogen atom. Each of $Z^{61}$ and $Z^{62}$ independently represents a nitrogen-containing aromatic heterocyclic ring. Each of $Z^{63}$ independently represents a benzene ring or an aromatic heterocyclic ring. Y is an anionic non-cyclic ligand bound to Pt.)

An explanation as for Formula (C-6) is described. $L^{61}$ has the same meaning as $L^1$ in Formula (C-1), and preferred ranges thereof are also the same.

$A^{61}$ represents a carbon atom or a nitrogen atom. From the viewpoint of stability of the complex and the viewpoint of light emission quantum yield of the complex, $A^{61}$ is preferably a carbon atom.

Each of $Z^{61}$ and $Z^{62}$ has the same meaning as $Z^{21}$ and $Z^{22}$ in Formula (C-2), respectively, and preferred ranges thereof are also the same. $Z^{63}$ has the same meaning as $Z^{23}$ in Formula (C-2), and preferred ranges thereof are also the same.

Y is an anionic non-cyclic ligand bound to Pt. The non-cyclic ligand is one in which an atom bound to Pt does not form a ring in a ligand state. The atom bound to Pt in Y is preferably a carbon atom, a nitrogen atom, an oxygen atom and a sulfur atom, more preferably a nitrogen atom and an oxygen atom, and most preferably an oxygen atom.

Examples of Y bound to Pt with a carbon atom include a vinyl ligand. Examples of Y bound to Pt with a nitrogen atom include an amino ligand and an imino ligand. Examples of Y bound to Pt with an oxygen atom include an alkoxy ligand, an aryloxy ligand, a heteroaryloxy ligand, an acyloxy ligand, a silyloxy ligand, a carboxyl ligand, a phosphoric acid ligand, a sulfonic acid ligand and the like. Examples of Y bound to Pt with a sulfur atom include an alkyl mercapto ligand, an aryl mercapto ligand, a heteroaryl mercapto ligand, a thiocarboxylate ligand and the like.

The ligand represented by Y may have a substituent, and as the substituent, those exemplified above for the group A of substituents may be appropriately applied. Furthermore, the substituents may be linked to each other.

The ligand represented by Y is preferably a ligand bound to Pt with an oxygen atom, more preferably an acyloxy ligand, an alkyloxy ligand, an aryloxy ligand, a heteroaryloxy ligand and a silyloxy ligand, and even more preferably an acyloxy ligand.

Among platinum complexes represented by Formula (C-6), a more preferred embodiment is a platinum complex represented by the following Formula (C-7).

[Chem. 26]

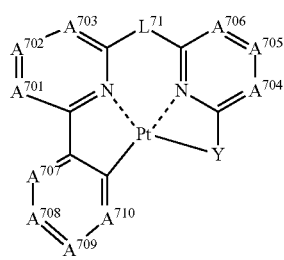

Formula (C-7)

(In the formula, each of $A^{701}$ to $A^{710}$ independently represents C—R or a nitrogen atom. R represents a hydrogen atom or a substituent. $L^{71}$ represents a single bond or a divalent linking group. Y is an anionic non-cyclic ligand bound to Pt.)

An explanation as for Formula (C-7) is described. $L^{71}$ has the same meaning as $L^{61}$ in Formula (C-6), and preferred ranges thereof are also the same. $A^{701}$ to $A^{710}$ have the same meaning as $A^{401}$ to $A^{410}$ in Formula (C-4), and preferred ranges thereof are also the same. Y has the same meaning as that in Formula (C-6), and preferred ranges thereof are also the same.

Specific examples of the platinum complex represented by Formula (C-1) include compounds disclosed in [0143] to [0152], [0157] to [0158] and [0162] to [0168] of Japanese Patent Application Laid-Open No. 2005-310733, compounds disclosed in [0065] to [0083] of Japanese Patent Application Laid-Open No. 2006-256999, compounds disclosed in [0065] to of Japanese Patent Application Laid-Open No. 2006-93542, compounds disclosed in [0063] to [0071] of Japanese Patent Application Laid-Open No. 2007-73891, compounds disclosed in [0079] to [0083] of Japanese Patent Application Laid-Open No. 2007-324309, compounds disclosed in [0065] to [0090] of Japanese Patent Application Laid-Open No. 2006-93542, compounds disclosed in [0055] to [0071] of Japanese Patent Application Laid-Open No. 2007-96255 and compounds disclosed in [0043] to [0046] of Japanese Patent Application Laid-Open No. 2006-313796, and other platinum complexes exemplified below.

[Chem. 27]

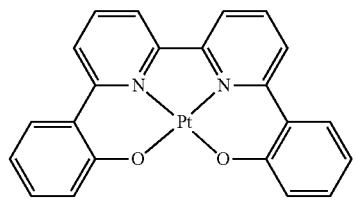

1-1

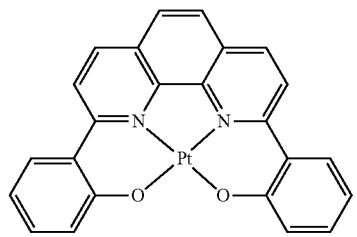

1-2

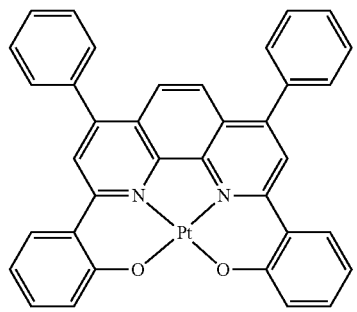

1-3

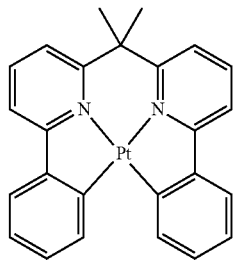

2-0

-continued
2-1
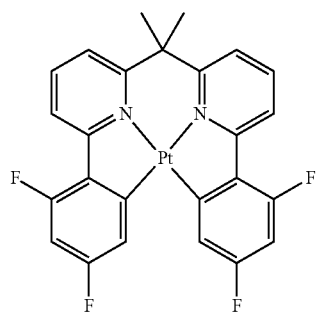
2-2
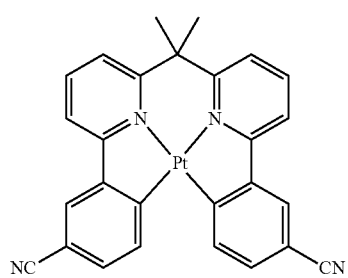
2-3
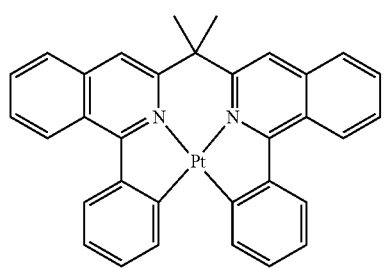
2-4
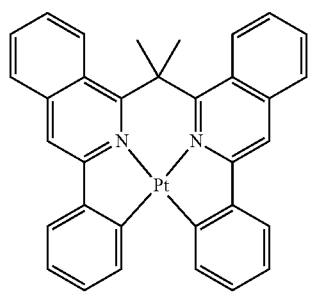
2-5
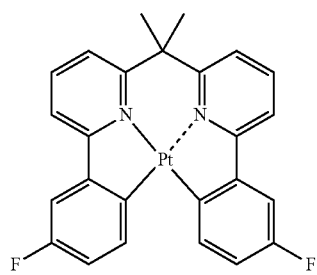
-continued
2-6
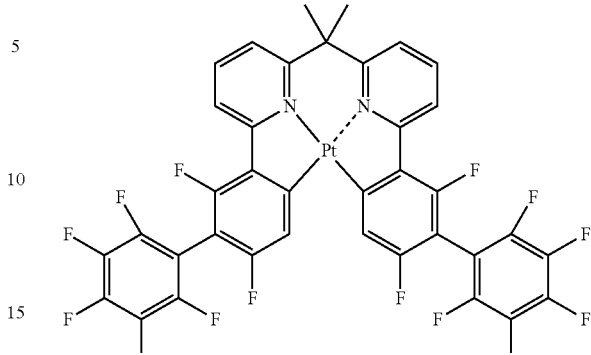
2-7
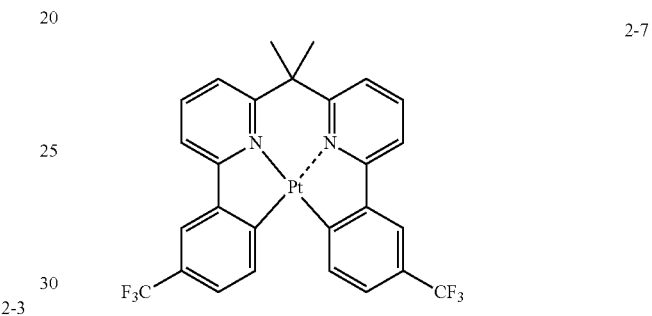
2-8
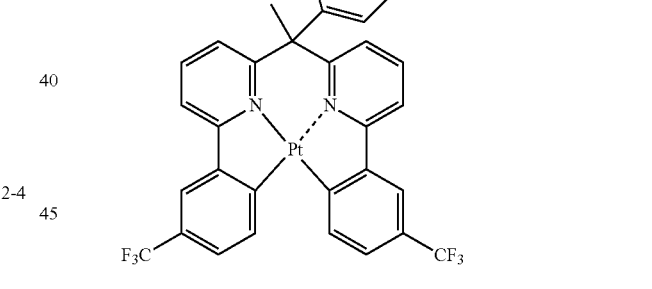
2-9
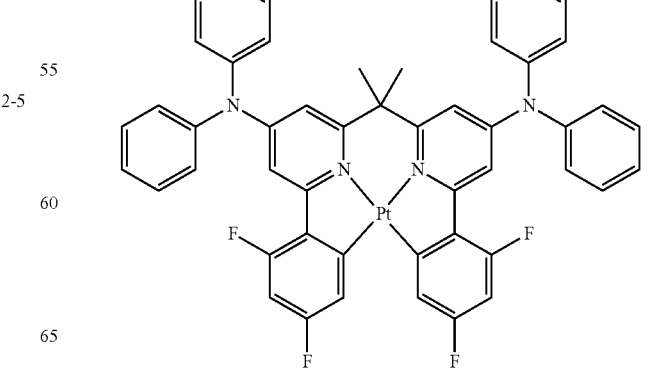

2-10
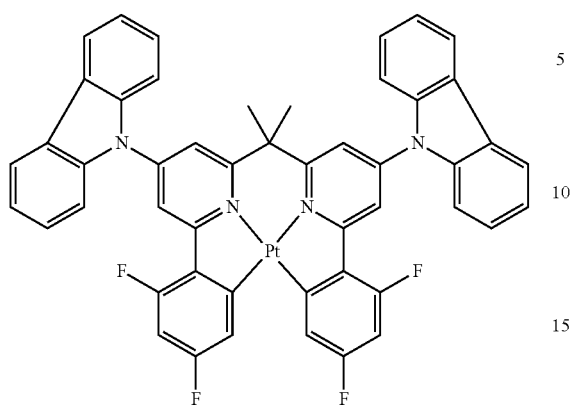
2-11
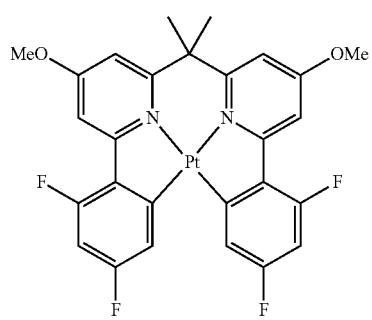
2-12
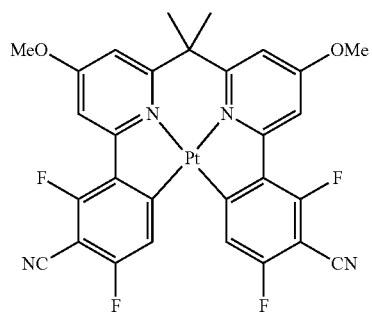
3-1
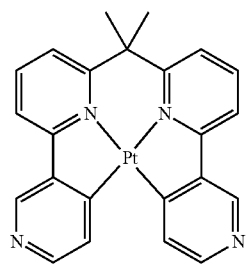
3-2
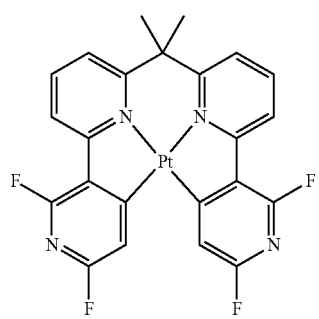
3-3
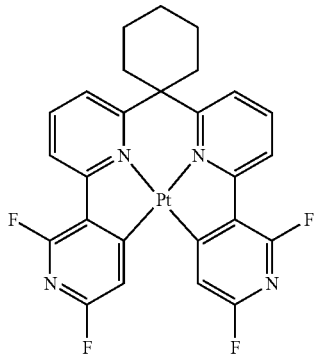
3-4
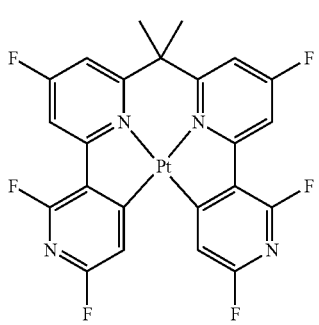
3-5
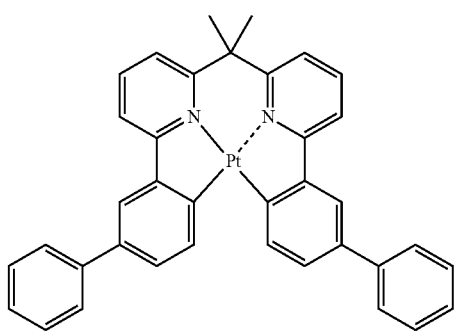
[Chem. 28]
4-1
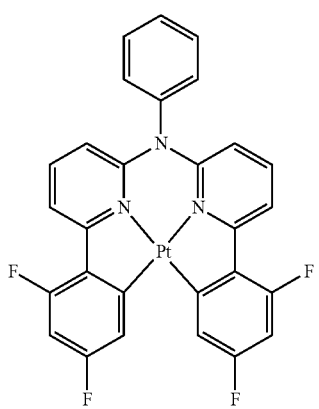

-continued
4-2
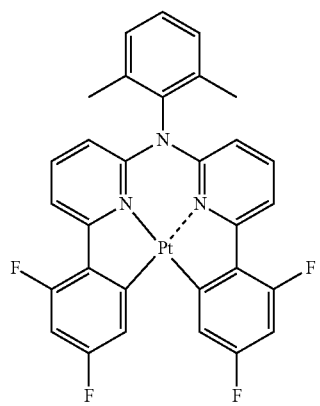
5-1
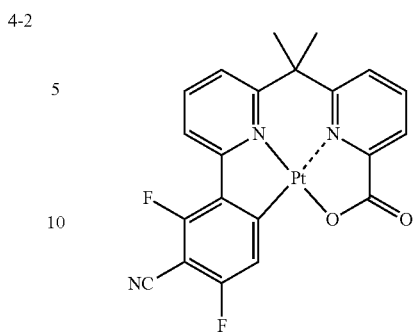
4-3
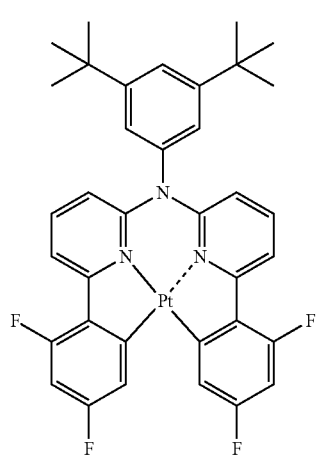
5-2
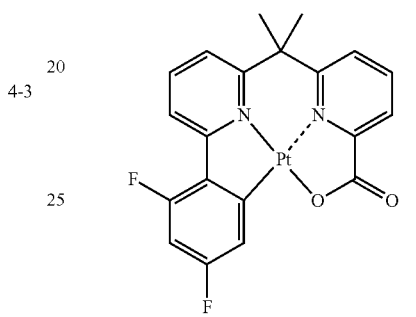
5-3
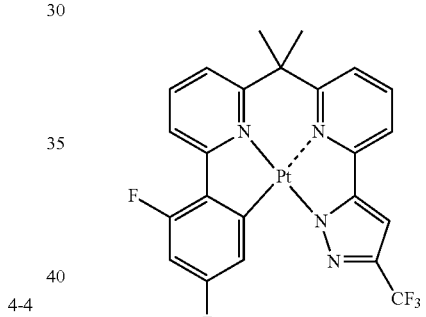
4-4
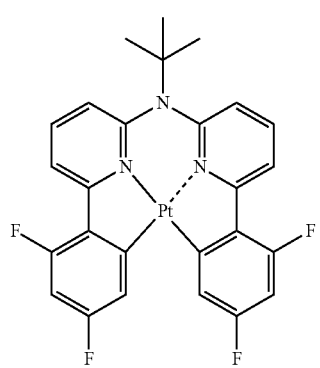
5-5
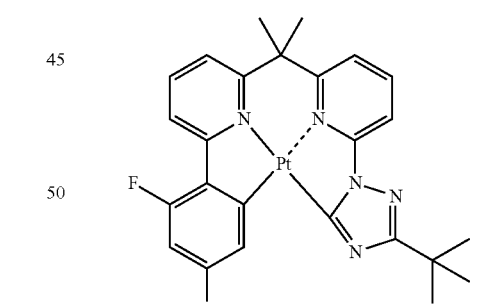
4-5
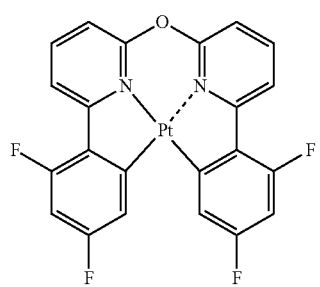
6-1
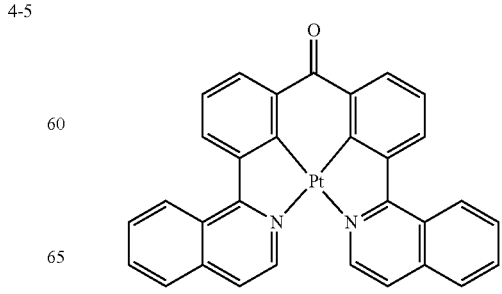

6-2
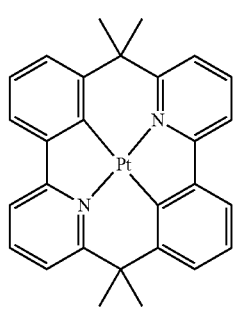
6-3
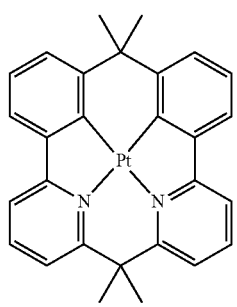
6-4
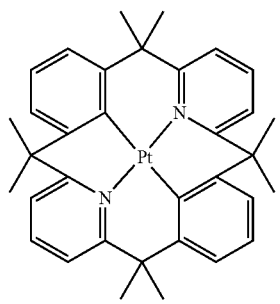
6-6
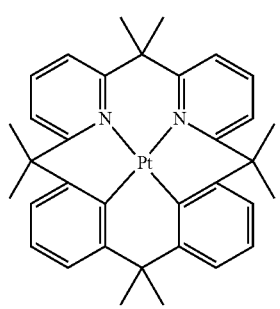
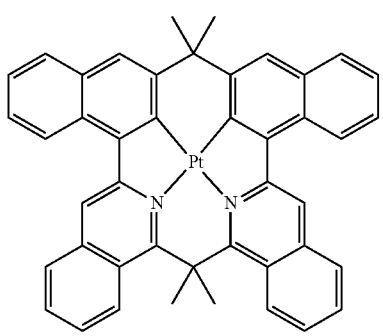
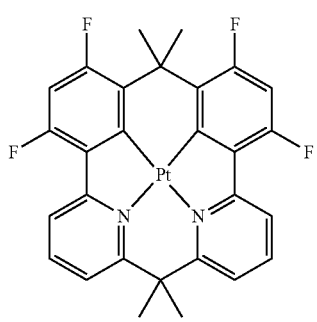
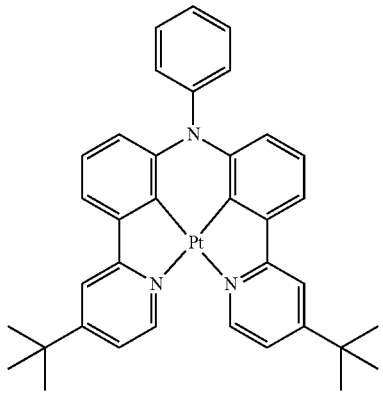
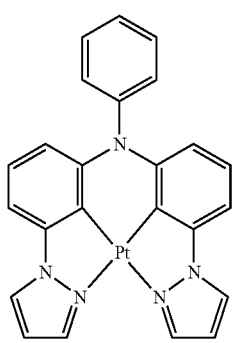
7-1
7-2
7-3
7-4
7-5
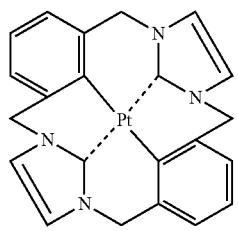

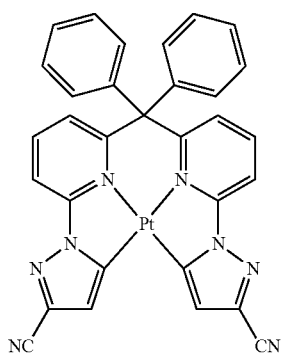
8-1
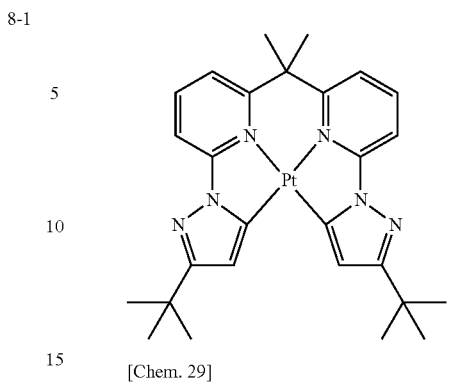
8-5
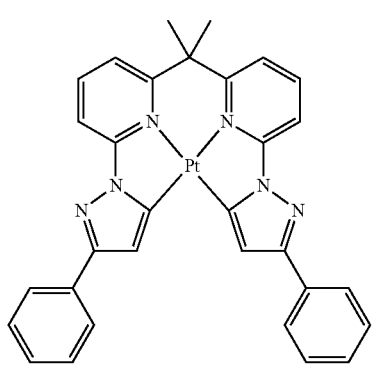
8-2
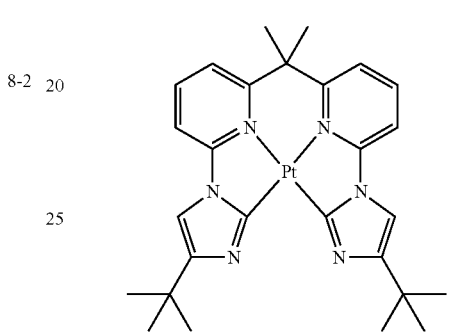
8-6
[Chem. 29]
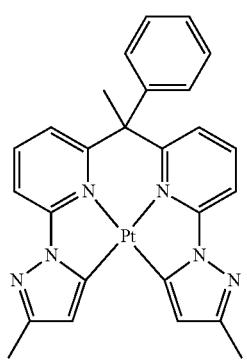
8-3
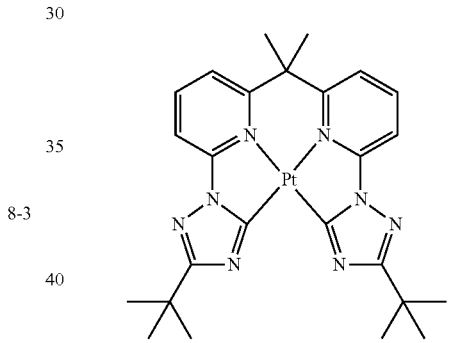
8-8
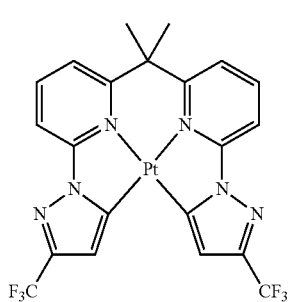
8-4
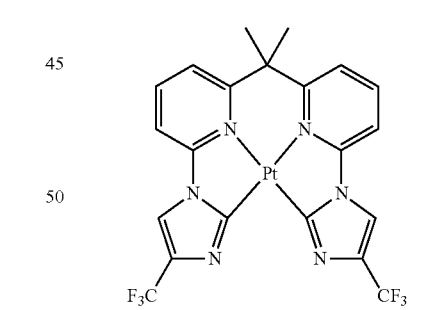
8-9
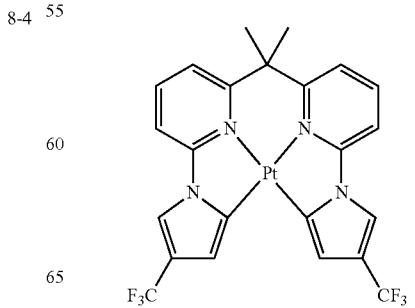
8-10

8-11
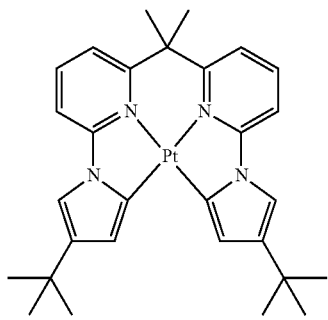
9-1
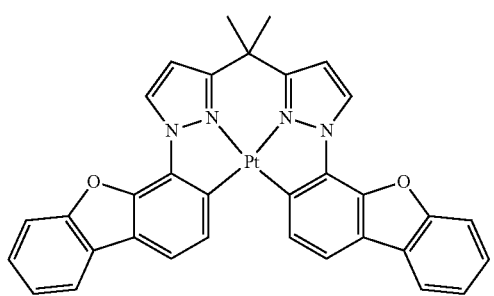
9-2
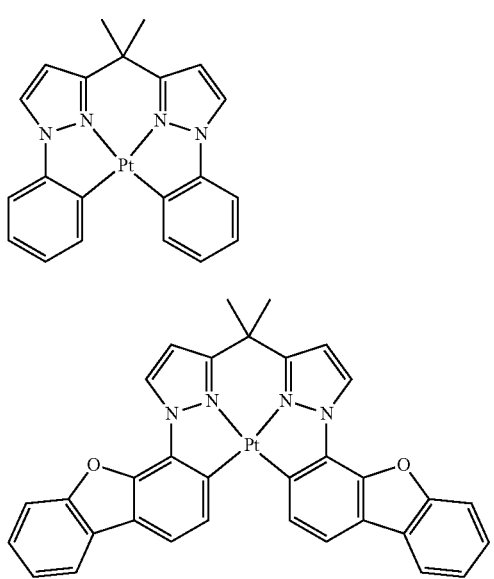
9-3
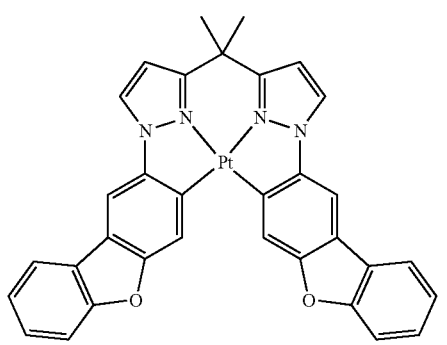
9-4
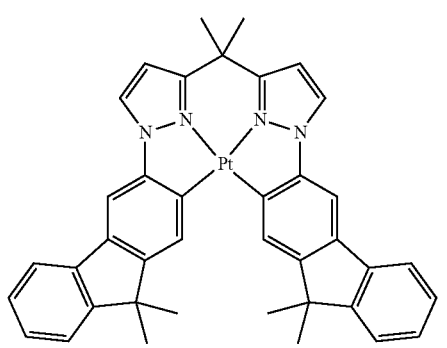
9-5
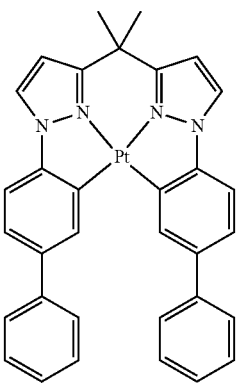
9-6
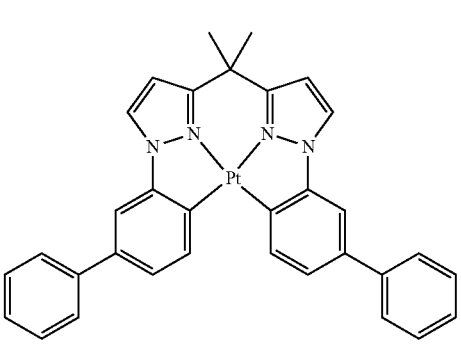
9-7
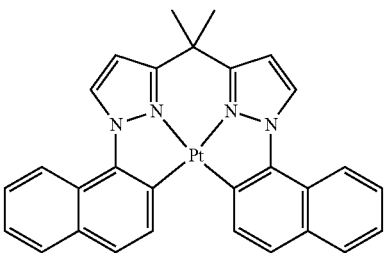
9-8
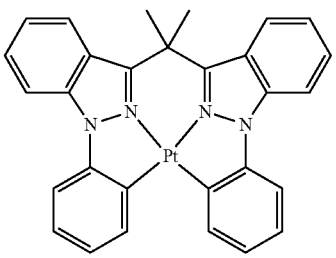
9-9
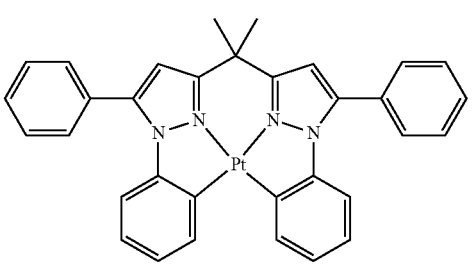

9-10
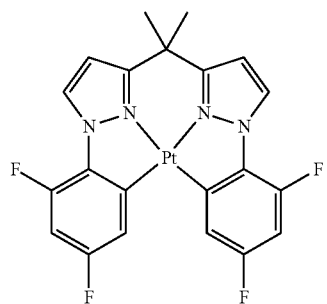
9-11
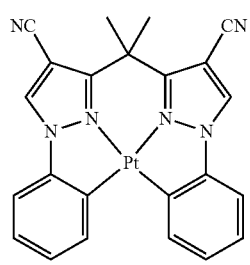
9-12
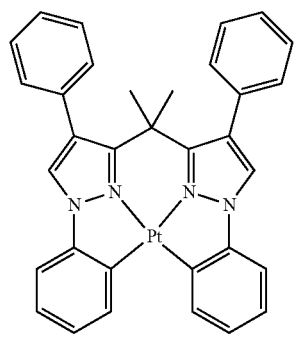
9-13
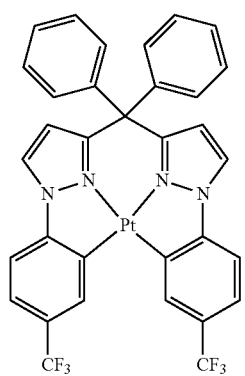
9-14
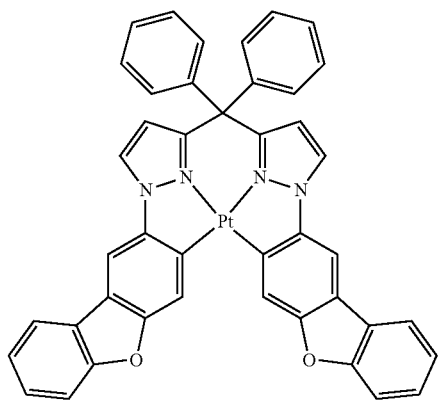
9-15
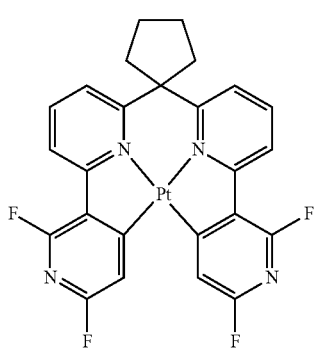
9-16
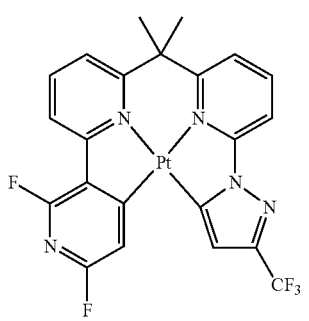
9-17
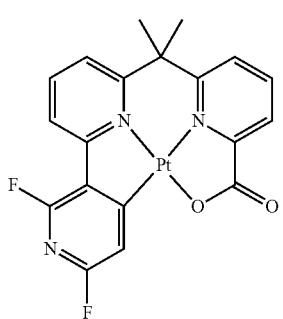

-continued 9-18

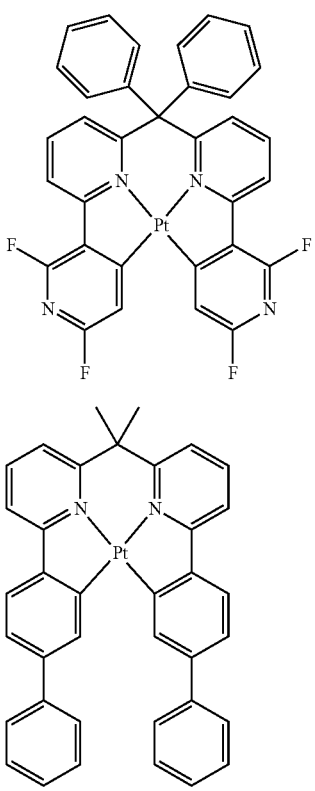

9-19

The platinum complex compound represented by the formula (C-1) may be synthesized by various techniques, for example, a method described on page 789, line 53 of the left-hand column to line 7 of the left-hand column, a method described on page 790, lines 18 to 38 of the left-hand column, a method described on page 790, lines 19 to 30 of the right-hand column in Journal of Organic Chemistry 53, 786, (1988), G. R. Newkome et al. and a combination thereof, a method described on page 2752, lines 26 to 35 in Chemische Berichte 113, 2749 (1980), H. Lexy et al. and the like.

For example, the platinum complex compound may be obtained by treating a ligand or a dissociation material thereof and a metal compound in the presence or absence of a solvent (for example, a halogen-based solvent, an alcohol-based solvent, an ether-based solvent, an ester-based solvent, a ketone-based solvent, a nitrile-based solvent, an amide-based solvent, a sulfone-based solvent, a sulfoxide-based solvent, water and the like) and in the presence of a base (various inorganic or organic bases, for example, sodium methoxide, t-butoxy potassium, triethylamine, potassium carbonate and the like) or in the absence of a base, at room temperature or a lower temperature or by heating (in addition to typical heating, a technique of heating by microwaves is also effective).

A content of the compound represented by Formula (C-1) in the light emitting layer of the present invention is preferably 1 mass % to 30 mass %, more preferably 3 mass % to 25 mass %, and even more preferably 5 mass % to 20 mass %, in the light emitting layer.

As an iridium complex, an iridium complex represented by the following Formula (T-1) is preferred.

[Compound represented by Formula (T-1)]
An explanation as for a compound represented by Formula (T-1) is described.

[Chem. 30]

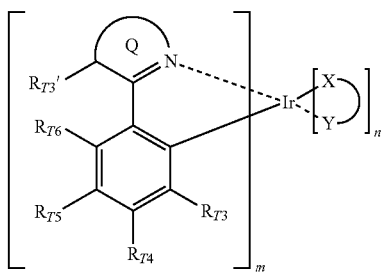

(T-1)

(In Formula (T-1), each of $R_{T3}'$, $R_{T3}$, $R_{T4}$, $R_{T5}$ and $R_{T6}$ independently represents a hydrogen atom, an alkyl group, an alkenyl group, an alkynyl group, —CN, a perfluoroalkyl group, a trifluorovinyl group, —$CO_2R_T$, —$C(O)R_T$, —$N(R_T)_2$, —$NO_2$, —$OR_T$, a fluorine atom, an aryl group or a heteroaryl group, and may further have a substituent T.

Q is a 5- or 6-membered aromatic heterocycle or a condensed aromatic heterocycle, which includes one or more nitrogens.

Any adjacent two of $R_{T3}$, $R_{T4}$, $R_{T5}$ and $R_{T6}$ may be bonded to each other to form a condensed 4- to 7-membered ring, and the condensed 4- to 7-membered ring is cycloalkyl, aryl or heteroaryl and may further have a substituent T.

$R_{T3}'$ and $R_{T6}$ may be linked by a linking group selected from —$C(R_T)_2$—$C(R_T)_2$—, —$CR_T$=$CR_T$—, —$C(R_T)_2$—, —O—, —$NR_T$—, —O—$C(R_T)_2$—, —$NR_T$—$C(R_T)_2$— and —N=$CR_T$— to form a ring, each of $R_T$ independently represents a hydrogen atom, an alkyl group, an alkenyl group, an alkynyl group, a heteroalkyl group, an aryl group or a heteroaryl group, and may further have a substituent T.

Each of the substituent T independently represents a halogen atom, —R', —OR', —N(R')$_2$, —SR', —C(O)R', —C(O)OR', —C(O)N(R')$_2$, —CN, —$NO_2$, —$SO_2$, —SOR', —$SO_2R'$ or —$SO_3R'$, and each of R' independently represents a hydrogen atom, an alkyl group, a perfluoroalkyl group, an alkenyl group, an alkynyl group, a heteroalkyl group, an aryl group or a heteroaryl group.

(X-Y) represents a ligand. m represents an integer of 1 to 3 and n represents an integer of 0 to 2. m+n is 3.)

The alkyl group may have a substituent and may be saturated or unsaturated, and examples of a group which may be substituted include the above-described substituent T. The alkyl group represented by $R_{T3}'$, $R_{T3}$, $R_{T4}$, $R_{T5}$ and $R_{T6}$ is preferably an alkyl group having a total carbon number of 1 to 8, and more preferably an alkyl group having a total carbon number of 1 to 6, and examples thereof include a methyl group, an ethyl group, an i-propyl group, a cyclohexyl group, a t-butyl group and the like.

The cycloalkyl group may have a substituent and may be saturated or unsaturated, and examples of a group which may be substituted include the above-described substituent T. The cycloalkyl group represented by $R_{T3}'$, $R_{T3}$, $R_{T4}$, $R_{T5}$ and $R_{T6}$ is preferably a cycloalkyl group having the number of ring members of 4 to 7, and more preferably a cycloalkyl group having a total carbon number of 5 and 6, and examples thereof include a cyclopentyl group, a cyclohexyl group and the like.

The alkenyl group represented by $R_{T3}'$, $R_{T3}$, $R_{T4}$, $R_{T5}$ and $R_{T6}$ is an alkenyl group having preferably 2 to 30 carbon atoms, more preferably 2 to 20 carbon atoms, and particularly preferably 2 to 10 carbon atoms, and examples thereof include vinyl, allyl, 1-propenyl, 1-isopropenyl, 1-butenyl, 2-butenyl, 3-pentenyl and the like.

The alkynyl group represented by $R_{T3}'$, $R_{T3}$, $R_{T4}$, $R_{T5}$ and $R_{T6}$ is an alkynyl group having preferably 2 to 30 carbon atoms, more preferably 2 to 20 carbon atoms, and particularly preferably 2 to 10 carbon atoms, and examples thereof include ethynyl, propargyl, 1-propynyl, 3-pentynyl and the like.

Examples of the heteroalkyl group represented by $R_{T3}'$, $R_{T3}$, $R_{T4}$, $R_{T5}$ and $R_{T6}$ include a group in which at least one carbon of the alkyl group has been substituted with O, $NR_T$ or S.

The aryl group represented by $R_{T3}'$, $R_{T3}$, $R_{T4}$, $R_{T5}$ and $R_{T6}$ is preferably a substituted or unsubstituted aryl group having 6 to 30 carbon atoms, and examples thereof include a phenyl group, a tolyl group, a naphthyl group and the like.

The heteroaryl group represented by $R_{T3}'$, $R_{T3}$, $R_{T4}$, $R_{T5}$ and $R_{T6}$ is preferably a heteroaryl group having 5 to 8 carbon atoms, and more preferably a 5- or 6-membered, substituted or unsubstituted heteroaryl group, and examples thereof include a pyridyl group, a pyrazinyl group, a pyridazinyl group, a pyrimidinyl group, a triazinyl group, a quinolinyl group, an isoquinolinyl group, a quinazolinyl group, a cinnolinyl group, phthalazinyl group, a quinoxalinyl group, a pyrrolyl group, an indolyl group, a furyl group, a benzofuryl group, a thienyl group, a benzothienyl group, a parazolyl group, an imidazolyl group, a benzimidazolyl group, a triazolyl group, an oxazolyl group, a benzoxazolyl group, a thiazolyl group, a benzothiazolyl group, an isothiazolyl group, a benzisothiazolyl group, a thiadiazolyl group, an isoxazolyl group, a benzisoxazolyl group, a pyrrolidinyl group, a piperidinyl group, a piperazinyl group, an imidazolidinyl group, a thiazolinyl group, a sulfolanyl group, a carbazolyl group, a dibenzofuryl group, a dibenzothienyl group, a pyridoindolyl group and the like. Preferred examples thereof include a pyridyl group, a pyrimidinyl group, an imidazolyl group and a thienyl group, and more preferably a pyridyl group and a pyrimidinyl group.

$R_{T3}'$, $R_{T3}$, $R_{T4}$, $R_{T5}$ and $R_{T6}$ are preferably a hydrogen atom, an alkyl group, a cyano group, a trifluoromethyl group, a perfluoroalkyl group, a dialkylamino group, a fluorine atom, an aryl group and a heteroaryl group, more preferably a hydrogen atom, an alkyl group, a cyano group, a trifluoromethyl group, a fluorine atom and an aryl group, and even more preferably a hydrogen atom, an alkyl group and an aryl group. The substituent T is preferably an alkyl group, an alkoxy group, a fluorine atom, a cyano group and a dialkylamino group, and more preferably a hydrogen atom.

Any adjacent two of $R_{T3}$, $R_{T4}$, $R_{T5}$ and $R_{T6}$ may be bonded to each other to form a condensed 4- to 7-membered ring, and the condensed 4- to 7-membered ring is cycloalkyl, aryl or heteroaryl and may further have a substituent T. The definition and preferred ranges of cycloalkyl, aryl and heteroaryl to be formed are the same as those of a cycloalkyl group, an aryl group and a heteroaryl group defined in $R_{T3}'$, $R_{T3}$, $R_{T4}$, $R_{T5}$ and $R_{T6}$.

Examples of an aromatic heterocyclic ring represented by ring Q include a pyridine ring, a pyrazine ring, a pyrimidine ring, a pyrazole ring, an imidazole ring, a triazole ring, an oxazole ring, an oxadiazole ring, a thiazole ring, a thiadiazole ring and the like. The aromatic heterocycle is preferably a pyridine ring and a pyrazine ring, and more preferably a pyridine ring.

Examples of a condensed aromatic heterocyclic ring presented by ring Q include a quinoline ring, an isoquinoline ring, a quinoxaline ring and the like. The condensed aromatic heterocyclic ring is preferably a quinoline ring and an isoquinoline ring, and more preferably a quinoline ring.

m is preferably 1 to 3, and more preferably 2 or 3. That is, n is preferably 0 or 1. The kind of ligand in a complex is preferably composed of one or two kind thereof, and more preferably one kind. From the viewpoint of easiness in synthesis when a reactive group is introduced into a complex molecule, the ligand is composed of preferably two kinds thereof.

A metal complex represented by Formula (T-1) may be composed by including a combination of a ligand represented by the following Formula (T-1-A) in Formula (T-1) or the tautomer thereof and a ligand represented by (X-Y) or the tautomer thereof, or all the ligands of the metal complex may be composed only of a ligand represented by Formula (T-1-A) or the tautomer thereof.

[Chem. 31]

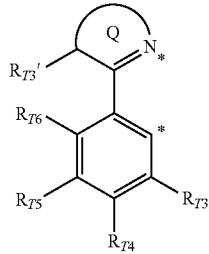

(T-1-A)

(In Formula (T-1-A), $R_{T3}'$, $R_{T3}$, $R_{T4}$, $R_{T5}$, $R_{T6}$ and Q have the same meaning as $R_{T3}'$, $R_{T3}$, $R_{T4}$, $R_{T5}$, $R_{T6}$ and Q in Formula (T-1). * represents a coordination position to iridium.)

Furthermore, a ligand (may be referred to as a coordination compound) known to those skilled in the art as a so-called ligand, which is used in the formation of the metal complex well known in the related art may be included as a ligand represented by (X-Y), if necessary.

As a ligand to be used in the metal complex known in the related art, there are various ligands which are well known, but examples thereof include ligands described in, for example, H. Yersin, "Photochemistry and Photophysics of Coordination Compounds", published by Springer-Verlag, 1987 and YAMAMOTO, Akio, "Organometallic Chemistry-Principles and Applications", published by SHOKABO PUBLISHING Co., Ltd., 1982 (for example, halogen ligands (preferably, a chlorine ligand), nitrogen-containing heteroaryl ligands (for example, bipyridyl, phenanthroline and the like) and diketone ligands (for example, acetylacetone and the like). The ligand represented by (X-Y) is preferably diketones or a picolinic acid derivative, and most preferably acetylacetonate (acac) represented as follows from the viewpoint of obtaining stability of the complex and high light emission efficiency.

[Chem. 32]

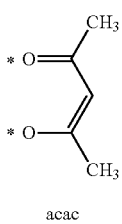

acac

\* represents a coordination position to iridium.

Hereinafter, specific examples of the ligand represented by (X-Y) are listed, but the present invention is not limited thereto.

[Chem. 33]

(I-1) 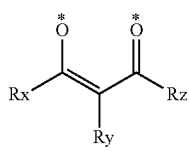

(I-2) 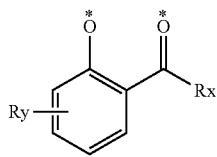

(I-3) 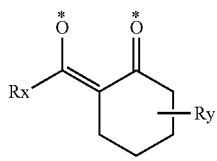

(I-4) 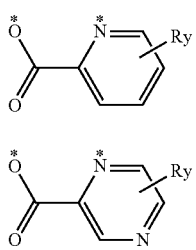

(I-5) 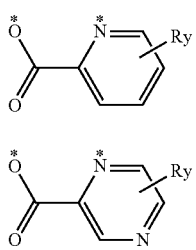

(I-6) 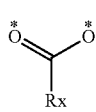

(I-7) 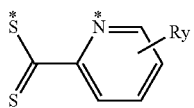

(I-8) 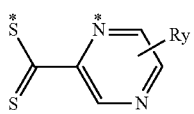

(I-9) 

(I-10) 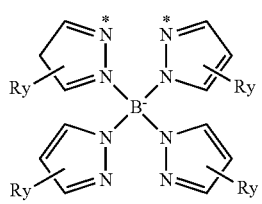

(I-11) 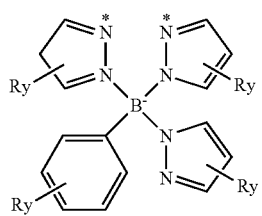

(I-12) 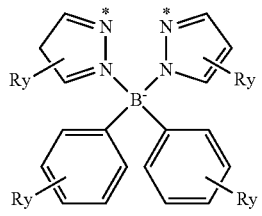

(I-13) 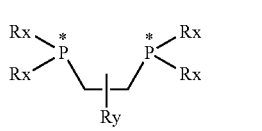

(I-14) 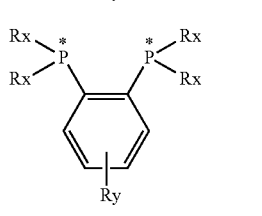

In the example of the ligand represented by (X-Y), * represents a coordination position to iridium in Formula (T-1). Each of Rx, Ry and Rz independently represents a hydrogen atom or a substituent. The substituent may include a substituent selected from the group A of substituents. Preferably, each of Rx and Rz is independently any of an alkyl group, a perfluoroalkyl group, a fluorine atom and an aryl group, more preferably an alkyl group having 1 to 4 carbon atoms, a perfluoroalkyl group having 1 to 4 carbon atoms, a fluorine atom and a phenyl group which may be substituted, and most preferably a methyl group, an ethyl group, a trifluoromethyl group, a fluorine atom and a phenyl group. Ry is preferably any of a hydrogen atom, an alkyl group, a perfluoroalkyl group, a fluorine atom and an aryl group, more preferably a hydrogen atom, an alkyl group having 1 to 4 carbon atoms and a phenyl group which may be substituted, and most preferably any of a hydrogen atom and a methyl group. It is thought that these ligands are not a site in which electrons are transported in a device or electrons are concentrated by exitation, and thus Rx, Ry and Rz may be a chemically stable substituent and do not have any influence on the effect of the present invention.

The complex is easily synthesized and thus is preferably (I-1), (I-4) and (I-5), and most preferably (I-1). The complex having these ligands may be synthesized in the same manner as in Synthetic Examples well known by using the corresponding ligand precursor. In the same manner as in a method disclosed in, for example, International Publication No. WO 2009-073245, page 46, the complex may be synthesized by a method shown in the following by using commercially available difluoroacetylacetone.

The compound represented by Formula (T-1) is preferably a compound represented by the following Formula (T-2).

[Chem. 36]

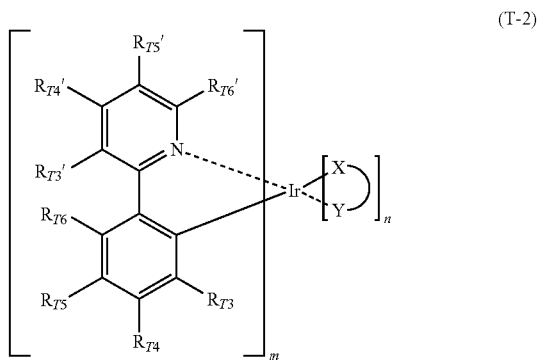

(T-2)

[Chem. 34]

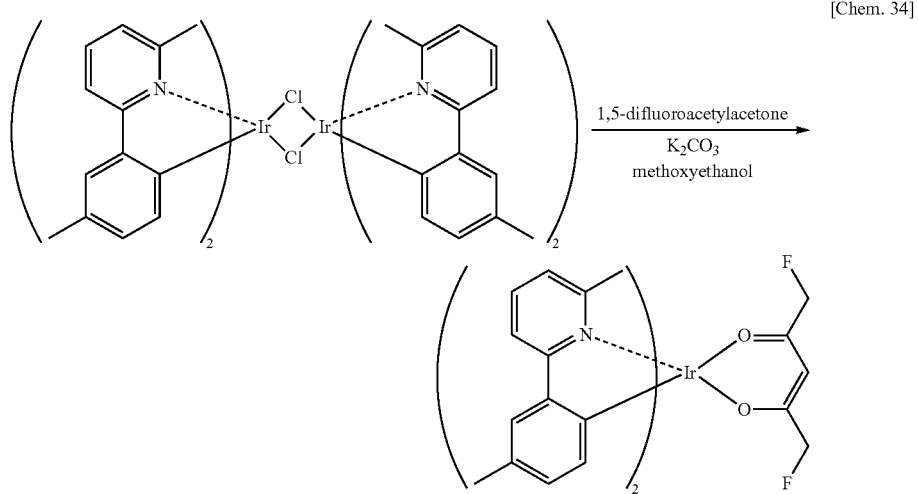

In addition, a mono-anionic ligand represented by Formula (I-15) may be used as a ligand.

[Chem. 35]

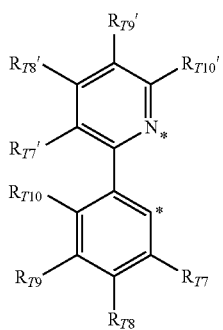

(I-15)

$R_{T7}$ to $R_{T10}$ in Formula (I-15) have the same meaning as $R_{T3}$ to $R_{T6}$ in Formula (T-1), and preferred ranges thereof are also the same. $R_{T7}'$ to $R_{T10}'$ have the same meaning as $R_{T3}'$, and preferred ranges thereof are also the same as $R_{T3}'$. * represents a coordination position to iridium.

(In Formula (T-2), each of $R_{T3}'$ to $R_{T6}'$ and $R_{T3}$ to $R_{T6}$ independently represents a hydrogen atom, an alkyl group, an alkenyl group, an alkynyl group, —CN, a perfluoroalkyl group, a trifluorovinyl group, —CO$_2$R$_T$, —C(O)R$_T$, —N(R$_T$)$_2$, —NO$_2$, —OR$_T$, a fluorine atom, an aryl group or a heteroaryl group, and may further have a substituent T.

Any adjacent two of $R_{T3}$, $R_{T4}$, $R_{T5}$ and $R_{T6}$ may be bonded to each other to form a condensed 4- to 7-membered ring, and the condensed 4-membered to 7-membered ring may further have a substituent T.

$R_{T3}'$ and $R_{T6}$ may be linked by a linking group selected from —C(R$_T$)$_2$—C(R$_T$)$_2$—, —CR$_T$=CR$_T$—, —C(R$_T$)$_2$—, —O—, —NR$_T$—, —O—C(R$_T$)$_2$—, —NR$_T$—C(R$_T$)$_2$— and —N=CR$_T$— to form a ring.

Each of R$_T$ independently represents a hydrogen atom, an alkyl group, an alkenyl group, an alkynyl group, a heteroalkyl group, an aryl group or a heteroaryl group, and may further have a substituent T.

Each of the substituent T independently represents a fluorine atom, —R', —OR', —N(R')$_2$, —SR', —C(O)R', —C(O)OR', —C(O)N(R')$_2$, —CN, —NO$_2$, —SO$_2$, —SOR', —SO$_2$R' or —SO$_3$R', and each of R' independently represents a hydrogen atom, an alkyl group, a perfluoroalkyl group, an alkenyl group, an alkynyl group, a heteroalkyl group, an aryl group or a heteroaryl group.

(X-Y) represents a ligand. m represents an integer of 1 to 3 and n represents an integer of 0 to 2. m+n is 3.)

Preferred ranges of $R_{T3}'$, $R_{T3}$ to $R_{T6}$, (X-Y), m and n in Formula (T-2) are the same as the preferred ranges of $R_{T3}'$, $R_{T3}$ to $R_{T6}$, (X-Y), m and n in Formula (T-1).

$R_{T4}'$ is preferably a hydrogen atom, an alkyl group, an aryl group and a fluorine atom, and more preferably a hydrogen atom.

$R_{T5}'$ and $R_6'$ preferably represent a hydrogen atom or are bonded to each other to form a condensed 4- to 7-membered cyclic group, and the condensed 4- to 7-membered cyclic group is more preferably cycloalkyl, cycloheteroalkyl, aryl or heteroaryl, and even more preferably aryl.

The substituent T in $R_{T4}'$ to $R_{T6}'$ is preferably an alkyl group, an alkoxy group, a fluorine atom, a cyano group, an alkylamino group and a diarylamino group, and more preferably an alkyl group.

One of the preferred forms of the compound represented by Formula (T-2) is the case in which any adjacent two of $R_{T3}'$, $R_{T4}'$, $R_{T5}'$, $R_{T6}'$, $R_{T3}$, $R_{T4}$, $R_{T5}$ and $R_{T6}$ in the Formula (T-2) are bonded to each other and do not form a condensed ring.

One of the preferred embodiments of the compound represented by Formula (T-2) is the case in which the compound is represented by the following Formula (T-3).

[Chem. 37]

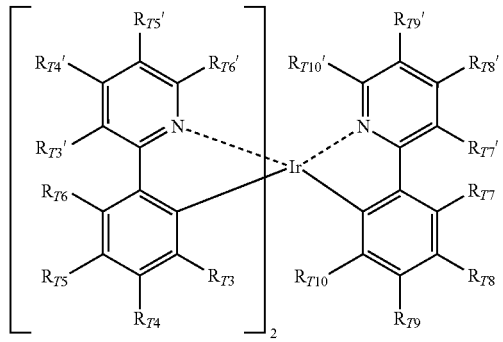

(T-3)

$R_{T3}'$ to $R_{T6}'$ and $R_{T3}$ to $R_{T6}$ in Formula (T-3) have the same meaning as $R_{T3}'$ to $R_{T6}'$ and $R_{T3}$ to $R_{T6}$ in Formula (T-2), and preferred ranges thereof are also the same.

$R_{T7}$ to $R_{T10}$ have the same meaning as $R_{T3}$ to $R_{T6}$, and preferred ranges thereof are also the same. $R_{T7}'$ to $R_{T10}'$ have the same meaning as $R_{T3}'$ to $R_{T6}'$, and preferred ranges thereof are also the same.

Another preferred embodiment of the compound represented by Formula (T-2) is a compound represented by the following Formula (T-4).

[Chem. 38]

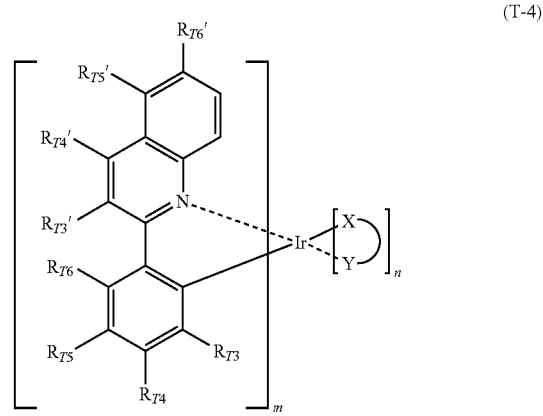

(T-4)

$R_{T3}'$ to $R_{T6}'$, $R_{T3}$ to $R_{T6}$, (X-Y), m and n in Formula (T-4) have the same meaning as $R_{T3}'$ to $R_{T6}'$, $R_{T3}$ to $R_{T6}$, (X-Y), m and n in Formula (T-2), and preferred ranges thereof are also the same. It is particularly preferred that zero to two of $R_{T3}'$ to $R_{T6}'$ and $R_{T3}$ to $R_{T6}$ are an alkyl group or a phenyl group, and the rest are all a hydrogen atom, and it is even more preferred that one or two of $R_{T3}'$ to $R_{T6}'$ and $R_{T/3}$ to $R_{T6}$ are an alkyl group and the rest are all a hydrogen atom.

Another preferred embodiment of the compound represented by Formula (T-2) is a compound represented by the following Formula (T-5).

[Chem. 39]

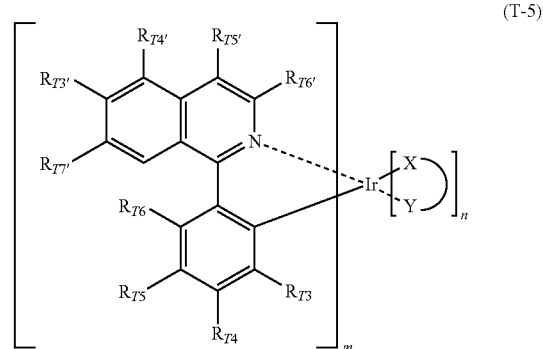

(T-5)

$R_{T3}'$ to $R_{T7}'$, $R_{T3}$ to $R_{T6}$, (X-Y), m and n in Formula (T-5) have the same meaning as $R_{T3}'$ to $R_{T6}'$, $R_{T3}$ to $R_{T6}$, (X-Y), m and n in Formula (T-2), and preferred ranges thereof are also the same.

Another preferred embodiment of the compound represented by Formula (T-1) is the case in which a compound is represented by the following Formula (T-6).

[Chem. 40]

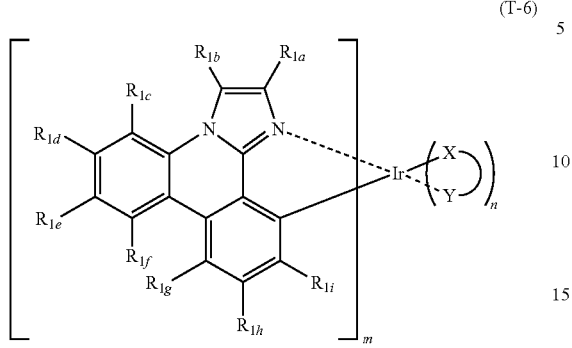

(T-6)

The definition or preferred ranges of $R_{1a}$ to $R_{1i}$ in Formula (T-6) are the same as in the definition or preferred ranges of $R_{T3}$ to $R_{T6}$ in Formula (T-1). In addition, it is particularly preferred that zero to two of $R_{1a}$ to $R_{1i}$ are an alkyl group or an aryl group and the rest are all a hydrogen atom. The definition or preferred ranges of (X-Y), m and n are the same as the definition or preferred ranges of (X-Y), m and n in Formula (T-1).

Preferred specific examples of the compound represented by Formula (T-1) are listed below, but are not limited thereto.

[Chem. 41]

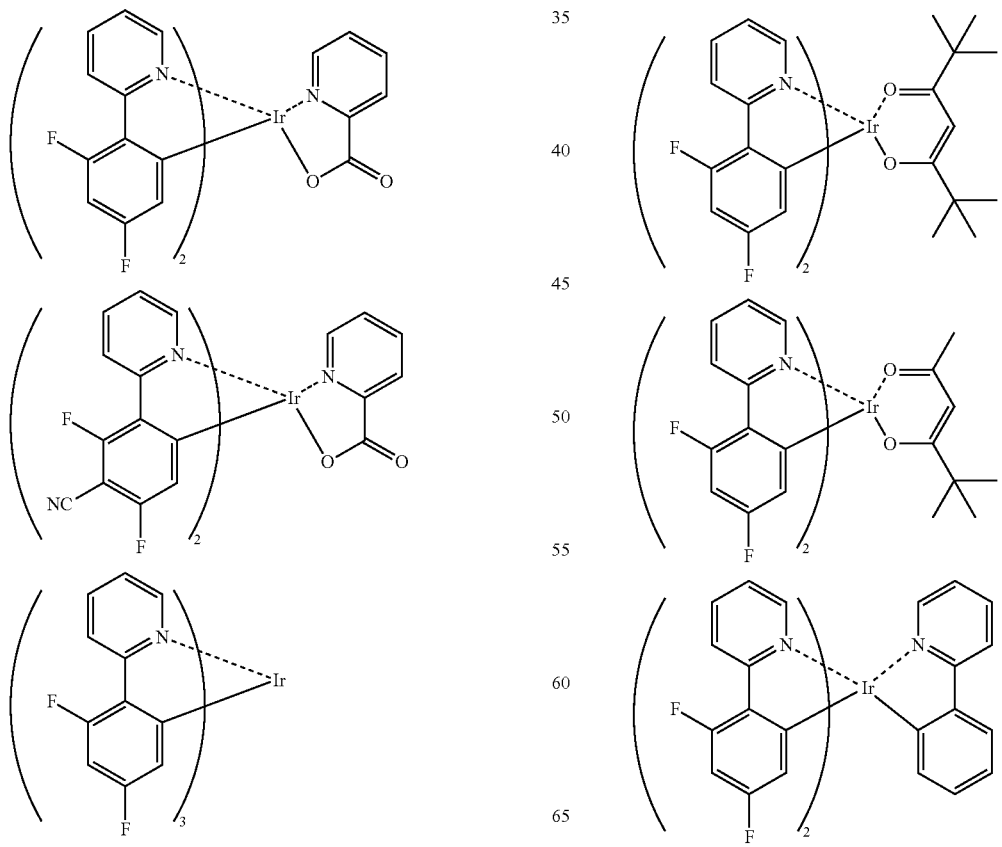

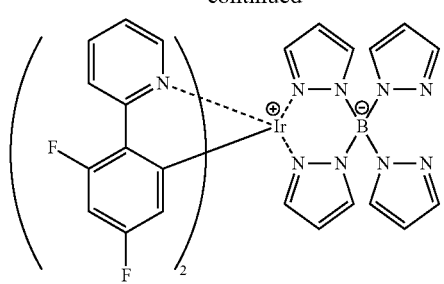
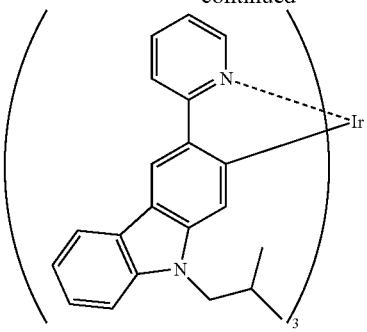
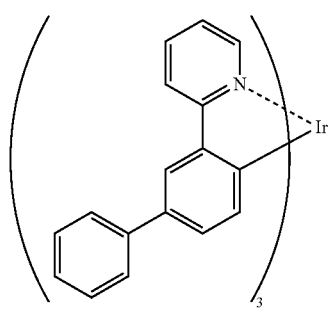
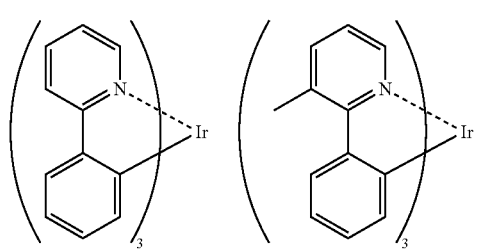
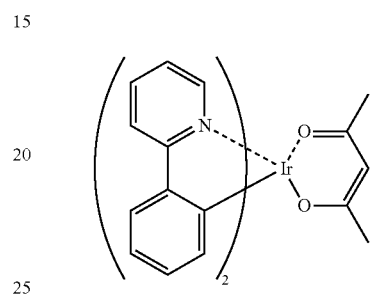
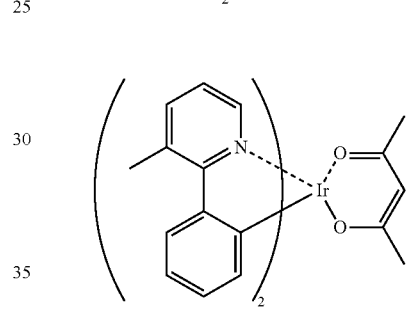
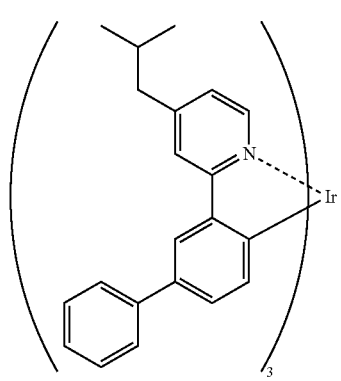
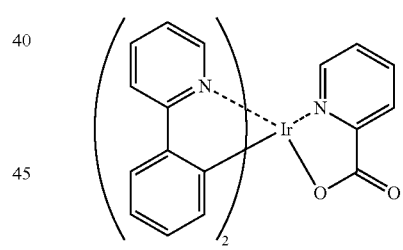
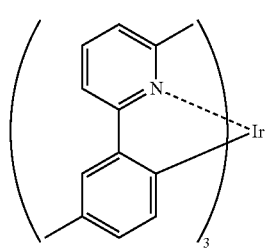
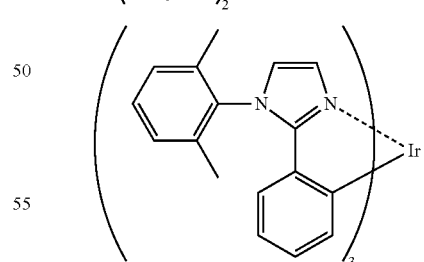
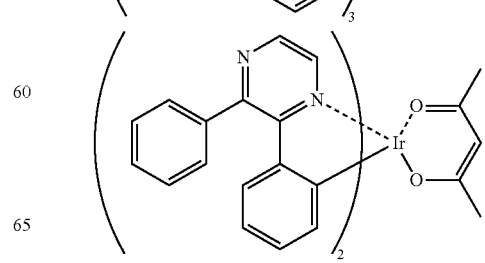

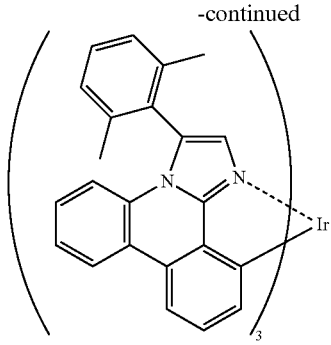
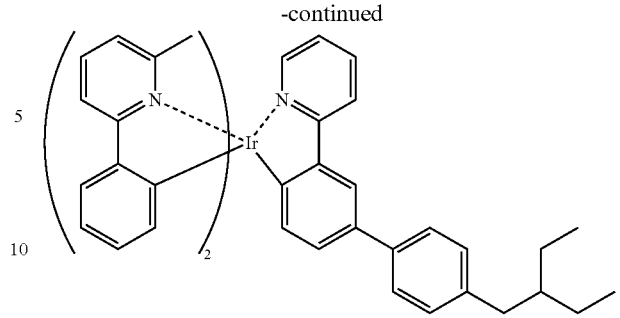
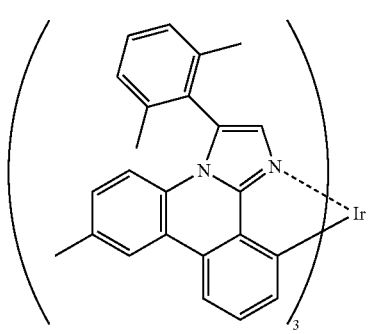
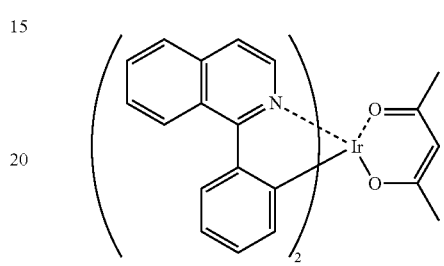
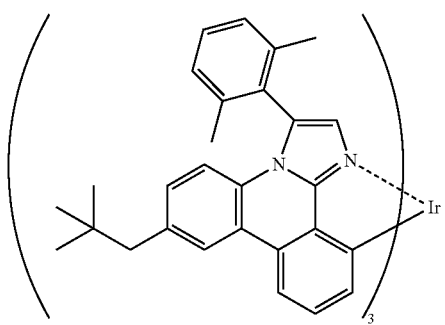
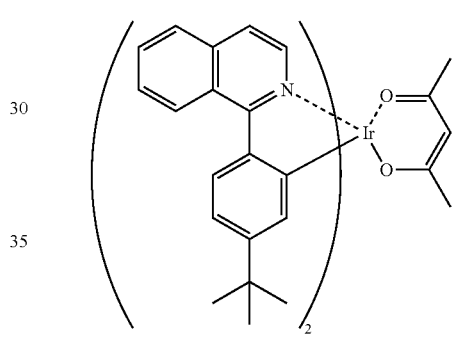
[Chem. 42]
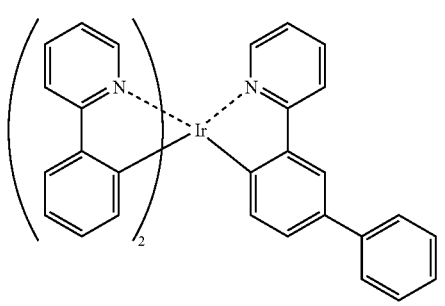
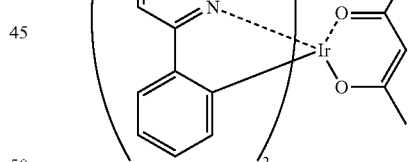
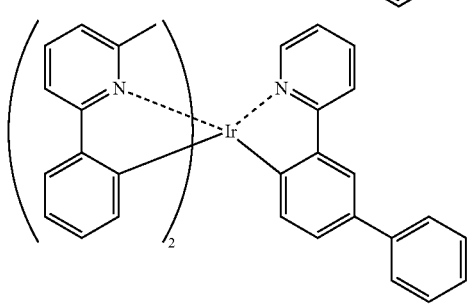
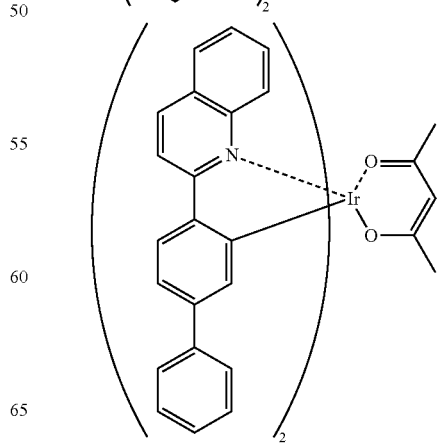

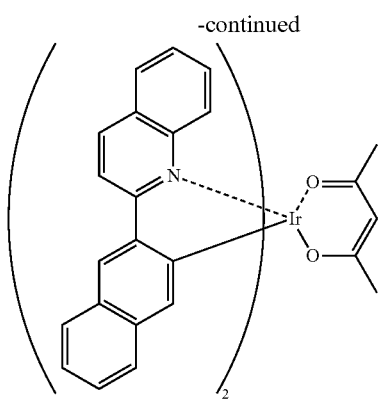
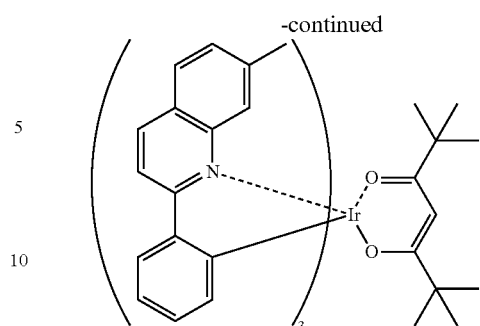
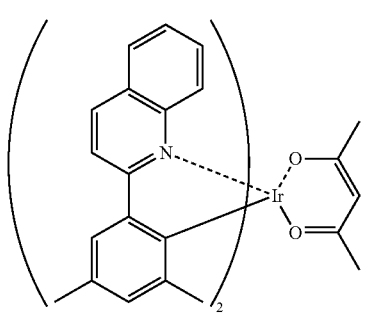
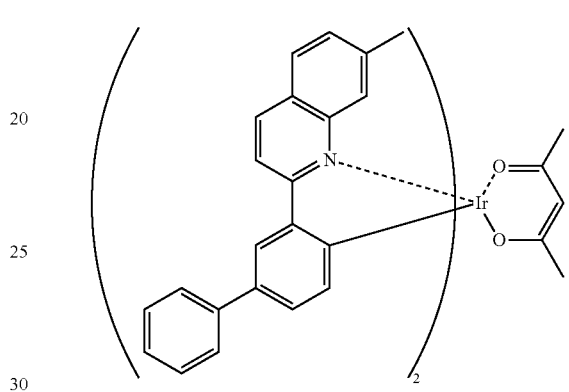
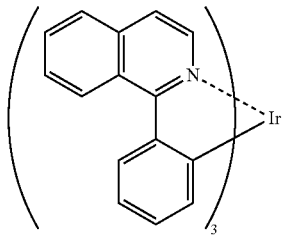
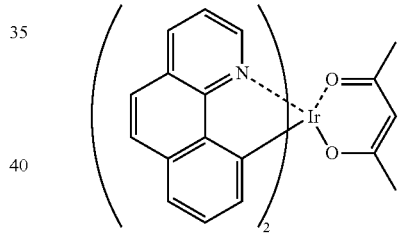
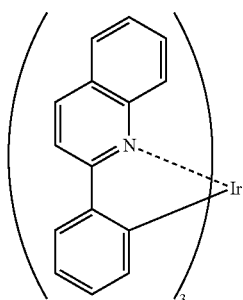
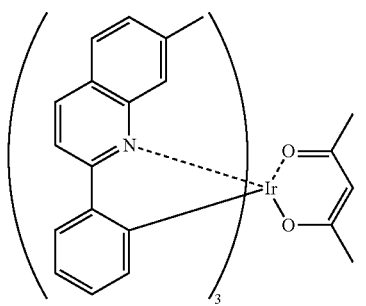

The compound exemplified as the compound represented by Formula (T-1) may be synthesized by a method disclosed in Japanese Patent Application Laid-Open No. 2009-99783 or by various methods disclosed in U.S. Pat. No. 7,279,232 and the like. After the synthesis, it is preferred that purification by column chromatography, recrystallization and the like is performed, and then purification is performed by sublimation purification. By sublimation purification, organic impurities may be separated and inorganic salts, residual solvents and the like may be effectively removed.

The compound represented by Formula (T-1) is contained in the light emitting layer, the use thereof is not limited, and the compound may be further contained in any layer in the organic layer.

As the iridium complex, in addition to the compound represented by Formula (T-1), a compound represented by the following Formula (T-7) or a compound having carbene as a ligand may be preferably used.

[Chem. 43]

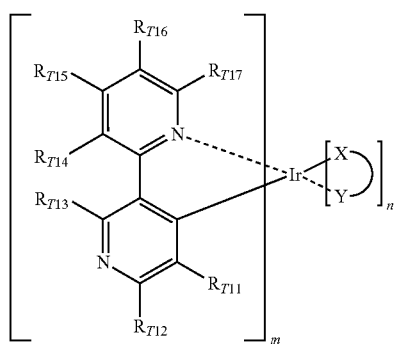

(T-7)

In Formula (T-7), $R_{T11}$ to $R_{T17}$ have the same meaning as $R_{T3}$ to $R_{T6}$ in Formula (T-2), and preferred ranges thereof are also the same. Furthermore, (X-Y), n and m have the same meaning as (X-Y), n and m in Formula (T-2), and preferred ranges thereof are the same.

Preferred specific examples thereof are listed below, but are not limited thereto.

[Chem. 44]

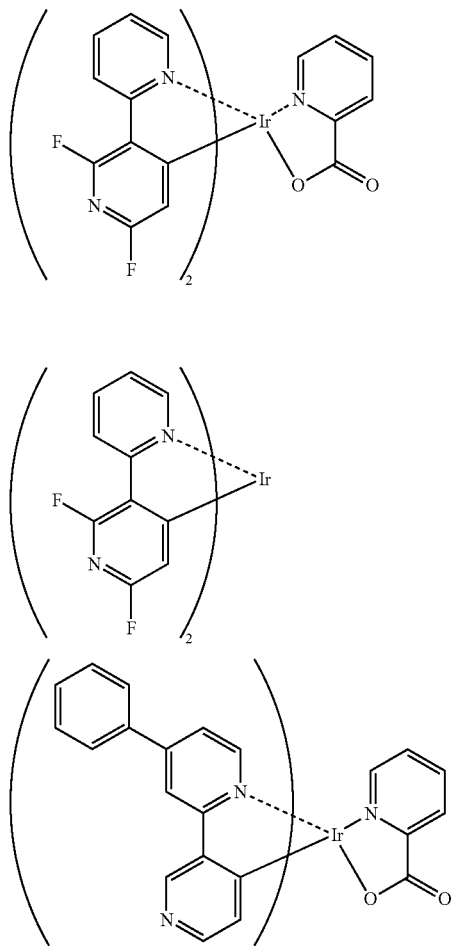

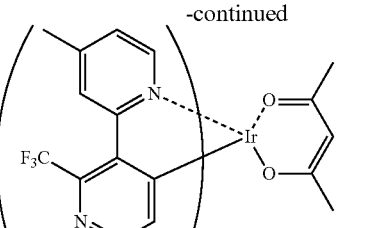

-continued

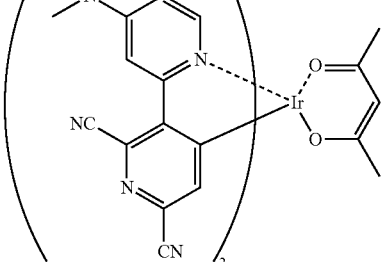

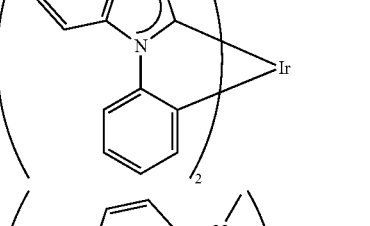

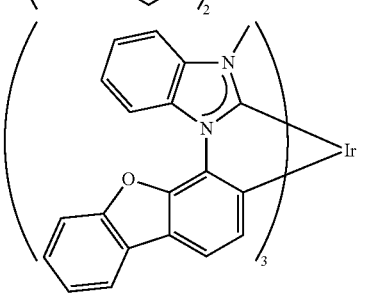

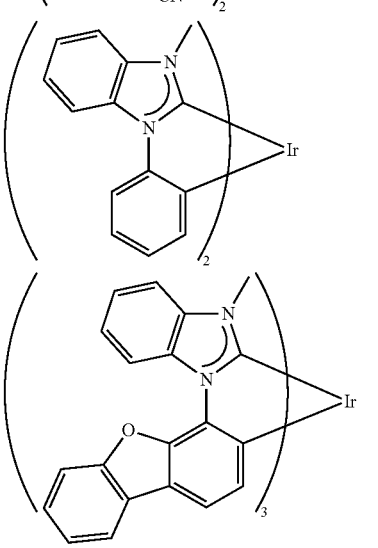

The light emitting material in the light emitting layer is included in an amount of 0.1 mass % to 50 mass % based on the mass of the total compounds which generally form the light emitting layer in the light emitting layer, preferably 1 mass % to 50 mass % by mass from the viewpoint of durability and external quantum efficiency, and even more preferably 2 mass % to 40 mass %.

Though a thickness of the light emitting layer is not particularly limited, typically, the thickness is preferably 2 nm to 500 nm. Among them, from the viewpoint of external quantum efficiency, the thickness is more preferably 3 nm to 200 nm, and even more preferably 5 nm to 100 nm The light emitting layer in the device of the present invention may be composed of a mixed layer of a host material and a light emitting material. The light emitting material may be a fluorescent light emitting material or a phosphorescent light emitting material, and the dopant may be used either alone or in combination of two or more kinds. The host material is preferably a charge transporting material. The host material may be used either alone or in combination of two or more kinds, and may have, for example, a configuration of a mixture of an electron transporting host material and a hole transporting host material. Further, a material which does not have a charge transporting property and does not emit light may be included in the light emitting layer.

In addition, the light emitting layer may be a single layer or a multi-layer of two or more layers. Furthermore, each light emitting layer may emit light with different light emission colors.

<Host Material>

A host material used in the present invention is preferably a compound represented by Formula (1).

The compound represented by Formula (1) is a compound capable of transporting a hole and a positive charge of electron, and may be used in combination of the hydrocarbon compound represented by Formula (Tp-1) to decrease a charge injection barrier or decrease the electric field intensity dependence of electric charge mobility.

The host material used in the present invention may contain the following compound in addition to the compound represented by Formula (1).

Examples of the host material include an electron transporting material and a hole transporting material, and preferably an electron transporting material. The host material may be used either alone or in combination of two or more kinds, and may have, for example, a configuration of a mixture of an electron transporting host material and a hole transporting host material.

Examples of the host material include pyrrole, indole, carbazole (for example, CBP (4,4'-di(9-carbazoyl)biphenyl)), azaindole, azacarbazole, triazole, oxazole, oxadiazole, pyrazole, imidazole, thiophene, polyarylalkane, pyrazoline, pyrazolone, phenylenediamine, arylamine, amino substituted chalcone, styrylanthracene, fluorenone, hydrazone, stilbene, silazane, aromatic tertiary amine compounds, styrylamine compounds, porphyrin-based compounds, polysilane-based compounds, poly(N-vinylcarbazole), aniline-based copolymers, electrically conductive high-molecular oligomers such as thiophene oligomers, polythiophene and the like, organosilanes, carbon films, pyridine, pyrimidine, triazine, imidazole, pyrazole, triazole, oxazole, oxadiazole, fluorenone, anthraquinodimethane, anthrone, diphenylquinone, thiopyran dioxide, carbodiimide, fluorenylidenemethane, distyrylpyrazine, fluorine-substituted aromatic compounds, heterocyclic tetracarboxylic acid anhydrides such as naphthalene perylene and the like, phthalocyanine, and a variety of metal complexes represented by metal complexes of a 8-quinolinol derivative, metal phthalocyanine, and metal complexes having benzoxazole or benzothiazole as the ligand thereof, derivatives thereof (which may have a substituent or a condensed ring) and the like.

In the light emitting layer in the present invention, it is preferred that the lowest triplet excitation energy ($T_1$ energy) of the host material is higher than the $T_1$ energy of the phosphorescent light emitting material from the viewpoint of color purity, light emission efficiency, and drive durability.

Further, the content of the host compound in the present invention is not particularly limited, but is preferably 15 mass % to 95 mass % based on the mass of the total compounds forming the light emitting layer, from the viewpoint of light emission efficiency and driving voltage.

(Electric Charge Transporting Layer)

The electric charge transporting layer refers to a layer in which the electric charge movement is generated when voltage is applied on an organic electroluminescence device. Specific examples thereof include a hole injection layer, a hole transporting layer, an electron blocking layer, a light emitting layer, a hole blocking layer, an electron transporting layer or an electron injection layer. Preferred examples thereof include a hole injection layer, a hole transporting layer, an electron blocking layer or a light emitting layer. If an electric charge transporting layer to be formed by an application method is a hole injection layer, a hole transporting layer, an electron blocking layer or a light emitting layer, an organic electroluminescence device may be produced at a low cost and a high efficiency. In addition, the electric charge transporting layer is more preferably a hole injection layer, a hole transporting layer or an electron blocking layer.

(Hole Injection Layer and Hole Transporting Layer)

Each of the hole injection layer and the hole transporting layer is a layer having a function of accepting holes from the anode or the anode side to transport the holes into the cathode side.

The hole injection layer preferably contains an electron accepting dopant. Effects that the hole injection property is improved, driving voltage is reduced, efficiency is improved and the like are exhibited by containing the electron accepting dopant in the hole injection layer. The electron accepting dopant may be any of organic materials and inorganic materials as long as the dopant is a material capable of withdrawing electrons from a material to be doped to generate radical cations, and examples thereof include tetracyanoquinodimethane (TCNQ), tetrafluorotetracyanoquinodimethane ($F_4$-TCNQ), molybdenum oxide and the like.

The electron accepting dopant in the hole injection layer is contained in an amount of preferably 0.1 mass % to 50 mass %, more preferably 0.1 mass % to 40 mass %, and more preferably 0.5 mass % to 30 mass %, based on the mass of the total compounds forming the hole injection layer.

(Electron Injection Layer and Electron Transporting Layer)

Each of the electron injection layer and the electron transporting layer is a layer having a function of accepting electrons from the cathode or the cathode side to transport the electrons into the anode side. Each of an electron injection material and an electron transporting material which is used in these layers may be a low-molecular weight compound or a polymer compound.

The electron injection layer preferably contains an electron donating dopant. Containing the electron donating dopant in the electron injection layer results in effects that the electron injection property is improved, driving voltage is reduced, efficiency is improved, and the like. The electron donating dopant may be any of organic materials and inorganic materials as long as the dopant is a material capable of imparting electrons to a material to be doped to generate radical anions, and examples thereof include tetrathialfulvalene (TTF), tetrathianaphthacene (TTT), lithium, cesium and the like.

The electron donating dopant in the electron injection layer is contained in an amount of preferably 0.1 mass % to 50 mass %, more preferably 0.1 mass % to 40 mass %, and more preferably 0.5 mass % to 30 mass %, based on the mass of the total compounds forming the electron injection layer.

The injection of electric charges from the electrodes may be generally promoted to reduce the driving voltage by containing an electron accepting dopant in the hole injection layer and an electron donating dopant in the electron injection layer, and if the electric charge balance in the device is destroyed by them, the light emitting position may be changed to promote the reduction in light emission efficiency or reduction in driving durability and various changes when driving at a high luminance. Since the device of the present invention has a small electric charge injection barrier at the interface of a layer adjacent to the light emitting layer/a light emitting layer on the cathode side and a small electric charge trap in the light emitting layer or the layer adjacent to the light emitting layer on the cathode side, it is difficult to accumulate electric charges in the device, and a balance of electron mobility of the layer adjacent to the light emitting layer on the cathode side and hole mobility and electron mobility of the light emitting layer is good. For these reasons and the like, the device of the present invention is a device which makes it difficult to destroy the balance of electric charges for the change in amount of electric charge injection. Accordingly, the driving voltage may be reduced without deteriorating the efficiency, durability, various changes when driving at a high luminance by containing an electron accepting dopant in the hole injection layer and an electron donating dopant in the electron injection layer.

The hole injection layer, the hole transporting layer, the electron injection layer and the electron transporting layer are described in detail in, for example, Japanese Patent Application Laid-Open No. 2008-270736 and Japanese Patent Application Laid-Open No. 2007-266458, and subject matters described in these publications may be applied to the present invention.

(Hole Blocking Layer)

The hole blocking layer is a layer having a function of preventing a hole transported to the light emitting layer from the anode side from penetrating to the cathode side. In the present invention, the hole blocking layer may be formed as an organic layer adjacent to the light emitting layer on the cathode side.

Examples of the organic compound constituting the hole blocking layer include an aluminum complex such as aluminum(III) bis(2-methyl-8-quinolinato)-4-phenylphenolate (simply referred to as BAlq) and the like, triazole derivatives, phenanthroline derivatives such as 2,9-dimethyl-4,7-diphenyl-1,10-phenanthroline (simply referred to as BCP) and the like, in addition to the compounds represented by Formula (1) in the present invention.

The thickness of the hole blocking layer is preferably 1 nm to 500 nm, more preferably 5 nm to 200 nm, and even more preferably 10 nm to 100 nm.

The hole blocking layer may be a single layer structure composed of one or two or more kinds of the above-described materials or may have a multilayer structure composed of a plurality of layers of the same or different compositions.

(Electron Blocking Layer)

The electron blocking layer is a layer having a function of preventing an electron transported to the light emitting layer from the cathode side from penetrating to the anode side. In the present invention, the electron blocking layer may be formed as an organic layer adjacent to the light emitting layer on the cathode side.

As an example of the organic compound constituting the electron blocking layer, for example, those exemplified as the above-described hole transporting material may be applied.

The thickness of the electron blocking layer is preferably 1 nm to 500 nm, more preferably 5 nm to 200 nm, and even more preferably 10 nm to 100 nm.

The electron blocking layer may be a single layer structure composed of one or two or more kinds of the above-described materials or may have a multilayer structure composed of a plurality of layers of the same or different compositions.

(Protective Layer)

In the present invention, the entire organic EL device may be protected by a protective layer.

A material to be included in the protective layer may be any one as long as the material has a function of inhibiting those promoting the deterioration of the device, such as moisture, oxygen and the like from being incorporated into the device.

With respect to the protective layer, subject matters described in paragraph Nos. [0169] and [0170] of Japanese Patent Application Laid-Open No. 2008-270736, may be applied to the present invention.

(Sealing Container)

In the device of the present invention, the entire device may be sealed by using a sealing container.

With respect to the sealing container, subject matters described in paragraph No. [0171] of Japanese Patent Application Laid-Open No. 2008-270736 may be applied to the present invention.

Furthermore, a moisture absorbent or an inert liquid may be sealed in a space between the sealing container and the luminescence device. The moisture absorbent is not particularly limited, and examples thereof include barium oxide, sodium oxide, potassium oxide, calcium oxide, sodium sulfate, calcium sulfate, magnesium sulfate, phosphorus pentoxide, calcium chloride, magnesium chloride, copper chloride, cesium fluoride, niobium fluoride, calcium bromide, vanadium bromide, molecular sieves, zeolites, magnesium oxide and the like. The inert liquid is not particularly limited, and examples thereof include paraffins, fluid paraffins, fluorine-based solvents such as perfluoroalkane, perfluoroamine, perfluoroether and the like, chlorine-based solvents and silicone oils.

(Driving)

In the organic electroluminescent device of the present invention, light emission may be obtained by applying a voltage (typically 2 volts to 15 volts) of direct current (may include an alternating current component if necessary) or a current of direct current between the anode and the cathode.

With respect to the driving method of the organic electroluminescence device of the present invention, driving methods described in each publication of Japanese Patent Application Laid-Open Nos. H2-148687, 6-301355, H5-29080, H7-134558, H8-234685, and H8-241047 and each specification of Japanese Patent No. 2784615, U.S. Pat. Nos. 5,828,429 and 6,023,308 and the like may be applied.

The external quantum efficiency of the organic electroluminescence device of the present invention is preferably 5% or more, and more preferably 7% or more. As values of external quantum efficiency, a maximum value of external quantum efficiency when the device is driving at 20° C. or a value of external quantum efficiency in the vicinity of 100 $cd/m^2$ to 300 $cd/m^2$ when the device is driven at 20° C. may be used.

The internal quantum efficiency of the organic electroluminescence device of the present invention is preferably 30% or more, more preferably 50% or more, and even more preferably 70% or more. The internal quantum efficiency of the device is calculated by dividing the external quantum efficiency by the light extraction efficiency. Although typical organic EL devices have an light extraction efficiency of about 20%, it is possible to achieve a light extraction efficiency of 20% or more by studying the shape of the substrate, the shape of the electrode, the film thickness of the organic layer, the film thickness of the inorganic layer, the refractive index of the organic layer, the refractive index of the inorganic layer and the like.

The organic electroluminescence device of the present invention has a local maximum emission wavelength (maximum strength wavelength of the emission spectrum) of preferably 350 nm to 700 nm, more preferably 350 nm to 600 nm, and even more preferably 400 nm to 520 nm, particularly more preferably 400 nm to 465 nm.

(Use of Luminescence Device of the Present Invention)

The luminescence device of the present invention may be suitably used for light emission apparatuses, pixels, display devices, displays, backlights, electrophotography, illumination light sources, recording light sources, exposure light sources, reading light sources, indicators, signboards, interiors, or optical communication and the like. In particular, the luminescence device of the present invention is preferably used for a device that is driven in a region with high luminescence, such as an illumination apparatus, a display apparatus and the like.

(Light Emission Apparatus)

Subsequently, the light emission apparatus of the present invention will be described with reference to FIG. 2.

The light emission apparatus of the present invention is made by using the organic electroluminescence device.

Figure 2:
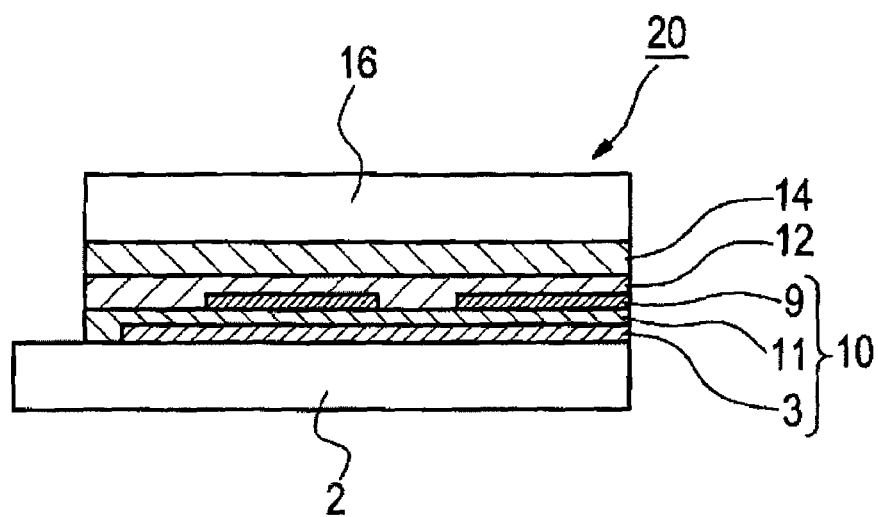
FIG. 2 is a schematic view illustrating an example of a light emission apparatus according to the present invention.

FIG. 2 is a cross-sectional view schematically illustrating an example of a light emission apparatus of the present invention.

A light emission apparatus 20 of FIG. 2 is composed of a substrate (supporting substrate) 2, an organic electroluminescence device 10, a sealing container 16 and the like.

The organic electroluminescence device 10 is configured by sequentially stacking an anode (first electrode) 3, an organic layer 11 and a cathode (second electrode) 9 on the substrate 2. In addition, a protective layer 12 is stacked on the cathode 9. Furthermore, the sealing container 16 is provided on the protective layer 12 through an adhesion layer 14. Meanwhile, a part of each of the electrodes 3 and 9, a partition wall, an insulating layer and the like are omitted.

Here, as the adhesion layer 14, a photocurable or thermosetting adhesive such as an epoxy resin and the like may be used and, for example, a thermosetting adhesive sheet may also be used.

The light emission apparatus of the present invention is not particularly limited in the use thereof and, for example, may be used not only as an illumination apparatus but also as a display apparatus such as a television set, a personal computer, a cellular phone, an electronic paper and the like.

(Illumination Apparatus)

Subsequently, an illumination apparatus according to embodiments of the present invention will be described with reference to FIG. 3.

FIG. 3 is a cross-sectional view schematically illustrating an example of the illumination apparatus according to embodiments of the present invention.

An illumination apparatus 40 according to embodiments of the present invention includes, as illustrated in FIG. 3, the above-described organic EL device 10 and a light scattering member 30. More specifically, the illumination apparatus 40 is configured such that the substrate 2 of the organic EL device 10 and the light scattering member 30 are put into contact.

The light scattering member 30 is not particularly limited as long as the member may scatter light, but in FIG. 3, a member obtained by dispersing fine particles 32 in a transparent substrate 31 is used. Suitable examples of the transparent substrate 31 include a glass substrate. Suitable examples of the fine particle 32 include a transparent resin fine particle. As the glass substrate and the transparent resin fine particle, all the products well known in the art may be used. In such an illumination apparatus 40, when light emitted from the organic electroluminescence device 10 is incident on a light incident surface 30A of the scattering member 30, the incident light is scattered by the light scattering member 30 and the scattered light is outputted as illuminating light from a light exit surface 30B.

EXAMPLE

Hereinafter, the present invention will be described in detail with reference to Examples, but the present invention is not limited thereto.

The compounds represented by Formula (1) and Formula (2), used in Examples, were synthesized with reference to a method disclosed in International Publication No. WO 2004/074399. For example, the compound (1) was synthesized by a method described in page 52 line 22 to page 54 line 15 of International Publication No. WO 2004/074399. The compound represented by Formula (Tp-1) was synthesized with reference to a method disclosed in International Publication No. WO 05/013388, International Publication No. WO 06/130598, and International Publication No. WO 09/021,107. For example, the compound (A) was synthesized by a method disclosed in [0093] to [0094] of International Publication No. WO 05/013388.

Meanwhile, the organic materials used in the Example were all purified by sublimation and analyzed by high-speed liquid chromatography (TOSOH CORPORATION TSKgel ODS-100Z), and had an absorption intensity area ratio of 99.9% or more at 254 nm.

Example 1

Manufacture of Device

A glass substrate having an ITO film having a thickness of 0.5 mm and each side of 2.5 cm in square (manufactured by GEOMATEC Co., Ltd., and surface resistance 10Ω/□) was put into a washing container, and ultrasonically washed in 2-propanol, followed by UV-ozone treatment for 30 min. The following organic compound layers were sequentially deposited on this transparent anode (ITO film) by means of vacuum deposition.

First layer: CuPc: film thickness 10 nm
Second layer: NPD: film thickness 30 nm
Third layer: Host material shown in Table 1 and RD-1 (mass ratio 93:7): film thickness 30 nm
Fourth layer: Material shown in Table 1: film thickness 10 nm
Fifth layer: Alq: film thickness 20 nm 0.1 nm-thick lithium fluoride and 100 nm-thick metal aluminum were deposited in this order thereon, thereby forming a cathode.

This stacked body was placed in a glove box substituted with a nitrogen gas without being contacted with the atmosphere and sealed by using a glass-made sealing can and a UV-curable adhesive (XNR5516HV, manufactured by Nagase-CHIBA Ltd.) to obtain an organic electroluminescent device.

As a result of emitting light from these devices, light emission derived from each of the light emitting materials could be obtained.

(Evaluation of Performance of Organic Electroluminescent Device)

Each device obtained was evaluated from the viewpoint of the efficiency, driving voltage, durability, change in chromaticity when driving at high luminance, change in chromaticity by aging when driving at high luminance and increase in driving voltage by aging when driving at a high luminance. Meanwhile, various measurements were performed as follows. The results are shown in Table 1.

(a) Efficiency

A direct current voltage was applied to each device by using a Source Measure Unit 2400 manufactured by TOYO Corporation to emit light, and then the luminance thereof was measured by using a luminance meter BM-8 manufactured by TOPCON CORPORATION. The light emission spectra and light emission wavelengths were measured by using a spectrum analyzer PMA-11 manufactured by Hamamatsu Photonics K.K. Based on these, the external quantum efficiency in the vicinity of a luminance of 1,000 cd/m$^2$ was calculated by a luminance conversion method, and was shown as a relative value in each Table by using each of the values of device 1-1 in Table 1, device 2-1 in Table 2, device 3-1 in Table 3, device 4-1 in Table 4, device 5-1 in Table 5 and device 1-1 in Table 6 as 10. The larger the number, the more preferable the efficiency.

(b) Driving Voltage

Direct current voltage was applied to each device to enable the devices to emit light such that the luminance became 1,000 cd/m$^2$. At this time, the applied voltage was used as an index for evaluation of the driving voltage, and was shown as a relative value in each Table by using each of the values of device 1-1 in Table 1, device 2-1 in Table 2, device 3-1 in Table 3, device 4-1 in Table 4, device 5-1 in Table 5 and device 1-1 in Table 6 as 10. The smaller the number, the more preferable the driving voltage.

(c) Durability

Direct current voltage is applied to each device such that the luminance became 5,000 cd/m$^2$, and light was continuously emitted to obtain the time required until the luminance became 4,000 cd/m$^2$ as an index for durability, and the time was shown as a relative value in each Table by using each of the values of device 1-1 in Table 1, device 2-1 in Table 2, device 3-1 in Table 3, device 4-1 in Table 4, device 5-1 in Table 5 and device 1-1 in Table 6 as 10. The larger the number, the more preferable the durability.

(d) Change in Chromaticity when Driving at High Luminance

Direct current voltage was applied to each device to enable the devices to emit light such that the luminance became 20,000 cd/m$^2$. The chromaticity (x, y) at this time was compared to the chromaticity (x, y) when direct current voltage is applied such that the luminance becomes 1,000 cd/m$^2$ to emit light, and the differences in the x value and the y value of both the chromaticities were shown in the form of (Δx, Δy) and used as an index for the change in chromaticity when driving at a high luminance. The smaller the values of Δx and Δy, the more preferable.

(e) Change in Chromaticity by Aging when Driving at High Luminance

Direct current voltage is applied to each device such that the luminance is 20,000 cd/m$^2$ and light was continuously emitted. The chromaticity (x, y) at the initial driving was compared to the chromaticity (x, y) when the luminance was 10,000 cd/m$^2$, and the differences in the x value and the y value of both the chromaticities were shown in the form of (Δx, Δy) and used as an index for the change in chromaticity by aging when driving at a high luminance. The smaller the values of Δx and Δy, the more preferable.

(f) Increase in Driving Voltage by Aging when Driving at High Luminance

Direct current voltage is applied to each device such that the luminance becomes 20,000 cd/m$^2$ and light is continuously emitted. The difference between the voltage at the initial driving and the voltage when the luminance was 10,000 cd/m$^2$ was used as an index for the voltage rise by aging when driving at high luminance. The smaller this value, the more preferable.

Meanwhile, in Tables 1 to 6, the symbol "<" in the evaluation of change in chromaticity and change in chromaticity by aging means a sign of inequality, and for example, "<0.005" means that the change in chromaticity or the change in chromaticity by aging was less than 0.005, and ">0.02" means that the change in chromaticity or the change in chromaticity by aging was more than 0.02.

Furthermore, ">5" in the evaluation of voltage rise by aging means that the voltage rise by aging was more than 5, and "<1" in the evaluation of durability means that the durability (relative value) was less than 1.

TABLE 1

| Device number | Host material | Fourth layer material | Efficiency (relative value) | Driving voltage (relative value) | Durability (relative value) | Change in chromaticity (Δx, Δy) | When driving at high luminance Change in chromaticity by aging (Δx, Δy) | Voltage rise by aging (V) |
|---|---|---|---|---|---|---|---|---|
| Device 1-1 | Compound (1) | Compound (A) | 10 | 10 | 10 | (<0.005, <0.005) | (<0.005, <0.005) | 0.6 |
| Device 1-2 | Compound (1) | Compound (B) | 10 | 9 | 10 | (<0.005, <0.005) | (<0.005, <0.005) | 0.5 |
| Device 1-3 | Compound (1) | Compound (H) | 9 | 10 | 8 | (<0.005, <0.005) | (<0.005, <0.005) | 0.5 |
| Device 1-4 | Compound (2) | Compound (B) | 10 | 10 | 10 | (<0.005, <0.005) | (<0.005, <0.005) | 0.6 |
| Device 1-5 | Compound (2) | Compound (C) | 10 | 9 | 10 | (<0.005, <0.005) | (<0.005, <0.005) | 0.6 |
| Device 1-6 | Compound (9) | Compound (A) | 10 | 11 | 12 | (<0.005, <0.005) | (<0.005, <0.005) | 0.6 |
| Device 1-7 | Compound (9) | Compound (G) | 10 | 10 | 11 | (<0.005, <0.005) | (<0.005, <0.005) | 0.5 |
| Device 1-8 | Compound (11) | Compound (D) | 10 | 11 | 9 | (<0.005, <0.005) | (<0.005, <0.005) | 0.6 |
| Device 1-9 | Compound (11) | Compound (E) | 10 | 10 | 11 | (<0.005, <0.005) | (<0.005, <0.005) | 0.6 |
| Device 1-10 | Compound (13) | Compound (A) | 9 | 11 | 11 | (<0.005, <0.005) | (<0.005, <0.005) | 0.6 |
| Device 1-11 | Compound (13) | Compound (H) | 9 | 10 | 8 | (<0.005, <0.005) | (<0.005, <0.005) | 0.6 |
| Device 1-12 | Compound (20) | Compound (B) | 9 | 9 | 8 | (<0.005, <0.005) | (<0.005, <0.005) | 0.7 |

TABLE 1-continued

|  |  |  |  |  |  | When driving at high luminance | | |
|---|---|---|---|---|---|---|---|---|
| Device number | Host material | Fourth layer material | Efficiency (relative value) | Driving voltage (relative value) | Durability (relative value) | Change in chromaticity (Δx, Δy) | Change in chromaticity by aging (Δx, Δy) | Voltage rise by aging (V) |
| Device 1-13 | Compound (20) | Compound (I) | 9 | 10 | 7 | (<0.005, <0.005) | (<0.005, <0.005) | 0.6 |
| Device 1-14 | Compound (25) | Compound (F) | 9 | 10 | 11 | (<0.005, <0.005) | (<0.005, <0.005) | 0.5 |
| Device 1-15 | Compound (25) | Compound (G) | 9 | 10 | 11 | (<0.005, <0.005) | (<0.005, <0.005) | 0.6 |
| Comparative device 1-1 | Compound (1) | Alq | 8 | 11 | <1 | (<0.005, <0.005) | (<0.005, <0.005) | >5 |
| Comparative device 1-2 | Compound (1) | UGH-2 | 8 | 13 | <1 | (0.01, 0.01) | (0.01, 0.02) | 3.1 |
| Comparative device 1-3 | Compound (9) | BCP | 9 | 12 | <1 | (<0.005, <0.005) | (<0.005, <0.005) | >5 |
| Comparative device 1-4 | Compound (20) | ET-1 | 9 | 11 | 1 | (0.01, 0.01) | (0.01, 0.02) | 2.7 |
| Comparative device 1-5 | Compound (25) | ET-2 | 9 | 11 | 2 | (<0.005, <0.005) | (<0.005, <0.005) | 3.3 |
| Comparative device 1-6 | mCP | BAlq | 8 | 13 | <1 | (>0.02, >0.02) | (>0.02, >0.02) | 4.2 |
| Comparative device 1-7 | mCP | ET-2 | 8 | 13 | 1 | (>0.02, >0.02) | (>0.02, >0.02) | 3.8 |
| Comparative device 1-8 | mCBP | Alq | 8 | 13 | <1 | (>0.02, >0.02) | (>0.02, >0.02) | >5 |
| Comparative device 1-9 | mCBP | BCP | 8 | 12 | <1 | (>0.02, >0.02) | (>0.02, >0.02) | >5 |
| Comparative device 1-10 | CBP | Compound (A) | 8 | 13 | <1 | (0.01, 0.02) | (>0.02, >0.02) | 2.5 |
| Comparative device 1-11 | CBP | BCP | 8 | 13 | <1 | (>0.02, >0.02) | (>0.02, >0.02) | >5 |
| Comparative device 1-12 | CBP | ET-1 | 8 | 12 | <1 | (>0.02, >0.02) | (>0.02, >0.02) | 4.1 |
| Comparative device 1-13 | UGH-2 | Compound (D) | 8 | 13 | <1 | (0.01, 0.02) | (>0.02, >0.02) | 3.3 |
| Comparative device 1-14 | UGH-2 | ET-1 | 8 | 12 | <1 | (>0.02, >0.02) | (>0.02, >0.02) | 3.4 |
| Comparative device 1-15 | UGH-2 | UGH-2 | 8 | 16 | <1 | (>0.02, >0.02) | (>0.02, >0.02) | 3.7 |
| Comparative device 1-16 | ET-1 | Compound (G) | 8 | 12 | <1 | (>0.02, >0.02) | (>0.02, >0.02) | 3.1 |
| Comparative device 1-17 | ET-1 | ET-2 | 8 | 12 | <1 | (>0.02, >0.02) | (>0.02, >0.02) | >5 |
| Comparative device 1-18 | ET-1 | ET-1 | 9 | 11 | <1 | (>0.02, >0.02) | (>0.02, >0.02) | 4.3 |

Example 2

Devices 2-1 to 2-9 and Comparative devices 2-1 to 2-9 were manufactured in the same manner as in the device in Example 1 to perform the same evaluation as in Example 1, except that the light emitting material was changed from RD-1 to GD-1 and the host material and the fourth layer material were changed into the materials described in the following Table 2. The results are shown in Table 2.

TABLE 2

|  |  |  |  |  |  | When driving at high luminance | | |
|---|---|---|---|---|---|---|---|---|
| Device number | Host material | Fourth layer material | Efficiency (relative value) | Driving voltage (relative value) | Durability (relative value) | Change in chromaticity (Δx, Δy) | Change in chromaticity by aging (Δx, Δy) | Voltage rise by aging (V) |
| Device 2-1 | Compound (1) | Compound (A) | 10 | 10 | 10 | (<0.005, <0.005) | (<0.005, <0.005) | 1.4 |
| Device 2-2 | Compound (1) | Compound (G) | 10 | 10 | 11 | (<0.005, <0.005) | (<0.005, <0.005) | 1.2 |
| Device 2-3 | Compound (2) | Compound (B) | 10 | 10 | 10 | (<0.005, <0.005) | (<0.005, <0.005) | 1.4 |
| Device 2-4 | Compound (2) | Compound (H) | 10 | 11 | 8 | (<0.005, <0.005) | (<0.005, <0.005) | 1.1 |
| Device 2-5 | Compound (9) | Compound (C) | 10 | 11 | 10 | (<0.005, <0.005) | (<0.005, <0.005) | 1.5 |
| Device 2-6 | Compound (11) | Compound (A) | 10 | 10 | 11 | (<0.005, <0.005) | (<0.005, <0.005) | 1.3 |
| Device 2-7 | Compound (11) | Compound (E) | 10 | 10 | 11 | (<0.005, <0.005) | (<0.005, <0.005) | 1.2 |
| Device 2-8 | Compound (13) | Compound (D) | 10 | 10 | 9 | (<0.005, <0.005) | (<0.005, <0.005) | 1.2 |
| Device 2-9 | Compound (20) | Compound (F) | 10 | 10 | 10 | (<0.005, <0.005) | (<0.005, <0.005) | 1.3 |
| Comparative device 2-1 | Compound (1) | BCP | 9 | 11 | <1 | (0.01, 0.02) | (>0.02, >0.02) | >5 |
| Comparative device 2-2 | Compound (20) | ET-2 | 5 | 11 | 2 | (0.01, 0.02) | (>0.02, >0.02) | 4.1 |
| Comparative device 2-3 | mCP | BAlq | 6 | 12 | <1 | (0.01, 0.02) | (>0.02, >0.02) | >5 |
| Comparative device 2-4 | CBP | Compound (B) | 9 | 12 | <1 | (>0.02, >0.02) | (>0.02, >0.02) | 3.9 |
| Comparative device 2-5 | CBP | ET-2 | 5 | 12 | <1 | (>0.02, >0.02) | (>0.02, >0.02) | >5 |
| Comparative device 2-6 | UGH-2 | Compound (H) | 9 | 12 | <1 | (0.01, 0.02) | (>0.02, >0.02) | >5 |
| Comparative device 2-7 | UGH-2 | UGH-2 | 7 | 13 | <1 | (0.01, 0.02) | (>0.02, >0.02) | >5 |
| Comparative device 2-8 | ET-1 | Compound (E) | 9 | 12 | <1 | (>0.02, >0.02) | (>0.02, >0.02) | >5 |
| Comparative device 2-9 | ET-1 | ET-1 | 9 | 12 | <1 | (>0.02, >0.02) | (>0.02, >0.02) | >5 |

Example 3

Devices 3-1 to 3-8 and Comparative devices 3-1 to 3-9 were manufactured in the same manner as in the device in Example 1 to perform the same evaluation as in Example 1, except that the light emitting material was changed from RD-1 to GD-2, and the host material and the fourth layer material were changed into the materials described in the following Table 3. The results are shown in Table 3.

From Tables 1 to 4, it was revealed that the device of the inventive examples has excellent light emission efficiency and durability, and that it is possible to obtain an organic electroluminescence device which has a low driving voltage, a small change in chromaticity when driving at high luminance, a small change in chromaticity by aging and a small voltage rise by aging.

TABLE 3

| Device number | Host material | Fourth layer material | Efficiency (relative value) | Driving voltage (relative value) | Durability (relative value) | When driving at high luminance Change in chromaticity (Δx, Δy) | Change in chromaticity by aging (Δx, Δy) | Voltage rise by aging (V) |
|---|---|---|---|---|---|---|---|---|
| Device 3-1 | Compound (1) | Compound (D) | 10 | 10 | 10 | (<0.005, <0.005) | (<0.005, <0.005) | 1.2 |
| Device 3-2 | Compound (1) | Compound (I) | 10 | 10 | 8 | (<0.005, <0.005) | (<0.005, <0.005) | 1.1 |
| Device 3-3 | Compound (2) | Compound (E) | 10 | 10 | 10 | (<0.005, <0.005) | (<0.005, <0.005) | 1.4 |
| Device 3-4 | Compound (2) | Compound (F) | 10 | 10 | 11 | (<0.005, <0.005) | (<0.005, <0.005) | 1.5 |
| Device 3-5 | Compound (9) | Compound (B) | 10 | 10 | 10 | (<0.005, <0.005) | (<0.005, <0.005) | 1.4 |
| Device 3-6 | Compound (9) | Compound (C) | 10 | 10 | 9 | (<0.005, <0.005) | (<0.005, <0.005) | 1.3 |
| Device 3-7 | Compound (13) | Compound (G) | 10 | 10 | 10 | (<0.005, <0.005) | (<0.005, <0.005) | 1.2 |
| Device 3-8 | Compound (20) | Compound (H) | 9 | 10 | 8 | (<0.005, <0.005) | (<0.005, <0.005) | 1.4 |
| Comparative device 3-1 | Compound (20) | ET-1 | 10 | 10 | 2 | (0.01, 0.02) | (>0.02, >0.02) | >5 |
| Comparative device 3-2 | Compound (25) | BAlq | 9 | 11 | 3 | (0.01, 0.02) | (>0.02, >0.02) | >5 |
| Comparative device 3-3 | mCP | BCP | 9 | 11 | <1 | (>0.02, >0.02) | (>0.02, >0.02) | >5 |
| Comparative device 3-4 | CBP | Compound (B) | 9 | 11 | <1 | (>0.02, >0.02) | (>0.02, >0.02) | 4.9 |
| Comparative device 3-5 | CBP | ET-1 | 9 | 11 | <1 | (>0.02, >0.02) | (>0.02, >0.02) | >5 |
| Comparative device 3-6 | UGH-2 | Compound (F) | 9 | 12 | <1 | (>0.02, >0.02) | (>0.02, >0.02) | 4.4 |
| Comparative device 3-7 | UGH-2 | UGH-2 | 7 | 13 | <1 | (>0.02, >0.02) | (>0.02, >0.02) | >5 |
| Comparative device 3-8 | ET-1 | Compound (I) | 9 | 11 | <1 | (>0.02, >0.02) | (>0.02, >0.02) | >5 |
| Comparative device 3-9 | ET-1 | ET-1 | 9 | 11 | <1 | (>0.02, >0.02) | (>0.02, >0.02) | >5 |

Example 4

Devices 4-1 to 4-6 and Comparative devices 4-1 to 4-8 were manufactured in the same manner as in the device in Example 1 to perform the same evaluation as in Example 1, except that the light emitting material was changed from RD-1 to BD-1 and the host material and the fourth layer material were changed into the materials described in the following Table 4. The results are shown in Table 4.

Example 5

A glass substrate having an ITO film having a thickness of 0.5 mm and each side of 2.5 cm in square (manufactured by GEOMATEC Co., Ltd., and surface resistance 10Ω/□) was put into a washing container, and ultrasonically washed in 2-propanol, followed by UV-ozone treatment for 30 min. An aqueous solution (BaytronP (standard product)) of poly (3,4-ethylenedioxythiophene) (PEDOT)/polystyrene sulfonic acid(PSS)) was spin-coated (at 4,000 rpm for 60 sec) on

TABLE 4

| Device number | Host material | Fourth layer material | Efficiency (relative value) | Driving voltage (relative value) | Durability (relative value) | When driving at high luminance Change in chromaticity (Δx, Δy) | Change in chromaticity by aging (Δx, Δy) | Voltage rise by aging (V) |
|---|---|---|---|---|---|---|---|---|
| Device 4-1 | Compound (1) | Compound (A) | 10 | 10 | 10 | (<0.005, <0.005) | (<0.005, <0.005) | 1.5 |
| Device 4-2 | Compound (1) | Compound (E) | 10 | 10 | 11 | (<0.005, <0.005) | (<0.005, <0.005) | 1.3 |
| Device 4-3 | Compound (9) | Compound (G) | 10 | 10 | 12 | (<0.005, <0.005) | (<0.005, <0.005) | 1.5 |
| Device 4-4 | Compound (9) | Compound (H) | 10 | 11 | 9 | (<0.005, <0.005) | (<0.005, <0.005) | 1.5 |
| Device 4-5 | Compound (13) | Compound (C) | 10 | 10 | 10 | (<0.005, <0.005) | (<0.005, <0.005) | 1.7 |
| Device 4-6 | Compound (13) | Compound (D) | 10 | 11 | 10 | (<0.005, <0.005) | (<0.005, <0.005) | 1.4 |
| Comparative device 4-1 | Compound (1) | BCP | 10 | 11 | <1 | (0.01, 0.02) | (>0.02, >0.02) | >5 |
| Comparative device 4-2 | Compound (13) | ET-2 | 10 | 12 | 3 | (0.01, 0.02) | (>0.02, >0.02) | >5 |
| Comparative device 4-3 | CBP | Compound (D) | 9 | 12 | <1 | (0.01, 0.02) | (>0.02, >0.02) | >5 |
| Comparative device 4-4 | CBP | ET-1 | 10 | 12 | <1 | (>0.02, >0.02) | (>0.02, >0.02) | >5 |
| Comparative device 4-5 | UGH-2 | Compound (F) | 8 | 13 | <1 | (0.01, 0.02) | (>0.02, >0.02) | >5 |
| Comparative device 4-6 | UGH-2 | UCH-2 | 8 | 15 | <1 | (>0.02, >0.02) | (>0.02, >0.02) | >5 |
| Comparative device 4-7 | ET-1 | Compound (H) | 8 | 13 | <1 | (0.01, 0.02) | (>0.02, >0.02) | >5 |
| Comparative device 4-8 | ET-1 | ET-1 | 9 | 11 | <1 | (>0.02, >0.02) | (>0.02, >0.02) | >5 | this transparent anode (ITO film) and dried at 120° C. for 10 min to form a hole transporting layer (thickness 150 nm).

Subsequently, a toluene solution containing 1 mass % of the host material shown in Table 5 and 0.05 mass % of RD-1 was spin-coated (at 2,000 rpm for 60 sec) on the above hole transporting layer to form a light emitting layer (thickness 50 nm).

The compound described in the item of the electron transporting layer shown in Table 5 was used and deposited in a thickness of 10 nm on this light emitting layer by a vacuum deposition method, thereby forming the resulting layer as an electron transporting layer, and Alq was deposited as an electron injection layer in a thickness of 20 nm by a vacuum deposition method. Furthermore, 0.1 nm-thick lithium fluoride and a 100 nm-thick metal aluminum were deposited in this order thereon, thereby forming a cathode.

This stacked body was placed in a glove box substituted with a nitrogen gas without being contacted with the atmosphere and sealed by using a glass-made sealing can and a UV-curable adhesive (XNR5516HV, manufactured by Nagase-CHIBA Ltd.) to obtain devices 5-1 to 5-8 and comparative devices 5-1 to 5-9 of the present invention. The devices obtained were subjected to the same evaluation as in device 1-1, and the result is shown in Table 5.

were formed by a solution application process, it was revealed that it is possible to obtain an organic electroluminescence device which has excellent light emission efficiency and durability, a low driving voltage, a small change in chromaticity when driving at high luminance, a small change in chromaticity by aging and a small voltage rise by aging.

Example 6

Devices 6-1 to 6-7 and comparative devices 6-1 and 6-2 were manufactured in the same manner as in device 1-1 to perform the same evaluation as in device 1-1, except that the first layer, the host material, the fourth layer and the fifth layer of device 1-1 were changed into the configuration shown in Table 6. Meanwhile, NPD:MoO$_3$ represents a mass

TABLE 5

| | | | | | | When driving at high luminance | | |
|---|---|---|---|---|---|---|---|---|
| Device number | Host material | Electron transporting layer | Efficiency (relative value) | Driving voltage (relative value) | Durability (relative value) | Change in chromaticity ($\Delta x, \Delta y$) | Change in chromaticity by aging ($\Delta x, \Delta y$) | Voltage rise by aging (V) |
| Device 5-1 | Compound (1) | Compound (A) | 10 | 10 | 10 | (<0.005, <0.005) | (<0.005, <0.005) | 1.4 |
| Device 5-2 | Compound (1) | Compound (D) | 10 | 10 | 12 | (<0.005, <0.005) | (<0.005, <0.005) | 1.2 |
| Device 5-3 | Compound (2) | Compound (C) | 10 | 10 | 13 | (<0.005, <0.005) | (<0.005, <0.005) | 1.6 |
| Device 5-4 | Compound (9) | Compound (E) | 10 | 11 | 13 | (<0.005, <0.005) | (<0.005, <0.005) | 1.3 |
| Device 5-5 | Compound (11) | Compound (I) | 10 | 10 | 14 | (<0.005, <0.005) | (<0.005, <0.005) | 1.4 |
| Device 5-6 | Compound (13) | Compound (H) | 10 | 10 | 11 | (<0.005, <0.005) | (<0.005, <0.005) | 1.5 |
| Device 5-7 | Compound (20) | Compound (B) | 10 | 10 | 14 | (<0.005, <0.005) | (<0.005, <0.005) | 1.3 |
| Device 5-8 | Compound (25) | Compound (F) | 10 | 10 | 11 | (<0.005, <0.005) | (<0.005, <0.005) | 1.4 |
| Comparative device 5-1 | Compound (1) | BCP | 10 | 11 | <1 | (0.01, 0.02) | (>0.02, >0.02) | >5 |
| Comparative device 5-2 | Compound (11) | ET-2 | 10 | 11 | 3 | (0.01, 0.02) | (0.01, 0.02) | 4.3 |
| Comparative device 5-3 | mCP | BAlq | 9 | 11 | <1 | (>0.02, >0.02) | (>0.02, >0.02) | 3.8 |
| Comparative device 5-4 | CBP | Compound (B) | 9 | 11 | 1 | (>0.02, >0.02) | (>0.02, >0.02) | 4.4 |
| Comparative device 5-5 | CBP | ET-2 | 9 | 12 | <1 | (>0.02, >0.02) | (>0.02, >0.02) | >5 |
| Comparative device 5-6 | UGH-2 | Compound (D) | 9 | 11 | 1 | (0.01, 0.02) | (0.01, 0.02) | 4.1 |
| Comparative device 5-7 | UGH-2 | UGH-2 | 9 | 12 | <1 | (>0.02, >0.02) | (>0.02, >0.02) | >5 |
| Comparative device 5-8 | ET-1 | Compound (E) | 9 | 11 | <1 | (0.01, 0.02) | (0.01, 0.02) | 4.5 |
| Comparative device 5-9 | ET-1 | ET-1 | 9 | 10 | <1 | (>0.02, >0.02) | (>0.02, >0.02) | >5 |

From Table 5, even in a device of the present invention in which a hole transporting layer and a light emitting layer were formed by a solution application process, it was ratio of NPD and MoO$_3$, and Alq:Li represents a mass ratio of Alq and Li.

TABLE 6

| | | | | | | | | When driving at high luminance | | |
|---|---|---|---|---|---|---|---|---|---|---|
| Device number | First layer material | Host material | Fourth layer material | Fifth layer material | Efficiency (relative value) | Driving voltage (relative value) | Durability (relative value) | Change in chromaticity ($\Delta x, \Delta y$) | Change in chromaticity by aging ($\Delta x, \Delta y$) | Voltage rise by aging (V) |
| Device 1-1 | CuPc | Compound (1) | Compound (A) | Alq | 10 | 10 | 10 | (<0.005, <0.005) | (<0.005, <0.005) | 0.6 |
| Device 6-1 | NPD:MoO$_3$ = 70:30 | Compound (1) | Compound (A) | Alq | 10 | 8 | 10 | (<0.005, <0.005) | (<0.005, <0.005) | 0.7 |
| Device 6-2 | CuPc | Compound (1) | Compound (A) | Alq:Li = 99.5:0.5 | 10 | 9 | 11 | (<0.005, <0.005) | (<0.005, <0.005) | 0.7 |
| Device 6-3 | NPD:MoO$_3$ = 70:30 | Compound (1) | Compound (A) | Alq:Li = 99.5:0.5 | 11 | 7 | 12 | (<0.005, <0.005) | (<0.005, <0.005) | 0.5 |
| Device 1-5 | CuPc | Compound (2) | Compound (C) | Alq | 10 | 9 | 10 | (<0.005, <0.005) | (<0.005, <0.005) | 0.6 |

TABLE 6-continued

| Device number | First layer material | Host material | Fourth layer material | Fifth layer material | Efficiency (relative value) | Driving voltage (relative value) | Durability (relative value) | When driving at high luminance | | Voltage rise by aging (V) |
| --- | --- | --- | --- | --- | --- | --- | --- | --- | --- | --- |
| | | | | | | | | Change in chromaticity (Δx, Δy) | Change in chromaticity by aging (Δx, Δy) | |
| Device 6-4 | NPD:MoO$_3$ = 70:30 | Compound (2) | Compound (C) | Alq:Li = 99.5:0.5 | 10 | 7 | 11 | (<0.005, <0.005) | (<0.005, <0.005) | 0.6 |
| Device 1-7 | CuPc | Compound (9) | Compound (G) | Alq | 10 | 10 | 11 | (<0.005, <0.005) | (<0.005, <0.005) | 0.5 |
| Device 6-5 | NPD:MoO$_3$ = 70:30 | Compound (9) | Compound (G) | Alq:Li = 99.5:0.5 | 11 | 8 | 14 | (<0.005, <0.005) | (<0.005, <0.005) | 0.5 |
| Device 1-8 | CuPc | Compound (11) | Compound (D) | Alq | 10 | 11 | 9 | (<0.005, <0.005) | (<0.005, <0.005) | 0.6 |
| Device 6-6 | NPD:MoO$_3$ = 70:30 | Compound (11) | Compound (D) | Alq:Li = 99.5:0.5 | 10 | 8 | 10 | (<0.005, <0.005) | (<0.005, <0.005) | 0.6 |
| Device 1-11 | CuPc | Compound (13) | Compound (H) | Alq | 9 | 10 | 8 | (<0.005, <0.005) | (<0.005, <0.005) | 0.6 |
| Device 6-7 | NPD:MoO$_3$ = 70:30 | Compound (13) | Compound (H) | Alq:Li = 99.5:0.5 | 10 | 8 | 9 | (<0.005, <0.005) | (<0.005, <0.005) | 0.6 |
| Comparative device 1-4 | CuPc | Compound (20) | ET-1 | Alq | 9 | 11 | 1 | (0.01, 0.01) | (0.01, 0.02) | 2.7 |
| Comparative device 6-1 | NPD:MoO$_3$ = 70:30 | Compound (20) | ET-1 | Alq:Li = 99.5:0.5 | 8 | 9 | <1 | (>0.02, >0.02) | (>0.02, >0.02) | >5 |
| Comparative device 1-10 | CuPc | CBP | Compound (A) | Alq | 8 | 13 | <1 | (0.01, 0.02) | (>0.02, >0.02) | 2.5 |
| Comparative device 6-2 | NPD:MoO$_3$ = 70:30 | CBP | Compound (A) | Alq:Li = 99.5:0.5 | 6 | 11 | <1 | (>0.02, >0.02) | (>0.02, >0.02) | >5 |

From Table 6, it would be understood that by preparing a hole injection layer and an electron injection layer to contain an electron accepting dopant and an electron donating dopant respectively, it is possible to obtain an organic electroluminescence device of which voltage was greatly decreased and efficiency was improved, and which has excellent driving durability, a small change in chromaticity when driving at high luminance, a small change in chromaticity by aging and a small voltage rise by aging.

Hereinafter, the structures of the compounds used in Examples 1 to 6 will be shown.

[Chem. 45]

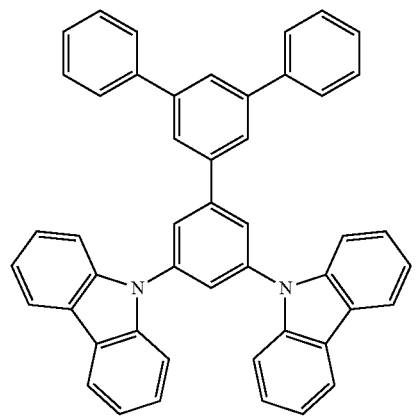

(1)

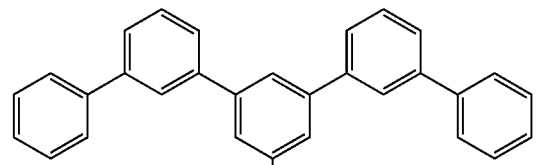

(2)

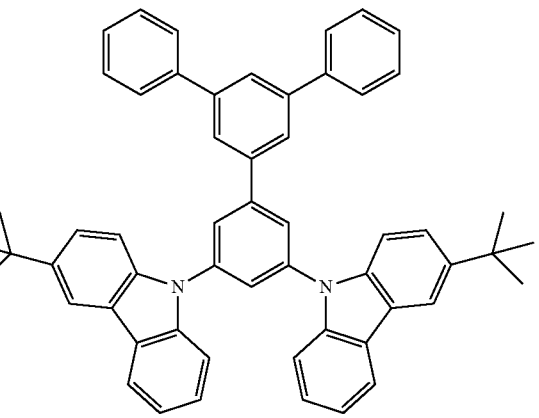

(9)

-continued
(11)
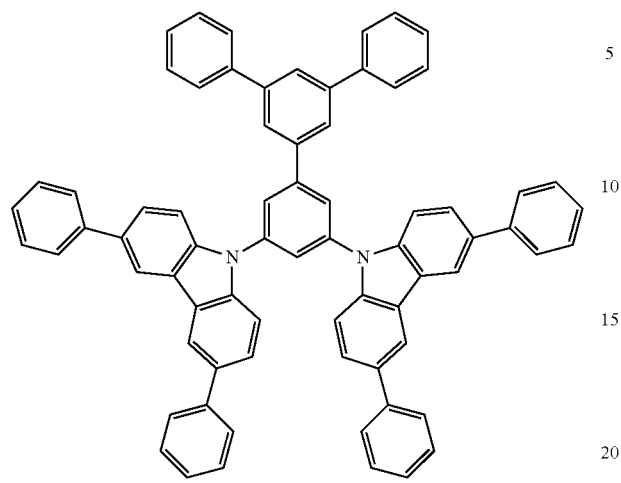
(13)
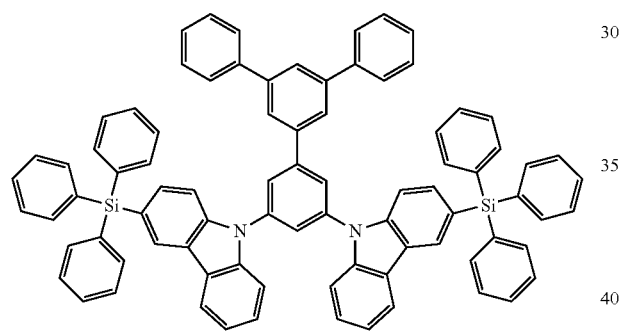
(20)
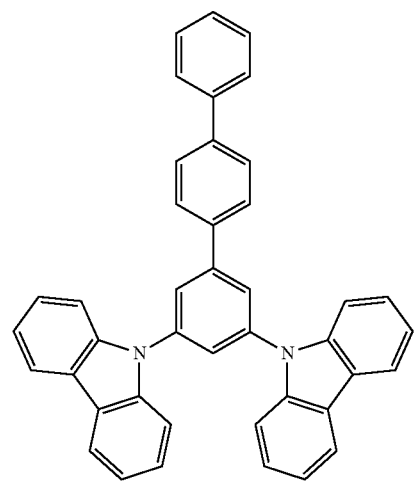
-continued
(25)
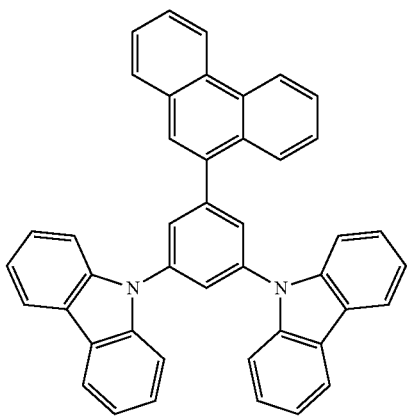
[Chem. 46]
(A)
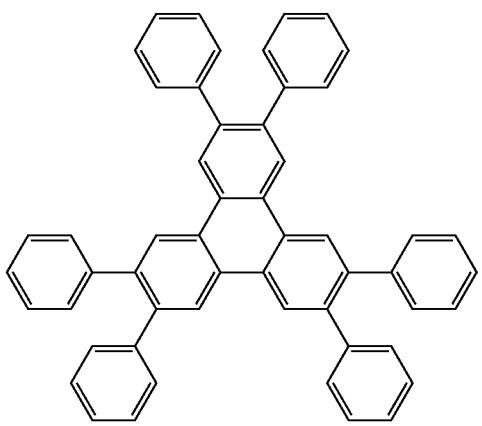
(B)
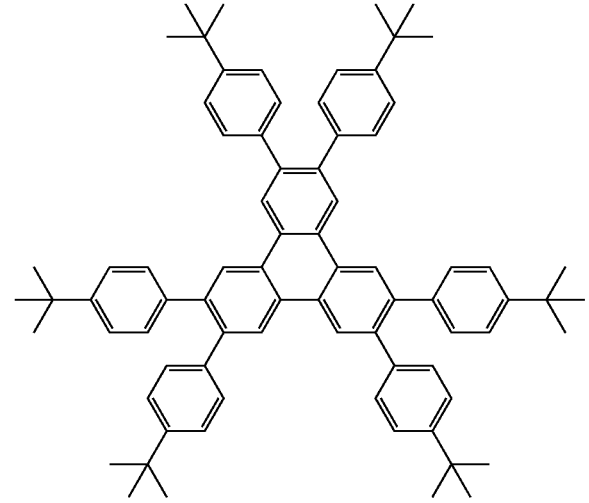

103
-continued
(C)
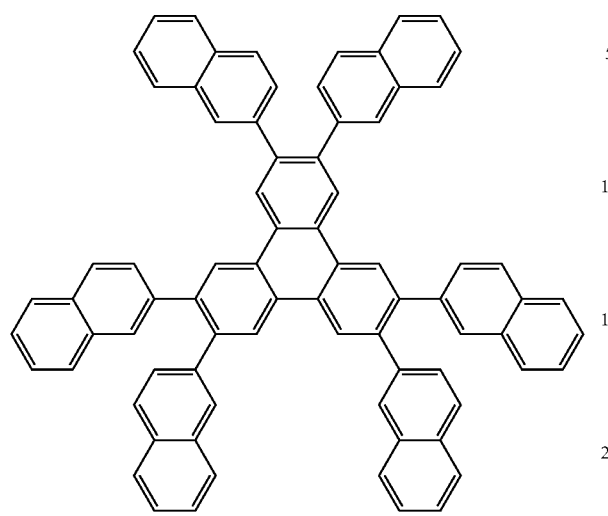
(D)
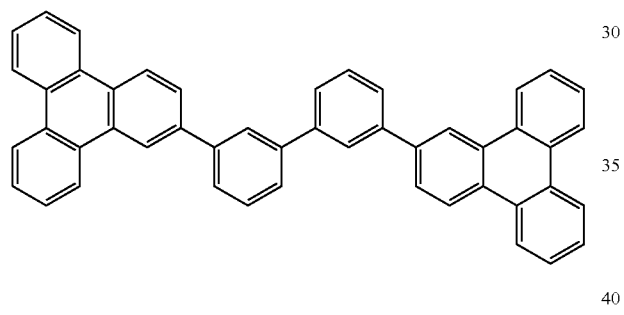
(E)
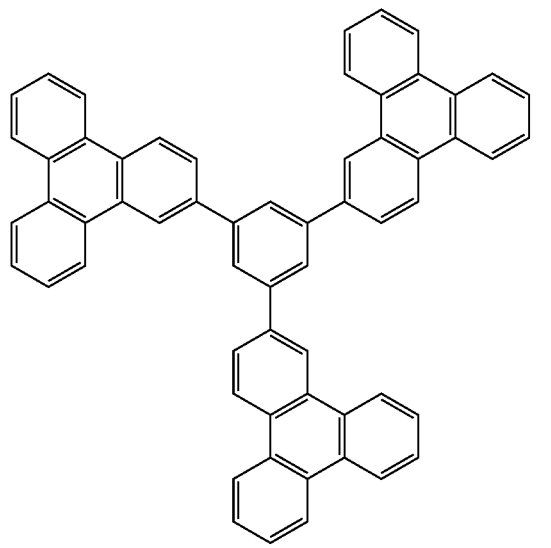
104
-continued
(F)
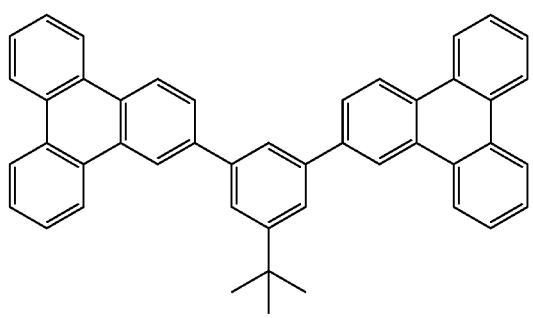
(G)
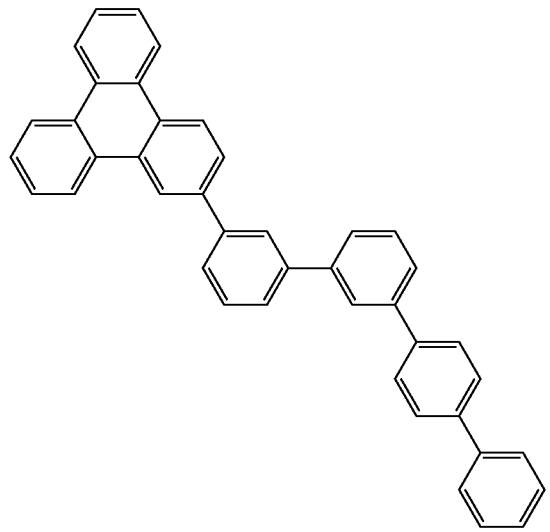
(H)
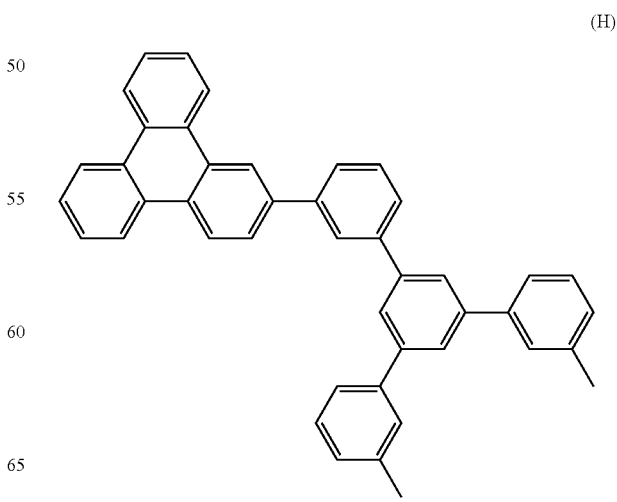

(I)
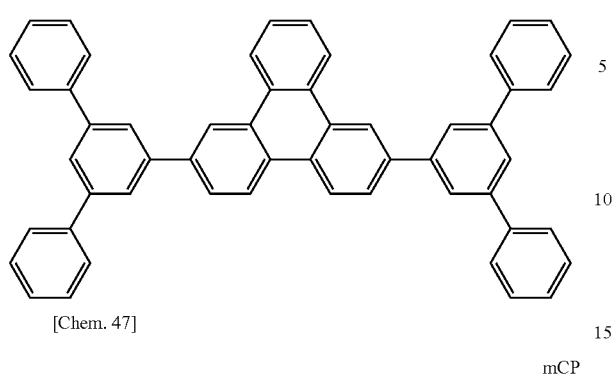
[Chem. 47]
mCP
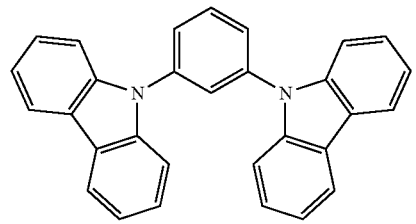
mCBP
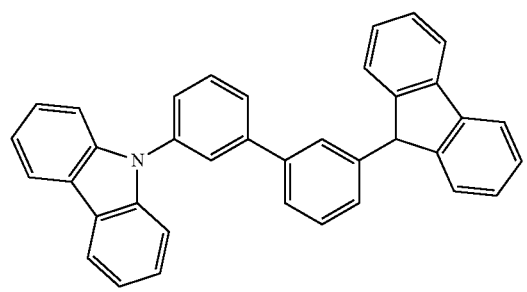
CBP
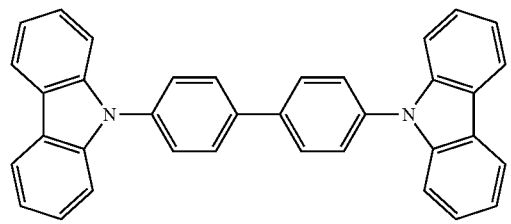
BAlq
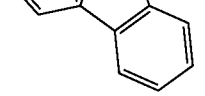
BCP
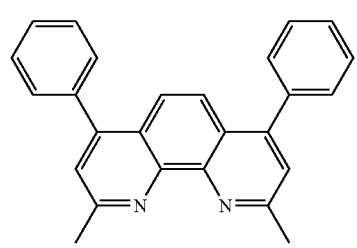
UGH-2
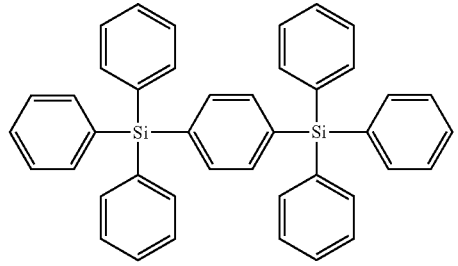
ET-1
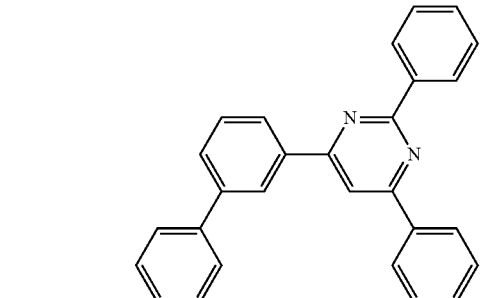
ET-2
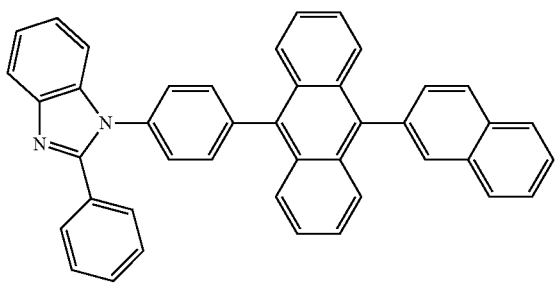
[Chem. 48]
CuPc
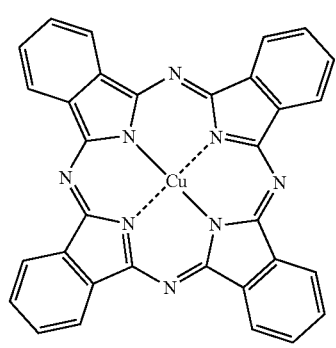

NPD

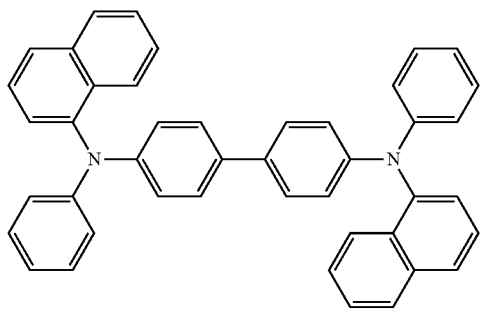

Alq

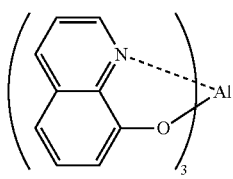

RD-1

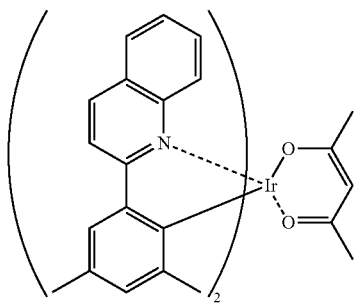

GD-1

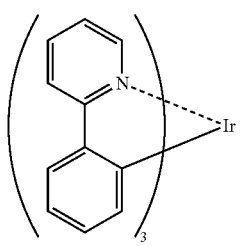

GD-2

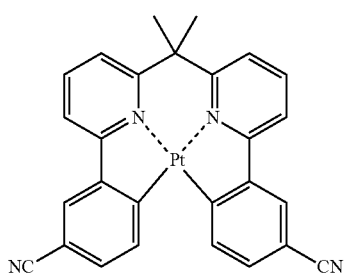

BD-1

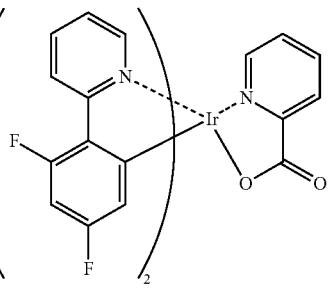

INDUSTRIAL APPLICABILITY

According to the present invention, it is possible to provide an organic electroluminescence device which has excellent light emission efficiency and durability, a low driving voltage, a small change in chromaticity when driving at high luminance, a small change in chromaticity by aging and a small voltage rise by aging.

Although the present invention has been described with reference to detailed and specific embodiments thereof, it is obvious to those skilled in the art that various changes or modifications may be made without departing from the spirit and scope of the present invention.

The present application is based on Japanese Patent Application (Patent Application No. 2010-7541) filed on Jan. 15, 2010 and Japanese Patent Application (Patent Application No. 2010-116667) filed on May 20, 2010, the contents of which are herein incorporated by reference.

EXPLANATION OF REFERENCE NUMERALS AND SYMBOLS

2: Substrate
3: Anode
4: Hole injection layer
5: Hole transporting layer
6: Light emitting layer
7: Hole blocking layer
8: Electron transporting layer
9: Cathode
10: Organic electroluminescence device
11: Organic layer
12: Protective layer
14: Adhesion layer
16: Sealing container
20: Light emission apparatus
30: Light scattering member
31: Transparent substrate
30A: Light incident surface
30B: Light exit surface
32: Fine particle
40: Illumination apparatus

The invention claimed is:
1. An organic electroluminescence device, comprising:
a pair of electrodes composed of an anode and a cathode;
a light emitting layer between the electrodes; and
an organic layer which is adjacent to the light emitting layer between the light emitting layer and the cathode, on a substrate,
wherein the light emitting layer comprises at least one compound represented by the following Formula (1), and the organic layer adjacent to the light emitting layer, which is on the cathode side of the light emitting layer, comprises at least one hydrocarbon compound represented by Formula (Tp-3):

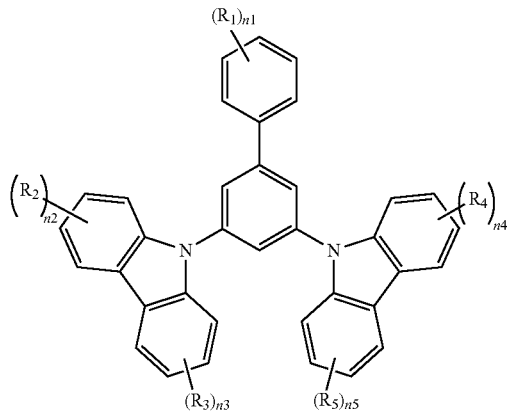

(1)

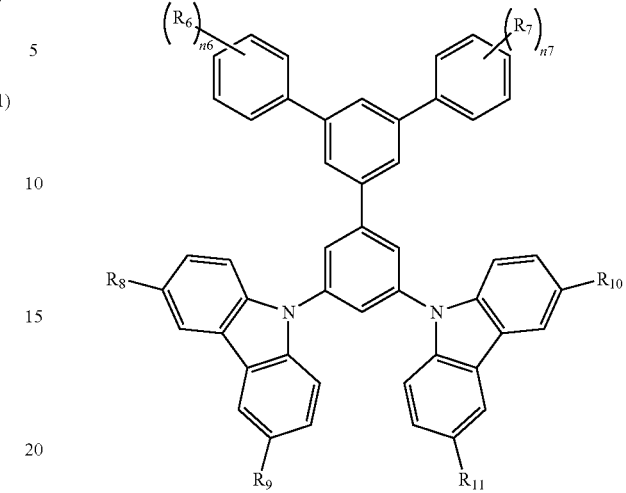

(2)

in Formula (1), $R_1$ represents a phenyl group and may further have a substituent Z, in the case where $R_1$ is present in plurality, each of a plurality of $R_1$ may be the same or different, each of $R_2$ to $R_5$ independently represents a t-butyl group, a phenyl group, or a triphenylsilyl group, in the case where each of $R_2$ to $R_5$ is present in plurality, each of a plurality of $R_2$ to $R_5$ may be the same or different, the substituent Z represents a phenyl group, n1 represents an integer of 0 to 2, each of n2 to n5 independently represents an integer of 0 to 1:

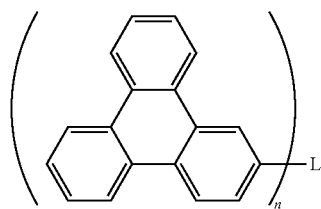

Formula (Tp-3)

in Formula (Tp-3),

L represents a phenyl group, which may be substituted with a C1-C5 alkyl group or a phenyl group, or an n-valent linking group formed by combining these groups, and n represents an integer of 1 to 3.

2. The organic electroluminescence device according to claim 1,
wherein the compound represented by Formula (1) is a compound represented by the following Formula (2):

in Formula (2)
each of $R_6$ and $R_7$ independently represents a phenyl group,
each of n6 and n7 independently represents an integer of 0 to 1,
each of $R_8$ to $R_{11}$ independently represents a hydrogen atom, a t-butyl group, a phenyl group, or a triphenylsilyl group.

3. The organic electroluminescence device according to claim 1,
wherein the light emitting layer comprises at least one phosphorescent light emitting material.

4. The organic electroluminescence device according to claim 1,
wherein at least one layer of the light emitting layer, the organic layer adjacent to the light emitting layer and other organic layers present between the anode and the cathode are formed by a solution application process.

5. The organic electroluminescence device according to claim 1,
wherein the device contains a hole injection layer between the electrodes and contains an electron accepting dopant in the hole injection layer.

6. The organic electroluminescence device according to claim 1,
wherein the device contains an electron injection layer between the electrodes and contains an electron donating dopant in the electron injection layer.

7. A light emission apparatus using the organic electroluminescence device according to claim 1.

8. A display apparatus using the organic electroluminescence device according to claim 1.

9. An illumination apparatus using the organic electroluminescence device according to claim 1.

10. The organic electroluminescence device according to claim 1,
wherein the light emitting layer further comprises a light emitting material in an amount of 0.1 mass % to 50 mass %.

* * * * *